US006849620B2

(12) United States Patent
Walker et al.

(10) Patent No.: US 6,849,620 B2
(45) Date of Patent: Feb. 1, 2005

(54) N-(AZABICYCLO MOIETIES)-SUBSTITUTED HETERO-BICYCLIC AROMATIC COMPOUNDS FOR THE TREATMENT OF DISEASE

(75) Inventors: Daniel Patrick Walker, Kalamazoo, MI (US); Eric Jon Jacobsen, Richland, MI (US); David W. Piotrowski, Portage, MI (US); Brad A. Acker, Kalamazoo, MI (US); Donn G. Wishka, Kalamazoo, MI (US); Jeffrey W. Corbett, Portage, MI (US); Mark R. Rauckhorst, Portage, MI (US); Vincent E. Groppi, Jr., Kalamazoo, MI (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/272,802

(22) Filed: Oct. 17, 2002

(65) Prior Publication Data

US 2003/0176702 A1 Sep. 18, 2003

Related U.S. Application Data

(60) Provisional application No. 60/342,674, filed on Dec. 21, 1991, and provisional application No. 60/344,436, filed on Oct. 26, 2001.

(51) Int. Cl.[7] .................... A61K 31/435; A61K 31/44; C07D 453/00; C07D 471/08; C07D 487/08
(52) U.S. Cl. .................. 514/214; 514/299; 514/301; 514/302; 514/303; 514/305; 514/367; 514/373; 514/375; 514/379; 514/394; 514/403; 514/413; 540/582; 546/112; 546/114; 546/115; 546/118; 546/120; 546/133; 548/159; 548/207; 548/217; 548/241; 548/306.1; 548/452; 548/454
(58) Field of Search .................. 540/582; 546/112, 546/114, 115, 118, 120, 133; 548/159, 207, 217, 241, 306.1, 454, 452; 514/214, 299, 301, 302, 303, 305, 367, 373, 375, 379, 394, 403, 413

(56) References Cited

U.S. PATENT DOCUMENTS

| | | | |
|---|---|---|---|
| 4,605,652 A | 8/1986 | Welstead, Jr. ............... 514/214 |
| 4,721,720 A | 1/1988 | Wootton et al. ............ 514/304 |
| 4,797,406 A | 1/1989 | Richardson et al. ........ 514/299 |
| 4,798,829 A | 1/1989 | King et al. .................. 514/214 |
| 4,803,199 A | 2/1989 | Donatsch et al. ........... 514/214 |
| 4,822,795 A | 4/1989 | King .......................... 514/214 |
| 4,835,162 A | 5/1989 | Abood ....................... 514/305 |
| 4,863,919 A | 9/1989 | Smith ......................... 514/214 |
| 4,882,327 A | 11/1989 | King .......................... 514/214 |
| 4,910,193 A | 3/1990 | Buchheit .................... 514/216 |
| 4,920,127 A | 4/1990 | King et al. .................. 514/278 |
| 4,920,219 A | 4/1990 | Pelletier et al. ............. 540/523 |
| 4,920,227 A | 4/1990 | Pelletier et al. ............. 546/133 |
| 4,921,982 A | 5/1990 | Cohen et al. ............... 549/462 |
| 4,933,445 A | 6/1990 | Pelletier .................... 540/552 |
| 4,935,511 A | 6/1990 | Youssefyeh et al. ........ 540/552 |
| 4,937,247 A | 6/1990 | King .......................... 514/299 |
| 4,973,594 A | 11/1990 | Tyers ......................... 514/299 |
| 4,983,600 A | 1/1991 | Ward et al. ................. 514/214 |
| 4,985,437 A | 1/1991 | Tyers ......................... 514/304 |
| 5,039,680 A | 8/1991 | Imperato et al. ............ 514/304 |
| 5,063,231 A | 11/1991 | Sanger et al. ............... 514/214 |
| 5,114,947 A | 5/1992 | Imondi ....................... 514/282 |
| 5,175,173 A | 12/1992 | Sun ............................ 514/305 |
| 5,272,154 A | 12/1993 | Dixon ........................ 514/299 |
| 5,322,951 A | 6/1994 | King et al. ............... 548/312.1 |
| 5,342,845 A | 8/1994 | Chokai et al. .............. 514/305 |
| 5,352,685 A | 10/1994 | Maruyama et al. ......... 514/301 |
| 5,362,740 A | 11/1994 | Bedeschi et al. ........... 514/299 |
| 5,434,161 A | 7/1995 | Becker et al. .............. 514/300 |
| 5,543,426 A | 8/1996 | Dixon et al. ............... 514/410 |
| 5,561,149 A | 10/1996 | Azria et al. ................. 514/397 |
| 5,599,937 A | 2/1997 | Glas et al. .................. 546/133 |
| 5,686,461 A | 11/1997 | Cugola et al. .............. 514/278 |
| 6,054,464 A | 4/2000 | Macor et al. ............... 514/299 |

FOREIGN PATENT DOCUMENTS

| | | | |
|---|---|---|---|
| DE | 3724059 | 2/1988 | ......... C07D/451/12 |
| DE | 3810552 | 3/1998 | ......... C07D/451/12 |
| EP | 0279512 B1 | 1/1988 | .......... A61K/31/46 |
| EP | 0323077 A1 | 12/1988 | ......... C07D/451/04 |
| EP | 0 327 335 | 1/1989 | ......... C07D/453/02 |
| EP | 403882 A2 | 6/1990 | ......... C07D/451/02 |
| EP | 483 836 A1 | 5/1992 | ......... C07D/519/00 |
| EP | 496 064 A1 | 7/1992 | ......... C07D/405/12 |
| EP | 512 350 A2 | 11/1992 | ......... C07D/453/02 |
| JP | WO 90/14347 A | 11/1990 | ......... C07D/453/02 |
| JP | 04 247081 A | 9/1992 | ......... C07D/451/04 |
| WO | WO 91/09593 | 7/1991 | .......... A61K/31/00 |
| WO | WO 91/17161 | 11/1991 | ......... C07D/451/14 |
| WO | WO 92/10494 | 6/1992 | ......... C07D/451/00 |
| WO | WO 95/27490 | 10/1995 | ......... A61K/31/445 |
| WO | WO 96/33186 | 10/1996 | ......... C07D/307/79 |
| WO | WO 97/35860 | 10/1997 | ......... C07D/451/14 |
| WO | WO 00/73431 A2 | 12/2000 | ........... C12N/15/00 |
| WO | WO 01/76576 A2 | 3/2001 | .......... A61K/31/00 |
| WO | WO 01/36417 A1 | 5/2001 | ......... C07D/451/04 |
| WO | WO 01/60821 A1 | 8/2001 | ......... C07D/453/02 |

OTHER PUBLICATIONS

Cooper and Millar, *J. Neurochem*, 1997, 68(5), pp. 2140–2151.

Eisele et al., *Chimaeric nicotinic–serotonergic receptor combines distinct ligand binding and channel specificities*, Nature, 366(6454), pp. 479–483, 1993.

*Bioorg. & Med. Chem. Lett.* 11 (2001) 319–321.

*Bioorg. & Med. Chem. Lett.* 9 (1999) 1895–1900.

*Behavioral Brain Res.*, 113 (2000) 169–181.

*Eur. J. Med. Chem.*, 34(1999) 415–422.

*Primary Examiner*—Bernard Dentz
(74) *Attorney, Agent, or Firm*—Peter C. Richardson; Andrea E. Dorigo; Lorraine B. Ling

(57) ABSTRACT

The invention provides compounds of Formula I:

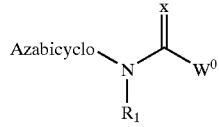
wherein Azabicyclo is
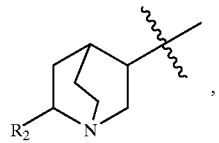
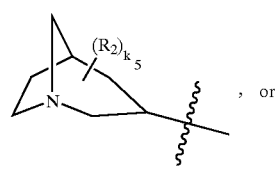
, or
Formula I
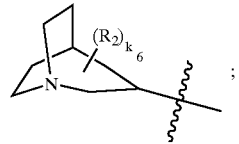
I
II
III
IV
V
-continued
VI
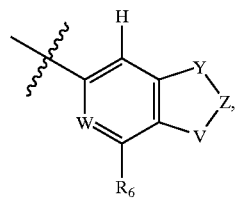
$W^0$ is a bicyclic moiety and is
(a)
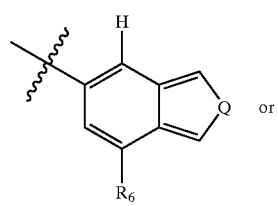
(b)
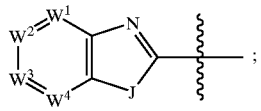
or
(c)
These compounds may be in the form of pharmaceutical salts or compositions, may be in pure enantiomeric form or racemic mixtures, and are useful in pharmaceuticals in which α7 is known to be involved.
31 Claims, No Drawings

N-(AZABICYCLO MOIETIES)-SUBSTITUTED HETERO-BICYCLIC AROMATIC COMPOUNDS FOR THE TREATMENT OF DISEASE

CROSS-REFERENCE TO RELATED APPLICATIONS

This application claims the benefit of U.S. provisional application Ser. No. 60/344,436 filed on Oct. 26, 2001, under 35 USC 119(e)(i), and U.S. provisional application Ser. No. 60/342,674 filed on Dec. 21, 2001, under 35 USC 119(e)(i), which are incorporated herein by reference in their entirety.

FIELD OF INVENTION

Nicotinic acetylcholine receptors (nAChRs) play a large role in central nervous system (CNS) activity. Particularly, they are known to be involved in cognition, learning, mood, emotion, and neuroprotection. There are several types of nicotinic acetylcholine receptors, and each one appears to have a different role in regulating CNS function. Nicotine affects all such receptors, and has a variety of activities. Unfortunately, not all of the activities are desirable. In fact, one of the least desirable properties of nicotine is its addictive nature and the low ratio between efficacy and safety. The present invention relates to molecules that have a greater effect upon the $\alpha 7$ nAChRs as compared to other closely related members of this large ligand-gated receptor family. Thus, the invention provides compounds that are active drug molecules with fewer side effects.

BACKGROUND OF THE INVENTION

Cell surface receptors are, in general, excellent and validated drug targets. nAChRs comprise a large family of ligand-gated ion channels that control neuronal activity and brain function. These receptors have a pentameric structure. In mammals, this gene family is composed of nine alpha and four beta subunits that co-assemble to form multiple subtypes of receptors that have a distinctive pharmacology. Acetylcholine is the endogenous regulator of all of the subtypes, while nicotine non-selectively activates all nAChRs.

The $\alpha 7$ nAChR is one receptor system that has proved to be a difficult target for testing. Native $\alpha 7$ nAChR is not routinely able to be stably expressed in most mammalian cell lines (Cooper and Millar, *J. Neurochem.*, 1997, 68(5) :2140–51). Another feature that makes functional assays of $\alpha 7$ nAChR challenging is that the receptor is rapidly (100 milliseconds) inactivated. This rapid inactivation greatly limits the functional assays that can be used to measure channel activity.

Recently, Eisele et al. has indicated that a chimeric receptor formed between the N-terminal ligand binding domain of the $\alpha 7$ nAChR (Eisele et al., *Nature*, 366(6454), p 479–83, 1993), and the pore forming C-terminal domain of the 5-HT$_3$ receptor expressed well in *Xenopus oocytes* while retaining nicotinic agonist sensitivity. Eisele et al. used the N-terminus of the avian (chick) form of the $\alpha 7$ nAChR receptor and the C-terminus of the mouse form of the 5-HT$_3$ gene. However, under physiological conditions the $\alpha 7$ nAChR is a calcium channel while the 5-HT$_3$R is a sodium and potassium channel. Indeed, Eisele et al. teaches that the chicken $\alpha 7$ nAChR/mouse 5-HT$_3$R behaves quite differently than the native $\alpha 7$ nAChR with the pore element not conducting calcium but actually being blocked by calcium ions. WO 00/73431 A2 reports on assay conditions under which the 5-HT$_3$R can be made to conduct calcium. This assay may be used to screen for agonist activity at this receptor.

U.S. Pat. No. 6,054,464 discloses azabicyclic esters of carbamic acids useful in therapy, especially in the treatment or prophylaxis of psychotic disorders and intellectual impairment disorders, as well as intermediates and use of intermediates in synthesis.

U.S. Pat. No. 5,977,144 discloses compositions for benzylidene- and cinnamylidene-anabaseines and methods for using these compositions for treating conditions associated with defects or malfunctioning of nicotinic subtypes brain receptors. These compositions target the $\alpha 7$ receptor subtype with little or no activation of the $\alpha 4\beta 2$ or other receptor subtypes.

U.S. Pat. No. 5,599,937 discloses heteroaromatic quinuclidines used for treating diseases related to muscarinic receptor function.

U.S. Pat. No. 5,561,149 discloses the use of a mono or bicyclic carbocyclic, or heterocyclic carboxylic acid, ester or amide or an imidazolyl carbazol in the manufacture of a medicament suitable for the treatment of stress-related psychiatric disorders, for increasing vigilance, for the treatment of rhinitis or serotonin-induced disorders and/or coadministration with another active agent to increase the bioavailability thereof, or for nasal administration.

U.S. Pat. No. 5,543,426 discloses the use of certain 3,7-disubstituted indole compounds for treating depression or cognitive disorders.

U.S. Pat. No. 5,434,161 discloses imidazopyridines as serotonergic 5-HT$_3$ antagonists.

U.S. Pat. No. 5,362,740 discloses dihydrobenzofuran carboxamides useful in treating CNS disorders, but motility disorders, and/or emisis and/or pain in mammals, and/or migraine.

U.S. Pat. No. 5,352,685 discloses thieno[3,2-b]pyridine derivatives effective for the prevention and therapeutical treatment of the symptoms caused by gastric hypanakinesis, such as heartburn, abdominal distension feeling, anorexia, unpleasant feeling on upper abdomen, abdominalgia, nausea, vomiting, etc. caused by the underlying diseases such as acute and chronic gastritis, stomach and duodenum ulcer, gastroneurosis, gastroptosis, etc.

U.S. Pat. No. 5,342,845 discloses indole derivatives and drugs. The compound of the invention is disclosed as being effective as a gastrointestinal motor activity regulator, antimigraine, antipsychotic or antianxiety drug and for dementia or orthostatic hypotension.

U.S. Pat. No. 5,322,951 discloses certain 1-(2,3-dihydroindole)carbonyl intermediates useful for preparing 1-(2,3-dihydro)-1-carboxamide final products that possess 5-HT M-receptor antagonist activity.

U.S. Pat. No. 5,175,173 discloses carboxamides useful as antiemetic or antipsychotic agents.

U.S. Pat. No. 5,114,947 discloses method for alleviating anxiety using benzobicyclic carboxamides.

U.S. Pat. No. 5,063,231 discloses method of treatment of visceral pain.

U.S. Pat. No. 5,039,680 discloses 5-HT$_3$ antagonists in preventing or reducing dependency on dependency-inducing agents.

U.S. Pat. No. 5,001,133 discloses substituted benzoic acid heterocyclic amides and esters as being serotonin M antagonists.

U.S. Pat. No. 4,985,437 discloses the use of certain compounds which act as antagonists of 5-hydroxytryptamine (5-HT) at 5-HT$_3$ receptors for the treatment of cognitive disorders such as attentional and memory deficits and dementia states.

U.S. Pat. No. 4,983,600 discloses heterocyclic compounds useful as 5-HT$_3$ antagonists.

U.S. Pat. No. 4,973,594 discloses the use of compounds which act as antagonists of 5-hydroxytryptamine (5-HT) at 5-HT$_3$ receptors for the treatment of depression.

U.S. Pat. No. 4,937,247 discloses 1-acyl indazoles that are disclosed as having 5-HT$_3$ antagonist activity.

U.S. Pat. No. 4,935,511 discloses benzoxazine and benzoxazepin carboxamide 5-HT$_3$ antagonists properties including CNS, anti-emetic and gastric prokinetic activity and which are void of any significant D$_2$ receptor binding affinity.

U.S. Pat. No. 4,933,445 discloses heteroazabenzobicyclic carboxamide 5-HT$_3$ antagonists properties including CNS, anti-emetic and gastric prokinetic activity.

U.S. Pat. No. 4,921,982 discloses 5-halo-2,3-dihydro-2, 2-dimethylbenzofuran-7-carboxylic acids which are useful as intermediates for 5-HT$_3$ antagonists.

U.S. Pat. No. 4,920,227 discloses benzobicyclic carboxamide 5-HT$_3$ antagonists.

U.S. Pat. No. 4,920,219 discloses substituted saturated and unsaturated indole quinoline and benzazepine carboxamides and their valuable use as 5-HT$_3$ antagonists having CNS and gastric prokinetic activity void of any significant D$_2$ receptor binding properties.

U.S. Pat. No. 4,920,127 discloses substituted indoles and their use as 5-HT$_3$ receptor antagonists.

U.S. Pat. No. 4,910,193 discloses treatment of gastrointestinal disorders.

U.S. Pat. No. 4,882,327 discloses certain heterocyclic N-substituted carboxamides having 5-HT$_3$ receptor antagonist activity.

U.S. Pat. No. 4,863,919 discloses a method of enhancing memory or correcting memory deficiency with arylamido (and arylthioamido)-azabicycloalkanes.

U.S. Pat. No. 4,835,162 discloses agonists and antagonists to nicotine as smoking deterrents.

U.S. Pat. No. 4,822,795 discloses pharmaceutically useful esters and amides.

U.S. Pat. No. 4,803,199 discloses pharmaceutically useful heterocyclic acid esters and amides or alkylene bridged peperidines as serotonin M antagonists.

U.S. Pat. No. 4,798,829 discloses 1-azabicyclo[3.2.2] nonane derivatives having gastric motility enhancing activity and/or anti-emetic activity and/or 5-HT receptor antagonist activity.

U.S. Pat. No. 4,797,406 discloses amides and esters containing bridged piperidines and use as serotonin M antagonists.

U.S. Pat. No. 4,721,720 discloses a method of treating emesis, anxiety and/or irritable bowel syndrome.

U.S. Pat. No. 4,612,319 discloses bridged quinolizinidinylamides, compositions containing them and methods for their use.

U.S. Pat. No. 4,605,652 discloses a method of enhancing memory or correcting memory deficiency with arylamido (and arylthioamido)-azabicycloalkanes, and the pharmaceutically acceptable acid addition salts, hydrates and alcoholates thereof.

WO 01/76576 A1 discloses a pharmaceutical composition for treatment of acute, chorine pain and/or neuropathic pain migraines.

WO 01/60821 A1 discloses novel abiarylcarboxamides and their use in therapy, especially in the treatment of prophylaxis of psychotic and intellectual impairment conditions.

WO 01/36417 A1 discloses novel N-azabicyclo-amide derivatives and use in therapy, especially in the treatment of prophylaxis of psychotic disorders and intellectual impairment disorders.

WO 00/73431 A2 discloses two binding assays to directly measure the affinity and selectivity of compounds at the α7 nAChR and the 5-HT$_3$R. The combined use of these functional and binding assays may be used to identify compounds that are selective agonists of the α7 nAChR.

WO 97/35860 discloses novel benzimidazol derivatives having an affinity for the serotoninergic 5-HT$_3$/5-HT$_4$ receptors.

WO 96/33186 discloses substituted dihydrobenzofuran derivatives as 5-HT$_4$ agonists.

WO 95/27490 discloses serotonin antagonists (5-HT$_3$) for treating fibromyalgia.

WO 92/10494 discloses novel compounds having pharmacological activity, to a process for their preparation and their use as pharmaceuticals.

WO 91/17161 discloses isoquinoline amides and esters as 5-HT$_3$ receptor antagonists.

WO 91/09593 discloses 5-HT$_3$ antagonists for treatment of nausea, bradycardia or hypotension associated myocardial instability.

WO 90/14347 A as abstracted in chemical abstract 1991:143,158 discloses N-quinuclidinyl-indolecarboxamide derivatives as being antiemetics.

EP 512 350 A2 discloses 3-(indolyl-2-carboxamido) quinuclidines useful for treating diseases characterized by an excess or enhanced sensitivity to serotonin, e.g., psychosis, nausea, vomiting, dementia or other cognitive diseases, migraine, diabetes. The compound may be used to control anxiety, aggression, depression, and pain. The compounds are disclosed as serotonin 5-HT$_3$ antagonists.

EP 496 064 A1 discloses a process for the preparation of substituted benzofuran derivatives. The compounds are disclosed as being useful 5-HT$_3$ receptor antagonists.

EP 483 836 A1 discloses pyrazolo[1,5-a]pyridine-3-carboxylic acid derivatives, their preparation process, and serotonin receptor antagonists containing them as active ingredients.

EP 403 882 A2 discloses indole derivatives which have pharmacological activities such as 5-HT antagonism and the like.

EP 279 512 discloses the use of certain 5-HT3 receptro antagonists in the treatment of visceral pain.

DE 3810552 A1 discloses esters and amides of indolyl-, benzo[b]thiophenyl-, benzo[b]furancarboxylic acids or 4-amino-2 methoxy-benzoic acids with N-heterocyclic or N-heterobicyclic alcohols or amines. The compounds disclosed have activity against pain especially migraine, as an anti-arrhythmic for gastrointestinal disturbances, stomach disturbances, gastritis ulcer, gall bladder, spastic colon, Crohn's disease, ulcerative colitis, carcinoid syndrome, diarrhea of various types. The compounds are also disclosed as speeding stomach emptying, controlling gastro duodenal and gastro esophageal reflux, disturbances of esophageal motility, hiatal hernia, cardiac insufficiency, hypotonic stomach, paralytic ileus, manic depressive psychosis and other psychoses. The compounds are also disclosed as useful for stress related diseases, senility, and enhancement of nasal absorption of other agents, e.g., in the treatment of emesis.

In *Bioorg. & Med. Chem. Lett.* 11 (2001) 319–321, the 5-HT$_3$ antagonist tropisetron (ICS 205-930) is discussed as a potent and selective α7 nicotinic receptor partial agonist.

In *Behavioral Brain Res.*, 113 (2000) 169–181, it is discussed that the brain α7 nicotinic receptor may be an important therapeutic target for the treatment of Alzheimer's disease using DMXBA which is known as GTS-21.

In *Bioorg. & Med. Chem. Lett.* 9 (1999) 1895–1900, it is discussed the discovery of a highly potent, functionally-selective muscarinic M$_1$ agonist.

In *Bioorg. & Med. Chem. Lett.* 4 (1994) 695–698, it is discussed pyrazolo[1,5-a]pyridines and pyrazolo[1,5-b]pyridazines as 5-HT$_3$ antagonists.

In *Eur. J. med. Chem.* 34 (1999) 415–422, it is discussed benzimidazole-2-carboxylic acid amides and esters as a new structural class of 5-HT$_3$ ligands.

SUMMARY OF THE INVENTION

The present invention discloses compounds of the Formula I:

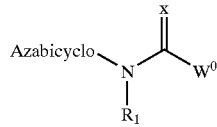

Formula I wherein X is O, or S;

Each R$_1$ is H, alkyl, cycloalkyl, halogenated alkyl, substituted phenyl, or substituted naphthyl;

Azabicyclo is

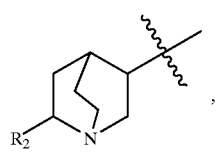

I

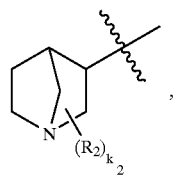

II

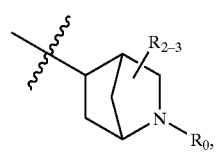

III

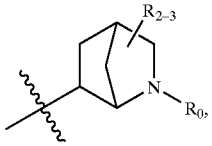

IV

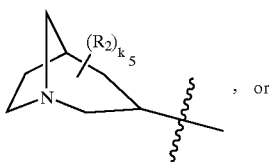

V

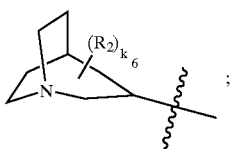

VI

R$_0$ is H, lower alkyl, substituted lower alkyl, or halogenated lower alkyl;

Each R$_2$ is independently alkyl, cycloalkyl, substituted phenyl, or substituted naphthyl, or R$_2$ is absent provided that k$_2$, k$_5$, or k$_6$ is 0;

k$_2$ is 0 or 1;

k$_5$ and k$_6$ are independently 0, 1, or 2;

R$_{2-3}$ is H, alkyl, halogenated alkyl, substituted alkyl, F, Cl, Br, or I;

W$^0$ is a bicyclic moiety and is

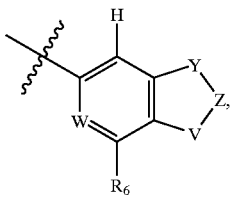

(a)

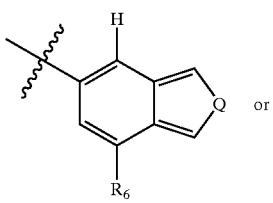

(b)

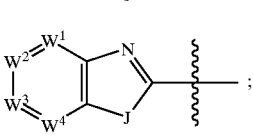

(c)

W is C(H) where
V---Z---Y is selected from O—C(R$_3$)=N, O—C(R$_5$)$_2$—N(R$_4$), O—C(R$_5$)$_2$—S, O—N=C(R$_5$), O—C(R$_5$)(R$_8$)—O, O—C(R$_5$)$_2$—O, C(R$_5$)$_2$—O—C(R$_5$)$_2$, S—C(R$_3$)=N, S—C(R$_5$)$_2$—N(R$_4$), S—N=C(R$_5$), N=C(R$_3$)—O, N=C(R$_3$)—S, N=C(R$_3$)—N(R$_4$), N(R$_4$)—N=C(R$_5$), N(R$_4$)—C(R$_5$)$_2$—O, N(R$_4$)—C(R$_5$)$_2$—S, N(R$_4$)—C(R$_5$)$_2$—N(R$_4$), C(R$_5$)$_2$—O—N(R$_4$), C(R$_5$)$_2$—S—C(R$_5$)$_2$, C(R$_5$)$_2$—N(R$_4$)—C(R$_5$)$_2$, C(R$_5$)$_2$—N(R$_4$)—O, C(R$_5$)$_2$—N(R$_4$)—S, C(R$_5$)=N—O, C(R$_5$)=N—S, C(R$_5$)=N—N(R$_4$), C(R$_5$)(R$_{17}$)—C(R$_3$)(R$_{17}$)—C(R$_5$)(R$_{17}$), or C(R$_5$)$_2$—C(R$_3$)(R$_5$)—C(R$_5$)$_2$;

W is N where

V---Z---Y is selected from O—C(R$_3$)=N, O—C(R$_5$)$_2$—N(R$_4$), O—C(R$_5$)$_2$—S, O—N=C(R$_5$) O—C(R$_5$)$_2$—O, S—C(R$_3$)=N, S—C(R$_5$)$_2$—N(R$_4$), S—N=C(R$_5$), N=C (R$_3$)—O, N=C(R$_3$)—S, N=C(R$_3$)—N(R$_4$), N(R$_4$)—N=C (R$_3$), N(R$_4$)—C(R$_5$)$_2$—O, N(R$_4$)—C(R$_5$)$_2$—S, N(R$_4$)—C (R$_5$)$_2$—N(R$_4$), C(R$_5$)$_2$—O—N(R$_4$), C(R$_5$)$_2$—N(R$_4$)—O, C(R$_5$)$_2$—N(R$_4$)—S, C(R$_5$)=N—O, C(R$_5$)=N—S, C(R$_3$) =N—N(R$_4$), C(R$_5$)=C(R$_3$)—O, C(R$_5$)=C(R$_3$)—S, C(R$_5$) =C(R$_5$)—N(R$_4$), C(R$_5$)=C(R$_5$)—C(R$_5$)$_2$, or C(R$_5$)$_2$—C (R$_3$)(R$_5$)—C(R$_5$)$_2$;

W$^1$, W$^2$, W$^3$, and W$^4$ are each independently N or C(R$_{21}$), provided that no more than two of W$^1$, W$^2$, W$^3$, and W$^4$ are N and further provided when more than two of W$^1$, W$^2$, W$^3$, and W$^4$ are C(R$_{21}$) that no more than two R$_{21}$ are other than H;

J is N(R$_{23}$), S, or O;

Q is N(R$_{19}$), O, or S;

Each R$_3$ is independently H, F, Cl, Br, I, alkyl, halogenated alkyl, substituted alkyl, cycloalkyl, lactam heterocycloalkyl, phenoxy, substituted phenoxy, R$_7$, R$_9$, —N(R$_4$)-aryl, —N(R$_4$)-halogenated phenyl, —N(R$_4$)-halogenated naphthyl, —O-halogenated phenyl, —O-substituted phenyl, —O-halogenated naphthyl, —O-substituted naphthyl, —S-halogenated phenyl, —S-substituted phenyl, —S-halogenated naphthyl, —S-substituted naphthyl, or alkyl substituted on the ω carbon with R$_{15}$ where said ω carbon is determined by counting the longest carbon chain of the alkyl moiety with the C-1 carbon being the carbon attached to the bicyclic moiety W$^0$ and the ω carbon being the carbon furthest, e.g., separated by the greatest number of carbon atoms in the chain, from said C-1 carbon;

Each R$_4$ is H, or alkyl;

Each R$_5$ is independently H, F, alkyl, substituted alkyl, halogenated alkyl, alkenyl, substituted alkenyl, halogenated alkenyl, alkynyl, substituted alkynyl, halogenated alkynyl, cycloalkyl, —C(O)NH$_2$, —CO$_2$R$_1$, or aryl;

R$_6$ is H, F, Br, I, Cl, —CN, —CF$_3$, —OR$_{16}$, —SR$_{16}$, or —N(R$_{16}$)$_2$;

R$_7$ is 5-membered heteroaromatic mono-cyclic moieties containing within the ring 1–3 heteroatoms independently selected from the group consisting of —O—, =N—, —N(R$_{19}$)—, and —S—, and having 0–1 substituent selected from R$_{20}$ and further having 0–3 substituents independently selected from F, Cl, Br, or I, or R$_7$ is 9-membered fused-ring moieties having a 6-membered ring fused to a 5-membered ring and having the formula

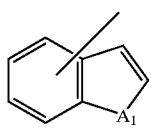

wherein A$_1$ is O, S, or NR$_{19}$,

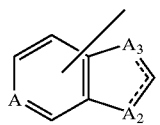

wherein A is CR$_{18}$ or N, A$_2$ and A$_3$ are independently selected from CR$_{18}$, C(R$_{18}$)$_2$, O, S, N, or NR$_{19}$, provided that both A$_2$ and A$_3$ are not simultaneously O, simultaneously S, or simultaneously O and S, or

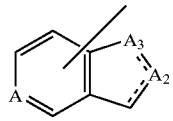

wherein A$_2$ and A$_3$ are independently selected from CR$_{18}$, C(R$_{18}$)$_2$, O, S, N, or NR$_{19}$, and A is CR$_{18}$ or N, each 9-membered fused-ring moiety having 0–1 substituent selected from R$_{20}$ and further having 0–3 substituent(s) independently selected from F, Cl, Br, or I, and having a bond directly or indirectly attached to the core molecule where valency allows in either the 6-membered or the 5-membered ring of the fused-ring moiety;

Each R$_8$ is independently F, alkyl, substituted alkyl, halogenated alkyl, alkenyl, substituted alkenyl, halogenated alkenyl, alkynyl, substituted alkynyl, halogenated alkynyl, cycloalkyl, —C(O)NH$_2$, —CO$_2$R$_1$, or aryl;

R$_9$ is 6-membered heteroaromatic mono-cyclic moieties containing within the ring 1–3 heteroatoms selected from =N— and having 0–1 substituent selected from R$_{20}$ and 0–3 substituent(s) independently selected from F, Cl, Br, or I, or R$_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from R$_{20}$ and 0–3 substituent(s) independently selected from F, Cl, Br, or I and having a bond directly or indirectly attached to the core molecule where valency allows;

Each R$_{10}$ is independently H, alkyl, cycloalkyl, heterocycloalkyl, alkyl substituted with 1 substituent selected from R$_{13}$, cycloalkyl substituted with 1 substituent selected from R$_{13}$, heterocycloalkyl substituted with 1 substituent selected from R$_{13}$, halogenated alkyl, halogenated cycloalkyl, halogenated heterocycloalkyl, phenyl, or substituted phenyl;

Each R$_{11}$ is independently H, alkyl, cycloalkyl, heterocycloalkyl, halogenated alkyl, halogenated cycloalkyl, or halogenated heterocycloalkyl;

R$_{13}$ is —OR$_{11}$, —SR$_{11}$, —N(R$_{11}$)$_2$, —C(O)R$_{11}$, —C(O) NR$_{11}$R$_{11}$, —CN, —CF$_3$, —NR$_{11}$C(O)R$_{11}$, —S(O)$_2$N(R$_{11}$)$_2$, —NR$_{11}$S(O)$_2$R$_{11}$, or —NO$_2$;

R$_{15}$ is aryl, R$_7$, or R$_9$;

R$_{16}$ is H, alkyl, substituted alkyl, cycloalkyl, halogenated alkyl, substituted phenyl, or substituted naphthyl;

One of R$_{17}$ is H, alkyl, substituted alkyl, halogenated alkyl, alkenyl, substituted alkenyl, halogenated alkenyl, alkynyl, substituted alkynyl, halogenated alkynyl, —CN, F, Br, Cl, I, —OR$_1$, —C(O)NH$_2$, —NHR$_1$, —SR$_1$, —CO$_2$R$_1$, aryl, R$_7$, or R$_9$, and each of the other two R$_{17}$ is independently alkyl, substituted alkyl, halogenated alkyl, alkenyl, substituted alkenyl, halogenated alkenyl, alkynyl, substituted alkynyl, halogenated alkynyl, —CN, F, Br, Cl, I, —OR$_1$, —C(O)NH$_2$, —NHR$_1$, —SR$_1$, —CO$_2$R$_1$, aryl, R$_7$, or R$_9$;

Each R$_{18}$ is independently selected from H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O) N(R$_{11}$)$_2$, —CN, —NR$_{11}$C(O)R$_{11}$, —S(O)$_2$N(R$_{11}$)$_2$, F, Cl, Br, or I, —NR$_{11}$S(O)$_2$R$_{11}$, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, and further provided that the fused-ring moiety has 0–3 substituent(s) selected from F, Cl, Br, or I;

$R_{19}$ is H, alkyl, halogenated alkyl, substituted alkyl, cycloalkyl, halogenated cycloalkyl, substituted cycloalkyl, phenyl, or phenyl having 1 substituent selected from $R_{20}$ and further having 0–3 substituents independently selected from F, Cl, Br, or I;

$R_{20}$ is alkyl, cycloalkyl, heterocycloalkyl, halogenated alkyl, halogenated cycloalkyl, halogenated heterocycloalkyl, —$OR_{11}$, —$SR_{11}$, —$NR_{11}R_{11}$, —$C(O)R_{11}$, —$C(O)NR_{11}R_{11}$, —CN, —$NR_{11}C(O)R_{11}$, —$S(O)_2NR_{11}R_{11}$, —$NR_{11}S(O)_2R_{11}$, —$NO_2$, alkyl substituted with 1–4 substituent(s) independently selected from F, Cl, Br, I, or $R_{13}$, cycloalkyl substituted with 1–4 substituent(s) independently selected from F, Cl, Br, I, or $R_{13}$, or heterocycloalkyl substituted with 1–4 substituent(s) independently selected from F, Cl, Br, I, or —$R_{13}$;

$R_{21}$ is H, F, Cl, Br, I, alkyl, substituted alkyl, halogenated alkyl, cycloalkyl, —CN, —$NR_{22}R_{22}$, —$OR_{22}$, or —$SR_{22}$;

Each $R_{22}$ is independently H, alkyl, substituted alkyl, cycloalkyl, halogenated alkyl, substituted cycloalkyl, heterocycloalkyl, or substituted heterocycloalkyl;

$R_{23}$ is alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, substituted phenyl, naphthyl, substituted naphthyl, $R_7$, or $R_9$;

or pharmaceutical composition, pharmaceutically acceptable salt, racemic mixture, or pure enantiomer thereof.

Embodiments of the invention may include one or more or combination of the following.

An embodiment of the present invention provides a use of a compound of Formula I for treating a disease or condition, wherein the diseases, disorders, and/or condition is any one or more or combination of the following: cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems in general and associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulemia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

In another aspect, the invention includes treating a mammal suffering from schizophrenia or psychosis by administering compounds of Formula I in conjunction with antipsychotic drugs (also called anti-psychotic agents). The compounds of the present invention and the antipsychotic drugs can be administered simultaneously or at separate intervals. When administered simultaneously the compounds of the present invention and the antipsychotic drugs can be incorporated into a single pharmaceutical composition. Alternatively, two separate compositions, i.e., one containing compounds of the present invention and the other containing antipsychotic drugs, can be administered simultaneously.

The present invention also includes the compounds of the present invention, pharmaceutical compositions containing the active compounds as the free base or as a pharmaceutically acceptable salt and a pharmaceutically acceptable carrier, and methods to treat the identified diseases.

A further embodiment of the present invention provides a method comprising administering a therapeutically effective amount of a compound of the present invention or a pharmaceutical composition contains said compound to the mammal.

The compound of Formula I, wherein X is O.
The compound of Formula I, where X is S.
The compound of Formula I, where Azabicyclo is any one or more of I, II, III, IV, V, or VI.

The compound of Formula I, where $W^0$ is any one or more of (a), (b), or (c). The compound of Formula I, where W is C(H), and where V---Z---Y is any one or more of the following: O—C($R_3$)=N, O—C($R_5$)$_2$—N($R_4$), O—C($R_5$)$_2$—S, O—N=C($R_5$), O—C($R_5$)($R_8$)—O, O—C($R_5$)$_2$—O, C($R_5$)$_2$—O—C($R_5$)$_2$, S—C($R_3$)=N, S—C($R_5$)$_2$—N($R_4$), S—N=C($R_5$), N=C($R_3$)—O, N=C($R_3$)—S, N=C($R_3$)—N($R_4$), N($R_4$)—N=C($R_5$), N($R_4$)—C($R_5$)$_2$—O, N($R_4$)—C($R_5$)$_2$—S, N($R_4$)—C($R_5$)$_2$—N($R_4$), C($R_5$)$_2$—O—N($R_4$), C($R_5$)$_2$—S—C($R_5$)$_2$, C($R_5$)$_2$—N($R_4$)—C($R_5$)$_2$, C($R_5$)$_2$—N($R_4$)—O, C($R_5$)$_2$—N($R_4$)—S, C($R_5$)=N—O, C($R_5$)=N—S, C($R_5$)=N—N($R_4$), C($R_5$)($R_{17}$)—C($R_3$)($R_{17}$)—C($R_5$)($R_{17}$), or C($R_5$)$_2$—C($R_3$)($R_5$)—C($R_5$)$_2$.

The compound of Formula I, where W is N, and where V---Z---Y is any one or more of the following: O—C($R_3$)=N, O—C($R_5$)$_2$—N($R_4$), O—C($R_5$)$_2$—S, O—N=C($R_5$) O—C($R_5$)$_2$—O, S—C($R_3$)=N, S—C($R_5$)$_2$—N($R_4$), S—N=C($R_5$), N=C($R_3$)—O, N=C($R_3$)—S, N=C($R_3$)—N($R_4$), N($R_4$)—N=C($R_5$), N($R_4$)—C($R_5$)$_2$—O, N($R_4$)—C($R_5$)$_2$—S, N($R_4$)—C($R_5$)$_2$—N($R_4$), C($R_5$)$_2$—O—N($R_4$), C($R_5$)$_2$—N($R_4$)—O, C($R_5$)$_2$—N($R_4$)—S, C($R_5$)=N—O, C($R_5$)=N—S, C($R_3$)=N—N($R_4$), C($R_5$)=C($R_3$)—O, C($R_5$)=C($R_3$)—S, C($R_5$)=C($R_5$)—N($R_4$), C($R_5$)=C($R_5$)—C($R_5$)$_2$, or C($R_5$)$_2$—C($R_3$)($R_5$)—C($R_5$)$_2$.

The compound of Formula I, where each $R_3$ is independently any one of the following: H, F, Cl, Br, I, alkyl, halogenated alkyl, substituted alkyl, cycloalkyl, lactam heterocycloalkyl, phenoxy, substituted phenoxy, $R_7$, $R_9$, —N($R_4$)-aryl, —N($R_4$)-halogenated phenyl, —N($R_4$)-halogenated naphthyl, —O-halogenated phenyl, —O-substituted phenyl, —O-halogenated naphthyl, —O-substituted naphthyl, —S-halogenated phenyl, —S-substituted phenyl, —S-halogenated naphthyl, —S-substituted naphthyl, or alkyl substituted on the ω carbon with $R_{15}$ where said ω carbon is determined by counting the longest carbon chain of the alkyl moiety with the C-1 carbon being the carbon attached to the bicyclic moiety $W^0$ and the ω carbon being the carbon furthest, e.g., separated by the greatest number of carbon atoms in the chain, from said C-1 carbon;

The compound of Formula I, where each $R_4$ is H. The compound of Formula I, where each $R_4$ is alkyl. The compound of Formula I, where one $R_4$ is alkyl and the other is H or alkyl.

The compound of Formula I, where each $R_5$ is independently H, F, alkyl, substituted alkyl, halogenated alkyl, alkenyl, substituted alkenyl, halogenated alkenyl, alkynyl, substituted alkynyl, halogenated alkynyl, cycloalkyl, —C(O)NH$_2$, —CO$_2$R$_1$, or aryl.

The compound of Formula I, where each R$_8$ is independently F, alkyl, substituted alkyl, halogenated alkyl, alkenyl, substituted alkenyl, halogenated alkenyl, alkynyl, substituted alkynyl, halogenated alkynyl, cycloalkyl, —C(O)NH$_2$, —CO$_2$R$_1$, or aryl.

The compound of Formula I, where one R$_{17}$ is H, alkyl, substituted alkyl, halogenated alkyl, alkenyl, substituted alkenyl, halogenated alkenyl, alkynyl, substituted alkynyl, halogenated alkynyl, —CN, F, Br, Cl, I, —CF$_3$, —OR$_1$, —C(O)NH$_2$, —NHR$_1$, —SR$_1$, —CO$_2$R$_1$, aryl, R$_7$, or R$_9$, and each of the other two R$_{17}$ is independently alkyl, substituted alkyl, halogenated alkyl, alkenyl, substituted alkenyl, halogenated alkenyl, alkynyl, substituted alkynyl, halogenated alkynyl, —CN, F, Br, Cl, I, —CF$_3$, —OR$_1$, —C(O)NH$_2$, —NHR$_1$, —SR$_1$, —CO$_2$R$_1$, aryl, R$_7$, or R$_9$.

Another group of compounds of Formula I includes compounds wherein W$^0$ includes any one or more of the following: 1,3-oxazolo[4,5-c]pyridin-6-yl, 1,3-oxazolo[5,4-c]pyridin-6-yl, 1,3-dioxolo[4,5-c]pyridin-6-yl, 1,3-benzoxazol-5-yl, 1,3-benzoxazol-6-yl, 1,2-benzisothiazol-5-yl, 1,2-benzisothiazol-6-yl, 1,3-thiazolo[4,5-c]pyridin-6-yl, 1,3-thiazolo[5,4-c]pyridin-6-yl, 1,3-benzothiazol-5-yl, 1,3-benzothiazol-6-yl, 1,3-benzodioxol-5-yl, 1H-benzimidazole-5-yl, 1H-indazol-5-yl, 1H-indazol-6-yl, indan-5-yl, 2-benzoisothiophen-5-yl, 2H-isoindole-5-yl, 2-benzofuran-5-yl, 1,3-benzothiazol-2-yl, or 1H-imidazo[4,5-c]pyridin-6-yl, any of which is optionally substituted with R$_3$, R$_4$, R$_5$, R$_8$, or R$_{17}$ as allowed by the definition of Formula I. One of ordinary skill in the art will recognize where the optional substitution is allowed by comparing the listed moieties with W$^0$.

Another embodiment includes compounds where W$^0$ includes any one or more of the following: 1,3-oxazolo[4,5-c]pyridin-6-yl, 1,3-oxazolo[5,4-c]pyridin-6-yl, 1,3-dioxolo[4,5-c]pyridin-6-yl, 1,3-benzoxazol-5-yl, 1,3-benzoxazol-6-yl, 1,2-benzisothiazol-5-yl, 1,2-benzisothiazol-6-yl, 1,3-thiazolo[4,5-c]pyridin-6-yl, 1,3-thiazolo[5,4-c]pyridin-6-yl, 1,3-benzothiazol-5-yl, 1,3-benzothiazol-6-yl, 1,3-benzodioxol-5-yl, 1H-benzimidazole-5-yl, 1H-indazol-5-yl, 1H-indazol-6-yl, indan-5-yl, 2-benzoisothiophen-5-yl, 2H-isoindole-5-yl, 2-benzofuran-5-yl, 1,3-benzothiazo2-yl, or 1H-imidazo[4,5-c]pyridin-6-yl, any of which is optionally substituted with lower cycloalkyl or lower alkyl optionally substituted with to 4 halogens, and further optionally substituted with up to 1 substituent selected from —OR$_{10}$, —N(R$_{10}$)$_2$, —C(O)NR$_{10}$R$_{10}$, —CN, —NR$_{10}$C(O)R$_{10}$, —NR$_{10}$S(O)$_2$R$_{10}$, wherein each R$_{10}$ is independently selected from lower alkyl or halogenated lower alkyl.

Another embodiment includes compounds where W$^0$ includes any one or more of the following: 1,3-oxazolo[4,5-c]pyridin-6-yl, 1,3-oxazolo[5,4-c]pyridin-6-yl, 1,3-dioxolo[4,5-c]pyridin-6-yl, 1,3-benzoxazol-5-yl, 1,3-benzoxazol-6-yl, 1,2-benzisothiazol-5-yl, 1,2-benzisothiazol-6-yl, 1,3-thiazolo[4,5-c]pyridin-6-yl, 1,3-thiazolo[5,4-c]pyridin-6-yl, 1,3-benzothiazol-5-yl, 1,3-benzothiazol-6-yl, 1,3-benzodioxol-5-yl, 1H-benzimidazole-5-yl, 1H-indazol-5-yl, 1H-indazol-6-yl, indan-5-yl, 2-benzoisothiophen-5-yl, 2H-isoindole-5-yl, 2-benzofuran-5-yl, 1,3-benzothiazol-2-yl, or 1H-imidazo[4,5-c]pyridin-6-yl, when Azabicyclo is II.

The compound of Formula I, where Q is N(R$_{19}$), O, or S.

Another embodiment includes compounds where W$^1$, W$^2$, W$^3$, and W$^4$ are each C(H) or N. Another embodiment includes compounds where W$^1$, W$^2$, W$^3$, and W$^4$ are each C(H). Another embodiment includes compounds where J is S.

The present invention also includes the compounds of the present invention, pharmaceutical compositions containing the active compounds, and methods to treat the identified diseases.

The present invention also includes a pharmaceutical composition comprising a compound of Formula I or a pharmaceutically acceptable salt thereof and a pharmaceutically acceptable excipient. The pharmaceutical composition is administered rectally, topically, orally, sublingually, or parenterally for a therapeutically effective interval. The pharmaceutical composition is administered to deliver a compound of the present invention in an amount of from about 0.001 to about 100 mg/kg of body weight of said mammal per day. The pharmaceutical composition is also administered to deliver a compound of the present invention in an amount of from about 0.1 to about 50 mg/kg of body weight of said mammal per day.

A pharmaceutical composition comprising a compound of Formula I or a pharmaceutically acceptable salt thereof, an anti-psychotic agent, and a pharmaceutically acceptable excipient. The pharmaceutical composition is administered to independently administer said compound and said agent rectally, topically, orally, sublingually, or parenterally for a therapeutically effective interval. The pharmaceutical composition is administered to deliver a compound of the present invention in an amount of from about 0.001 to about 100 mg/kg of body weight of said mammal per day. The pharmaceutical composition is also administered to deliver a compound of the present invention in an amount of from about 0.1 to about 50 mg/kg of body weight of said mammal per day.

The present invention also includes a use of a compound according to Formula I or pharmaceutically acceptable salt thereof for the preparation of a medicament for treating a disease or condition, wherein the mammal would receive symptomatic relief from the administration of a therapeutically effective amount of α7 nicotinic acetylcholine receptor agonist.

The present invention also includes a use of a compound according to Formula I or pharmaceutically acceptable salt thereof for the preparation of a medicament for treating a disease or condition, wherein the mammal would receive symptomatic relief from the administration of a therapeutically effective amount of α7 nicotinic acetylcholine receptor agonist, wherein the disease, or condition is any one or more or combination of the following: cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems in general and associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulimia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

The present invention also includes a method for treating a disease or condition in a mammal in need thereof, wherein the mammal would receive symptomatic relief from the administration of an α7 nicotinic acetylcholine receptor agonist comprising administering to the mammal a therapeutically effective amount of a compound according to Formula I or pharmaceutically acceptable salt thereof.

The present invention also includes a method for treating a disease or condition in a mammal in need thereof comprising administering to the mammal a therapeutically effective amount of a compound according to Formula I or pharmaceutically acceptable salt thereof, wherein the disease or condition is any one or more or combination of the following: cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems in general and associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulemia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

The compounds of Formula I (Azabicyclo is I) have optically active centers on the quinuclidine ring. The compounds of the present invention include quinuclidines with the 3R configuration and also includes racemic mixtures and compositions of varying degrees of streochemical purities. For example, and not by limitation, compounds of Formula I include compounds with stereospecificity including:

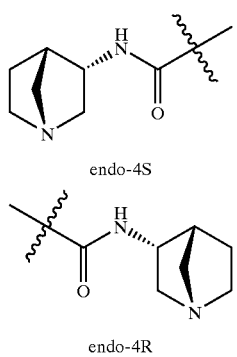

The compounds of Formula I (Azabicyclo is II) have optically active center(s) on the [2.2.1] azabicyclic ring at C3 and C4. The scope of this invention includes racemic mixtures and the separate stereoisomers of Formula I being endo-4S, endo-4R, exo-4S, exo-4R:

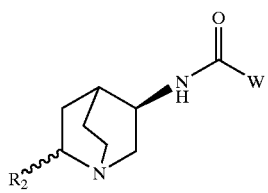

endo-4S endo-4R

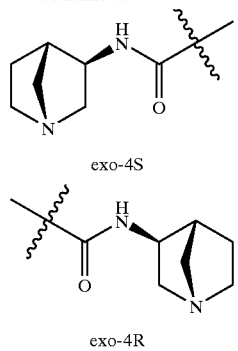

exo-4S exo-4R

The endo isomer is the isomer where the non-hydrogen substituent at C3 of the [2.2.1] azabicyclic compound is projected toward the larger of the two remaining bridges. The exo isomer is the isomer where the non-hydrogen substituent at C3 of the [2.2.1] azabicyclic compound is projected toward the smaller of the two remaining bridges. Thus, there can be four separate isomers: exo-4(R), exo-4(S), endo-4(R), and endo-4(S).

The compounds of Formula I (Azabicyclo III) have optically active center(s) on the [2.2.1] azabicyclic ring at C1, C4 and C5. The scope of this invention includes racemic mixtures and the separate stereoisomers of Formula I being (1R,4R,5S), (1R,4R,5R), (1S,4S,5R), (1S,4S,5S):

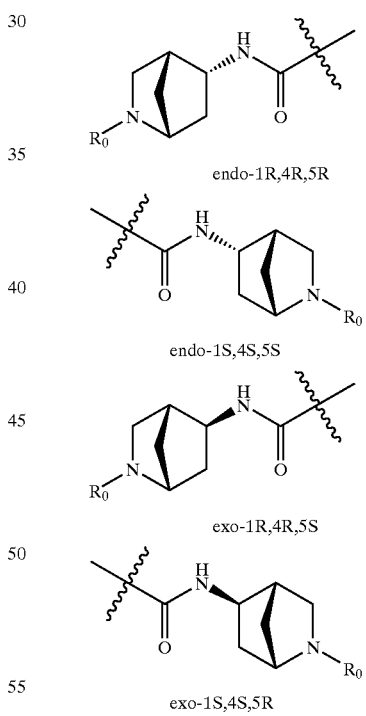

endo-1R,4R,5R endo-1S,4S,5S exo-1R,4R,5S exo-1S,4S,5R

The endo isomer is the isomer where the non-hydrogen substituent at C5 of the [2.2.1] azabicyclic compound is projected toward the larger of the two remaining bridges. The exo isomer is the isomer where the non-hydrogen substituent at C5 of the [2.2.1] azabicyclic compound is projected toward the smaller of the two remaining bridges. Thus, there can be four separate isomers: exo-(1R,4R,5S), exo-(1S,4S,5R), endo-(1S,4S,5S), endo-(1R,4R,5R).

The compounds of Formula I (Azabicyclo IV) have optically active center(s) on the [2.2.1] azabicyclic ring at C1, C4 and C6. The scope of this invention includes racemic mixtures and the separate stereoisomers of Formula I being exo-(1S,4R,6S), exo-(1R,4S,6R), endo-(1S,4R,6R), and endo-(1R,4S,6S):

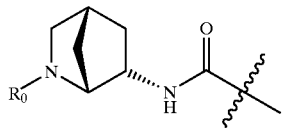

endo-1R,4S,6S

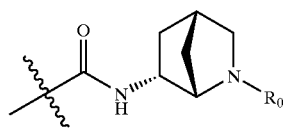

endo-1S,4R,6R

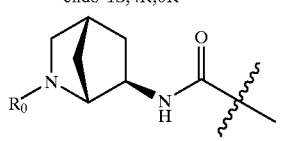

exo-1R,4S,6R

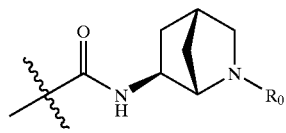

exo-1S,4R,6S

The endo isomer is the isomer where the non-hydrogen substituent at C6 of the [2.2.1] azabicyclic compound is projected toward the larger of the two remaining bridges. The exo isomer is the isomer where the non-hydrogen substituent at C6 of the [2.2.1] azabicyclic compound is projected toward the smaller of the two remaining bridges. Thus, there can be four separate isomers: exo-(1S,4R,6S), exo-(1R,4S,6R), endo-(1S,4R,6R), and endo-(1R,4S,6S).

The compounds of Formula I (Azabicyclo is V) have optically active center(s) on the [3.2.1] azabicyclic ring at C3 and C5. The scope of this invention includes racemic mixtures and the separate stereoisomers of Formula I being endo-3S, 5R, endo-3R, 5S, exo-3R, 5R, exo-3S, 5S:

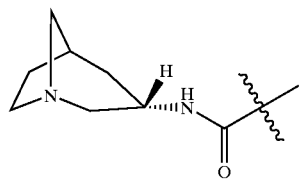

endo-3S,5R

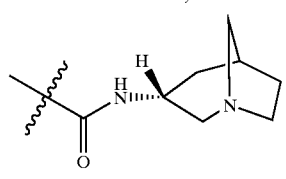

endo-3R,5S

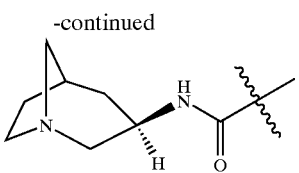

exo-3R,5R

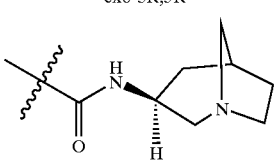

exo-3S,5S

The compounds of Formula I (Azabicyclo is VI) have optically active centers on the [3.2.2] azabicyclic ring with one center being at C3 when $R_2$ is absent. The scope of this invention includes racemic mixtures and the separate stereoisomers of Formula I being 3(S) and 3(R):

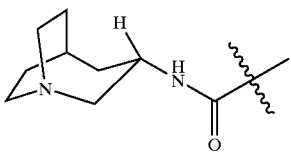

3(S)

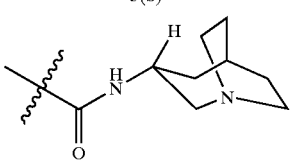

3(R)

The compounds of the present invention having the specified stereochemistry have different levels of activity and that for a given set of values for the variable substituents one isomer may be preferred over the other isomers. Although it is desirable that the stereochemical purity be as high as possible, absolute purity is not required. This invention involves racemic mixtures and compositions of varying degrees of streochemical purities when the Azabicyclo is substituted with only the amide/thioamide or is substituted with substituents in addition to the amide/thioamide, e.g., k is 1 or 2. This invention involves racemic mixtures and compositions of varying degrees of stereochemical purities. When racemic mixtures and compositions are referenced, it means racemic mixtures and compositions of varying degree of stereochemical purities. It is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions. Naming a specific isomer includes racemic mixtures thereof within the scope of this invention. Therefore, naming N-(exo-4(S)-1-azabicyclo[2.2.1]hept-3-yl)-1,3-benzoxazole-5-carboxamide, includes N-(exo-4(rac)-1-azabicyclo[2.2.1]hept-3-yl)-1,3-benzoxazole-5-carboxamide; N-(3(rac),4(S)-1-azabicyclo[2.2.1]hept-3-yl)-1,3-benzoxazole-5-carboxamide, and N-(1-azabicyclo[2.2.1]hept-3-yl)-1,3-benzoxazole-5-carboxamide.

Stereoselective syntheses and/or subjecting the reaction product to appropriate purification steps produces substantially optically pure materials. Suitable stereoselective synthetic procedures for producing optically pure materials are well known in the art, as are procedures for purifying racemic mixtures into optically pure fractions.

Another embodiment of the compounds of Formula I includes any one or more or combination of the following configurations for compounds:

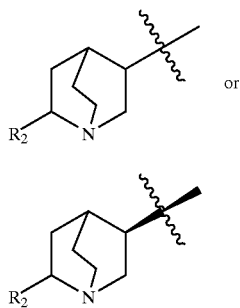

where (i) the compound is a racemic mixture, or (ii) the compound has the R stereochemistry at C-3 as discussed herein and stereochemistry is unspecified at C-6.

Another embodiment of compounds of Formula I includes any one or more or combination of the following configurations for compounds:

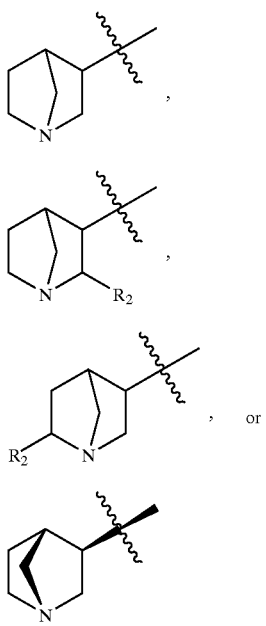

where (i) $k_2$ is 0 ($R_2$ is absent);

(ii) $R_2$ has any definition discussed herein;

(iii) $R_2$ has any definition discussed herein; or (iv) the 2.2.1 moiety has the exo-4(S) stereochemistry as discussed herein.

Another embodiment of compounds of Formula I includes any one or more or combination of the following configurations for compounds:

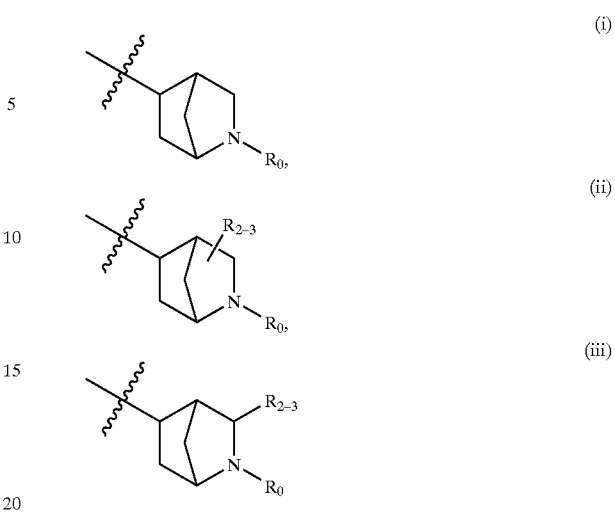

where (i) $R_{2-3}$ is H;

(ii) $R_{2-3}$ is F, Cl, Br, I, alkyl, halogenated alkyl, substituted alkyl, or substituted phenyl or substituted naphthyl; or (iii) $R_{2-3}$ is alkyl, halogenated alkyl, substituted alkyl, or substituted phenyl or substituted naphthyl.

Another embodiment of compounds of Formula I includes any one or more or combination of the following configurations for compounds:

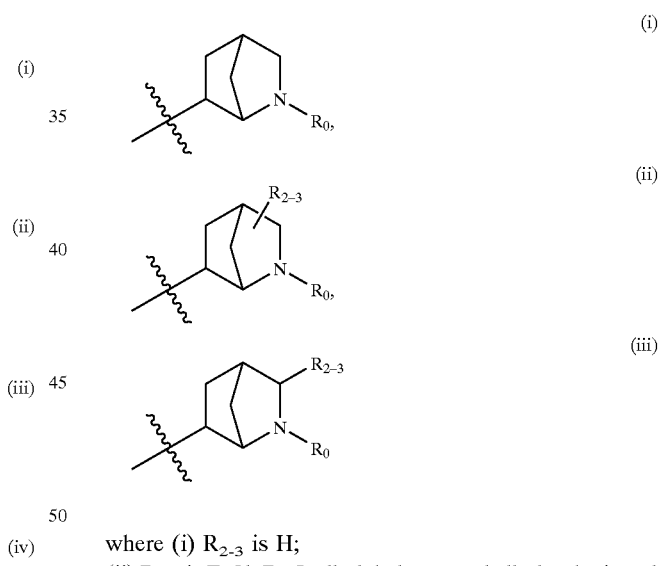

where (i) $R_{2-3}$ is H;

(ii) $R_{2-3}$ is F, Cl, Br, I, alkyl, halogenated alkyl, substituted alkyl, or substituted phenyl or substituted naphthyl; or (iii) $R_{2-3}$ is alkyl, halogenated alkyl, substituted alkyl, or substituted phenyl or substituted naphthyl.

Another embodiment of compounds of Formula I includes any one or more or combination of the following configurations for compounds:

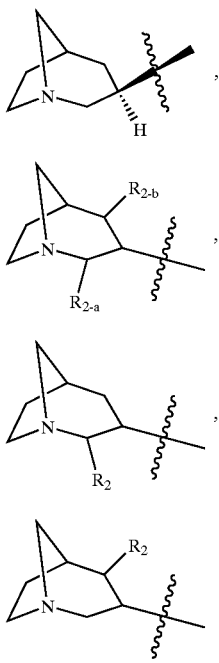

where (i) $k_5$ is 0 ($R_2$ is absent);

(ii) $R_2$ is absent and where the Azabicyclo has the stereochemistry of 3R, 5R;

(iii) $k_5$ is 2, where $R_{2-a}$ is alkyl, cycloalkyl, substituted phenyl, or substituted naphthyl, and where $R_{2-b}$ is alkyl, cycloalkyl, substituted phenyl, or substituted naphthyl;

(iv) $k_5$ is 1, where $R_2$ is alkyl, cycloalkyl, substituted phenyl, or substituted naphthyl; or (v) $k_5$ is 1, where $R_2$ is alkyl, cycloalkyl, substituted phenyl, or substituted naphthyl.

Another embodiment of compounds of Formula I includes any one or more or combination of the following configurations for compounds:

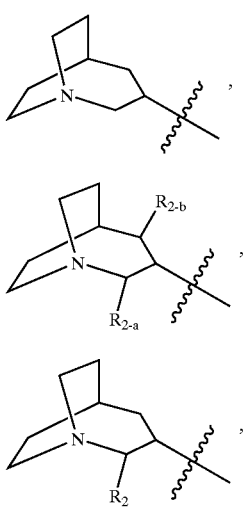

where (i) $k_6$ is 0 ($R_2$ is absent);

(ii) $k_6$ is 2, where each $R_{2-a}$ is alkyl, cycloalkyl, substituted phenyl, or substituted naphthyl, and where each $R_{2-b}$ is alkyl, cycloalkyl, substituted phenyl, or substituted naphthyl;

(iii) $k_6$ is 1, where $R_2$ is alkyl, cycloalkyl, substituted phenyl, or substituted naphthyl; or (iv) $k_6$ is 1, where $R_2$ is alkyl, cycloalkyl, substituted phenyl, or substituted naphthyl.

The compound of Formula I, where the compound is any one or more or combination of the following as the free base, or pharmaceutically acceptable salt thereof as a pure enantiomer or racemic mixture thereof:

N-(exo-4(S)-1-azabicyclo[2.2.1]hept-3-yl)-1,3-benzoxazole-5-carboxamide;

N-(exo-4(S)-1-azabicyclo[2.2.1]hept-3-yl)-1,3-benzothiazole-6-carboxamide;

N-[(exo-4S)-1-azabicyclo[2.2.1]hept-3-yl]-indane-5-carboxamide;

N-(exo-4(S)-1-azabicyclo[2.2.1]hept-3-yl)-1,3-benzodioxole-5-carboxamide;

N-[(exo-4S)-1-azabicyclo[2.2.1]hept-3-yl]-1H-indazole-5-carboxamide;

N-[(exo-4S)-1-azabicyclo[2.2.1]hept-3-yl]-1H-indazole-6-carboxamide;

N-[(exo-4S)-1-azabicyclo[2.2.1]hept-3-yl]-1,3-dioxolo[4,5-c]pyridine-6-carboxamide;

or N-[(3R,5R)-1-azabicyclo[3.2.1]oct-3-yl]-1,3-benzothiazole-6-carboxamide.

The compound of Formula I, where the compound is any one or more or combination of the following as the free base, or pharmaceutically acceptable salt thereof as a pure enantiomer or racemic mixture thereof:

N-(1-(6-methyl)-azabicyclo[2.2.2]oct-3-yl)-1,3-benzoxazole-5-carboxamide;

N-(1-(6-methyl)-azabicyclo[2.2.2]oct-3-yl)-2-methyl-1,3-benzoxazole-5-carboxamide;

N-(1-(6-methyl)-azabicyclo[2.2.2]oct-3-yl)-1,3-benzoxazole-6-carboxamide;

N-(1-(6-methyl)-azabicyclo[2.2.2]oct-3-yl)-2-methyl-1,3-benzoxazole-6-carboxamide;

N-(1-(6-methyl)-azabicyclo[2.2.2]oct-3-yl)-1,3-benzothiazole-6-carboxamide;

N-(1-(6-methyl)-azabicyclo[2.2.2]oct-3-yl)indane-5-carboxamide;

N-(1-(6-methyl)-azabicyclo[2.2.2]oct-3-yl)-1,3-benzodioxole-5-carboxamide;

N-(1-(6-methyl)-azabicyclo[2.2.2]oct-3-yl)-1,3-oxazolo[5,4-c]pyridine-6-carboxamide;

N-(1-(6-methyl)-azabicyclo[2.2.2]oct-3-yl)-1H-indazole-5-carboxamide;

N-(1-(6-methyl)-azabicyclo[2.2.2]oct-3-yl)-1H-indazole-6-carboxamide;

N-(1-(6-methyl)-azabicyclo[2.2.2]oct-3-yl)-1,3-dioxolo[4,5-c]pyridine-6-carboxamide;

N-(exo-4(S)-1-azabicyclo[2.2.1]hept-3-yl)-2-methyl-1,3-benzoxazole-5-carboxamide;

N-(exo-4(S)-1-azabicyclo[2.2.1]hept-3-yl)-1,3-benzoxazole-6-carboxamide;

N-(exo-4(S)-1-azabicyclo[2.2.1]hept-3-yl)-2-methyl-1,3-benzoxazole-6-carboxamide;
N-[exo-4(S)-1-azabicyclo[2.2.1]hept-3-yl]-1,3-oxazolo[5,4-c]pyridine-6-carboxamide;
N-(exo-4(S)-1-(6-methyl)-azabicyclo[2.2.1]hept-3-yl)-1,3-benzoxazole-5-carboxamide;
N-(exo-4(S)-1-(6-methyl)-azabicyclo[2.2.1]hept-3-yl)-2-methyl-1,3-benzoxazole-5-carboxamide;
N-(exo-4(S)-1-(6-methyl)-azabicyclo[2.2.1]hept-3-yl)-1,3-benzoxazole-6-carboxamide;
N-(exo-4(S)-1-(6-methyl)-azabicyclo[2.2.1]hept-3-yl)-2-methyl-1,3-benzoxazole-6-carboxamide;
N-(exo-4(S)-1-(6-methyl)-azabicyclo[2.2.1]hept-3-yl)-1,3-benzothiazole-6-carboxamide;
N-(exo-4(S)-1-(6-methyl)-azabicyclo[2.2.1]hept-3-yl)indane-5-carboxamide;
N-(exo-4(S)-1-(6-methyl)-azabicyclo[2.2.1]hept-3-yl)-1,3-benzodioxole-5-carboxamide;
N-(exo-4(S)-1-(6-methyl)-azabicyclo[2.2.1]hept-3-yl)-1,3-oxazolo[5,4-c]pyridine-6-carboxamide;
N-(exo-4(S)-1-(6-methyl)-azabicyclo[2.2.1]hept-3-yl)-1H-indazole-5-carboxamide;
N-(exo-4(S)-1-(6-methyl)-azabicyclo[2.2.1]hept-3-yl)-1H-indazole-6-carboxamide;
N-(exo-4(S)-1-(6-methyl)-azabicyclo[2.2.1]hept-3-yl)-1,3-dioxolo[4,5-c]pyridine-6-carboxamide;
N-[(3R,5R)-1-azabicyclo[3.2.1]oct-3-yl]-1,3-benzoxazole-5-carboxamide;
N-[(3R,5R)-1-azabicyclo[3.2.1]oct-3-yl]-2-methyl-1,3-benzoxazole-5-carboxamide;
N-[(3R,5R)-1-azabicyclo[3.2.1]oct-3-yl]-1,3-benzoxazole-6-carboxamide;
N-[(3R,5R)-1-azabicyclo[3.2.1]oct-3-yl]-2-methyl-1,3-benzoxazole-6-carboxamide;
N-[(3R,5R)-1-azabicyclo[3.2.1]oct-3-yl]indane-5-carboxamide;
N-[(3R,5R)-1-azabicyclo[3.2.1]oct-3-yl]-1,3-benzodioxole-5-carboxamide;
N-[(3R,5R)-1-azabicyclo[3.2.1]oct-3-yl]-1,3-oxazolo[5,4-c]pyridine-6-carboxamide;
N-[(3R,5R)-1-azabicyclo[3.2.1]oct-3-yl]-1H-indazole-5-carboxamide;
N-[(3R,5R)-1-azabicyclo[3.2.1]oct-3-yl]-1H-indazole-6-carboxamide;
N-[(3R,5R)-1-azabicyclo[3.2.1]oct-3-yl]-1,3-dioxolo[4,5-c]pyridine-6-carboxamide;
N-((3R)-1-azabicyclo[3.2.2]nonan-3-yl)-1,3-benzoxazole-5-carboxamide;
N-((3R)-1-azabicyclo[3.2.2]nonan-3-yl)-1,3-benzothiazole-6-carboxamide;
N-((3R)-1-azabicyclo[3.2.2]nonan-3-yl)indane-5-carboxamide;
N-((3R)-1-azabicyclo[3.2.2]nonan-3-yl)-1,3-benzodioxole-5-carboxamide;
N-[(3R)-1-azabicyclo[3.2.2]nonan-3-yl]-1H-indazole-6-carboxamide; or
N-[(3R)-1-azabicyclo[3.2.2]nonan-3-yl]-1,3-dioxolo[4,5-c]pyridine-6-carboxamide.

The compound of Formula I, where the compound is any one or more or combination of the following as the free base, or pharmaceutally acceptable salt thereof as a pure enantiomer or racemic mixture thereof:
N-[exo-4(S)-1-azabicyclo[2.2.1]hept-3-yl]-1,2-benzisothiazole-6-carboxamide;
N-[exo-4(S)-1-azabicyclo[2.2.1]hept-3-yl]-1,2-benzisothiazole-5-carboxamide;
N-[(3R,5R)-1-azabicyclo[3.2.1]oct-3-yl]-1H-indazole-5-carboxamide;
N-[(3R,5R)-1-azabicyclo[3.2.1]oct-3-yl]-3-methyl-1H-indazole-6-carboxamide;
N-[(3R,5R)-1-azabicyclo[3.2.1]oct-3-yl]-3-methyl-1H-indazole-5-carboxamide;
N-[(3R,5R)-1-azabicyclo[3.2.1]oct-3-yl]-3-ethyl-1H-indazole-6-carboxamide;
N-[(3R,5R)-1-azabicyclo[3.2.1]oct-3-yl]-3-ethyl-1H-indazole-5-carboxamide;
N-[(3R,5R)-1-azabicyclo[3.2.1]oct-3-yl]-1,2-benzisothiazole-6-carboxamide;
N-[(3R,5R)-1-azabicyclo[3.2.1]oct-3-yl]-1,2-benzisothiazole-5-carboxamide;
N-[(3R,5R)-1-azabicyclo[3.2.1]oct-3-yl]-3-ethyl-1,2-benzisothiazole-6-carboxamidide;
N-[(3R,5R)-1-azabicyclo[3.2.1]oct-3-yl]-3-ethyl-1,2-benzisothiazole-5-carboxamide;
N-[(3R,5R)-1-azabicyclo[3.2.1]oct-3-yl]-3-methyl-1,2-benzisothiazole-6-carboxamide;
N-[(3R,5R)-1-azabicyclo[3.2.1]oct-3-yl]-3-methyl-1,2-benzisothiazole-5-carboxamide;
N-[(3R,5R)-1-azabicyclo[3.2.1]oct-3-yl]-2-cyclopropyl-1,3-benzoxazole-6-carboxamide;
N-[(3R,5R)-1-azabicyclo[3.2.1]oct-3-yl]-2-cyclopropyl-1,3-benzoxazole-5-carboxamide;
N-[(3R,5R)-1-azabicyclo[3.2.1]oct-3-yl]-2-cyclopropyl-1,3-benzothiazole-6-carboxamide;
N-[(3R,5R)-1-azabicyclo[3.2.1]oct-3-yl]-2-cyclopropyl-1,3-benzothiazole-5-carboxamide;
N-[(3R,5R)-1-azabicyclo[3.2.1]oct-3-yl]-2-methyl-1,3-benzothiazole-6-carboxamide;
N-[(3R,5R)-1-azabicyclo[3.2.1]oct-3-yl]-2-methyl-1,3-benzothiazole-5-carboxamide;
N-[(3R,5R)-1-azabicyclo[3.2.1]oct-3-yl]-2-ethyl-1,3-benzothiazole-6-carboxamide;
N-[(3R,5R)-1-azabicyclo[3.2.1]oct-3-yl]-2-ethyl-1,3-benzothiazole-5-carboxamide;
N-[(3R,5R)-1-azabicyclo[3.2.1]oct-3-yl]-2-methyl-1,3-benzodioxole-5-carboxamide;
N-[(3R,5R)-1-azabicyclo[3.2.1]oct-3-yl]-2-ethyl-1,3-benzodioxole-5-carboxamide;
N-[(3R,5R)-1-azabicyclo[3.2.1]oct-3-yl]-2,2-dimethyl-1,3-benzodioxole-5-carboxamide;
N-[(3R,5R)-1-azabicyclo[3.2.1]oct-3-yl]-1H-benzimidazole-5-carboxamide;
N-[(3R,5R)-1-azabicyclo[3.2.1]oct-3-yl]-1,3-thiazolo[5,4-c]pyridine-6-carboxamide;
N-[(3R,5R)-1-azabicyclo[3.2.1]oct-3-yl]-1,3-thiazolo[4,5-c]pyridine-6-carboxamide;
N-[(3R,5R)-1-azabicyclo[3.2.1]oct-3-yl]-1,3-dioxolo[4,5-c]pyridine-6-carboxamide;
or N-[(3R,5R)-1-azabicyclo[3.2.1]oct-3-yl]-1,3-oxazolo[4,5-c]pyridine-6-carboxamide.

The compound of Formula I, where the compound is any one or more or combination of the following as the free base, or pharmaceutally acceptable salt thereof as a pure enantiomer or racemic mixture thereof:
N-(1-(6-methyl)-azabicyclo[2.2.2]oct-3-yl)-2-benzoisothiophene-5-benzamide;
N-[exo-4(S)-1-azabicyclo[2.2.1]hept-3-yl]-2-benzoisothiophene-5-benzamide;
N-(exo-4(S)-1-(6-methyl)-azabicyclo[2.2.1]hept-3-yl)-2-benzoisothiophene-5-benzamide;
N-[(3R,5R)-1-azabicyclo[3.2.1]oct-3-yl]-2-benzoisothiophene-5-benzamide;
N-[exo-4(S)-1-azabicyclo[2.2.1]hept-3-yl]-2-benzofuran-5-carboxamide;
N-[exo-4(S)-1-azabicyclo[2.2.1]hept-3-yl]-2H-isoindole-5-carboxamide;

N-[(3R,5R)-1-azabicyclo[3.2.1]oct-3-yl]-2-benzofuran-5-carboxamide; or N-[(3R,5R)-1-azabicyclo[3.2.1]oct-3-yl]-2H-isoindole-5-carboxamide;

The compound of Formula I, where the compound is any one or more or combination of the following as the free base, or pharmaceutally acceptable salt thereof as a pure enantiomer or racemic mixture thereof:

N-(2-azabicyclo[2.2.1]hept-5-yl)-1,3-benzoxazole-5-carboxamide;
N-(2-azabicyclo[2.2.1]hept-5-yl)-2-methyl-1,3-benzoxazole-5-carboxamide;
N-(2-azabicyclo[2.2.1]hept-5-yl)-1,3-benzoxazole-6-carboxamide;
N-(2-azabicyclo[2.2.1]hept-5-yl)-2-methyl-1,3-benzoxazole-6-carboxamide;
N-(2-azabicyclo[2.2.1]hept-5-yl)-1,3-benzothiazole-6-carboxamide;
N-(2-azabicyclo[2.2.1]hept-5-yl)indane-5-carboxamide;
N-(2-azabicyclo[2.2.1]hept-5-yl)-1,3-benzodioxole-5-carboxamide;
N-(2-azabicyclo[2.2.1]hept-5-yl)-1,3-oxazolo[5,4-c]pyridine-6-carboxamide;
N-(2-azabicyclo[2.2.1]hept-5-yl)-1H-indazole-5-carboxamide;
N-(2-azabicyclo[2.2.1]hept-5-yl)-1H-indazole-6-carboxamide;
N-(2-azabicyclo[2.2.1]hept-5-yl)-1,3-dioxolo[4,5-c]pyridine-6-carboxamide;
N-(2-azabicyclo[2.2.1]hept-6-yl))-1,3-benzoxazole-5-carboxamide;
N-(2-azabicyclo[2.2.1]hept-6-yl))-2-methyl-1,3-benzoxazole-5-carboxamide;
N-(2-azabicyclo[2.2.1]hept-6-yl))-1,3-benzoxazole-6-carboxamide;
N-(2-azabicyclo[2.2.1]hept-6-yl))-2-methyl-1,3-benzoxazole-6-carboxamide;
N-(2-azabicyclo[2.2.1]hept-6-yl))-1,3-benzothiazole-6-carboxamide;
N-(2-azabicyclo[2.2.1]hept-6-yl))indane-5-carboxamide;
N-(2-azabicyclo[2.2.1]hept-6-yl))-1,3-benzodioxole-5-carboxamide;
N-(2-azabicyclo[2.2.1]hept-6-yl))-1,3-oxazolo[5,4-c]pyridine-6-carboxamide;
N-(2-azabicyclo[2.2.1]hept-6-yl))-1H-indazole-5-carboxamide;
N-(2-azabicyclo[2.2.1]hept-6-yl))-1H-indazole-6-carboxamide; or
N-(2-azabicyclo[2.2.1]hept-6-yl))-1,3-dioxolo[4,5-c]pyridine-6-carboxamide.

The compound of Formula I, where the compound is any one or more or combination of the following as the free base, or pharmaceutally acceptable salt thereof as a pure enantiomer or racemic mixture thereof:

N-(2-azabicyclo[2.2.1]hept-5-yl)-2-benzoisothiophene-5-benzamide; or
N-(2-azabicyclo[2.2.1]hept-6-yl))-2-benzoisothiophene-5-benzamide.

The compound of Formula I, where the compound is any one or more or combination of the following as the free base, or pharmaceutally acceptable salt thereof as a pure enantiomer or racemic mixture thereof:

N-(1-(6-methyl)-azabicyclo[2.2.2]oct-3-yl)-1,3-benzothiazole-2-carboxamide;
N-[exo-4(S)-1-azabicyclo[2.2.1]hept-3-yl]-1,3-benzothiazole-2-carboxamide;
N-(exo-4(S)-1-(6-methyl)-azabicyclo[2.2.1]hept-3-yl)-1,3-benzothiazole-2-carboxamide;
N-[(3R,5R)-1-azabicyclo[3.2.1]oct-3-yl]-1,3-benzothiazole-2-carboxamide;
N-[(3R,5R)-1-azabicyclo[3.2.1]oct-3-yl]-1H-imidazo[4,5-c]pyridine-6-carboxamide;
N-[(3R)-1-azabicyclo[3.2.2]nonan-3-yl]-1,3-benzothiazole-2-carboxamide;
N-(2-azabicyclo[2.2.1]hept-5-yl)-1,3-benzothiazole-2-carboxamide; or
N-(2-azabicyclo[2.2.1]hept-6-yl))-1,3-benzothiazole-2-carboxamide.

Further aspects and embodiments of the invention may become apparent to those skilled in the art from a review of the following detailed description, taken in conjunction with the examples and the appended claims. While the invention is susceptible of embodiments in various forms, described hereafter are specific embodiments of the invention with the understanding that the present disclosure is intended as illustrative, and is not intended to limit the invention to the specific embodiments described herein.

DETAILED DESCRIPTION OF THE INVENTION

Surprisingly, we have found that compounds of Formula I:

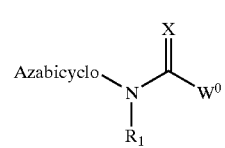

Formula I wherein X is O, or S;

Each $R_1$ is H, alkyl, cycloalkyl, halogenated alkyl, substituted phenyl, or substituted naphthyl;

Azabicyclo is

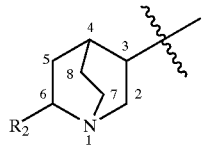

I

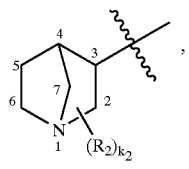

II

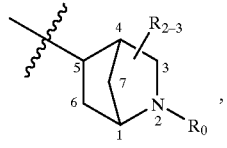

III

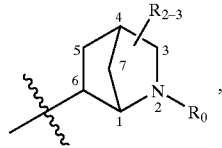

IV

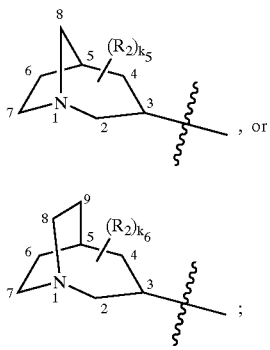

, or

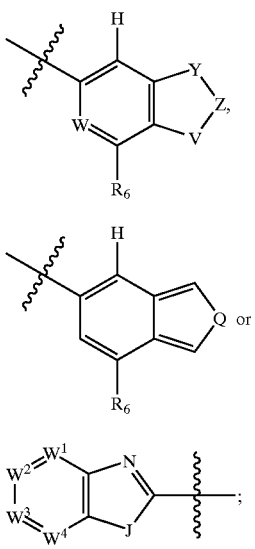

;

$R_0$ is H, lower alkyl, substituted lower alkyl, or halogenated lower alkyl;

Each $R_2$ is independently alkyl, cycloalkyl, substituted phenyl, or substituted naphthyl, or $R_2$ is absent provided that $k_2$, $k_5$, or $k_6$ is 0;

$k_2$ is 0 or 1;

$k_5$ and $k_6$ are independently 0, 1, or 2;

$R_{2-3}$ is H, alkyl, halogenated alkyl, substituted alkyl, F, Cl, Br, or I;

$W^0$ is a bicyclic moiety and is (a)

(b)

(c)

W is C(H) where

V---Z---Y is selected from O—C(R$_3$)=N, O—C(R$_5$)$_2$—N(R$_4$), O—C(R$_5$)$_2$—S, O—N=C(R$_5$), O—C(R$_5$)(R$_8$)—O, O—C(R$_5$)$_2$—O, C(R$_5$)$_2$—O—C(R$_5$)$_2$, S—C(R$_3$)=N, S—C(R$_5$)$_2$—N(R$_4$), S—N=C(R$_5$), N=C(R$_3$)—O, N=C(R$_3$)—S, N=C(R$_3$)—N(R$_4$), N(R$_4$)—N=C(R$_5$), N(R$_4$)—C(R$_5$)$_2$—O, N(R$_4$)—C(R$_5$)$_2$—S, N(R$_4$)—C(R$_5$)$_2$—N(R$_4$), C(R$_5$)$_2$—O—N(R$_4$), C(R$_5$)$_2$—S—C(R$_5$)$_2$, C(R$_5$)$_2$—N(R$_4$)—C(R$_5$)$_2$, C(R$_5$)$_2$—N(R$_4$)—O, C(R$_5$)$_2$—N(R$_4$)—S, C(R$_5$)=N—O, C(R$_5$)=N—S, C(R$_5$)=N—N(R$_4$), C(R$_5$)(R$_{17}$)—C(R$_3$)(R$_{17}$)—C(R$_5$)(R$_{17}$), or C(R$_5$)$_2$—C(R$_3$)(R$_5$)—C(R$_5$)$_2$;

W is N where

V---Z---Y is selected from O—C(R$_3$)=N, O—C(R$_5$)$_2$—N(R$_4$), O—C(R$_5$)$_2$—S, O—N=C(R$_5$) O—C(R$_5$)$_2$—O, S—C(R$_3$)=N, S—C(R$_5$)$_2$—N(R$_4$), S—N=C(R$_5$), N=C(R$_3$)—O, N=C(R$_3$)—S, N=C(R$_3$)—N(R$_4$), N(R$_4$)—N=C(R$_3$), N(R$_4$)—C(R$_5$)$_2$—O, N(R$_4$)—C(R$_5$)$_2$—S, N(R$_4$)—C(R$_5$)$_2$—N(R$_4$), C(R$_5$)$_2$—O—N(R$_4$), C(R$_5$)$_2$—N(R$_4$)—O, C(R$_5$)$_2$—N(R$_4$)—S, C(R$_5$)=N—O, C(R$_5$)=N—S, C(R$_5$)=N—N(R$_4$), C(R$_5$)=C(R$_3$)—O, C(R$_5$)=C(R$_3$)—S, C(R$_5$)=C(R$_5$)—N(R$_4$), C(R$_5$)=C(R$_5$)—C(R$_5$)$_2$, or C(R$_5$)$_2$—C(R$_3$)(R$_5$)—C(R$_5$)$_2$;

$W^1$, $W^2$, $W^3$, and $W^4$ are each independently N or C(R$_{21}$), provided that no more than two of $W^1$, $W^2$, $W^3$, and $W^4$ are N and further provided when more than two of $W^1$, $W^2$, $W^3$, and $W^4$ are C(R$_{21}$) that no more than two $R_{21}$ are other than H;

J is N(R$_{23}$), S, or O;

Q is N(R$_{19}$), O, or S;

Each $R_3$ is independently H, F, Cl, Br, I, alkyl, halogenated alkyl, substituted alkyl, cycloalkyl, lactam heterocycloalkyl, phenoxy, substituted phenoxy, $R_7$, $R_9$, —N(R$_4$)-aryl, —N(R$_4$)-halogenated phenyl, —N(R$_4$)-halogenated naphthyl, —O-halogenated phenyl, —O-substituted phenyl, —O-halogenated naphthyl, —O-substituted naphthyl, —S-halogenated phenyl, —S-substituted phenyl, —S-halogenated naphthyl, —S-substituted naphthyl, or alkyl substituted on the ω carbon with $R_{15}$ where said ω carbon is determined by counting the longest carbon chain of the alkyl moiety with the C-1 carbon being the carbon attached to the bicyclic moiety $W^0$ and the ω carbon being the carbon furthest, e.g., separated by the greatest number of carbon atoms in the chain, from said C-1 carbon;

Each $R_4$ is H, or alkyl;

Each $R_5$ is independently H, F, alkyl, substituted alkyl, halogenated alkyl, alkenyl, substituted alkenyl, halogenated alkenyl, alkynyl, substituted alkynyl, halogenated alkynyl, cycloalkyl, —C(O)NH$_2$, —CO$_2$R$_1$, or aryl;

$R_6$ is H, F, Br, I, Cl, —CN, —CF$_3$, —OR$_{16}$, —SR$_{16}$, or —N(R$_{16}$)$_2$;

Lower alkyl is both straight- and branched-chain moieties having from 1–4 carbon atoms;

Halogenated lower alkyl is an alkyl moiety having from 1–4 carbon atoms and having 1 to (2n+1) substituent(s) independently selected from F, Cl, Br, or I where n is the maximum number of carbon atoms in the moiety;

Substituted lower alkyl is an alkyl moiety from 1–4 carbon atoms and having 0–3 substituents independently selected from F, Cl, Br, or I and further having 1 substituent selected from $R_7$, $R_9$, —OR$_{10}$, —SR$_{10}$, —N(R$_{10}$)$_2$, —C(O)R$_{10}$, —C(O)NR$_{10}$R$_{10}$, —CN, —NR$_{10}$C(O)R$_{10}$, —S(O)$_2$NR$_{10}$R$_{10}$, —NR$_{10}$S(O)$_2$R$_{10}$, —NO$_2$, phenyl, or substituted phenyl;

Alkyl is both straight- and branched-chain moieties having from 1–6 carbon atoms;

Halogenated alkyl is an alkyl moiety having from 1–6 carbon atoms and having 1 to (2n+1) substituent(s) independently selected from F, Cl, Br, or I where n is the maximum number of carbon atoms in the moiety;

Substituted alkyl is an alkyl moiety from 1–6 carbon atoms and having 0–3 substituents independently selected from F, Cl, Br, or I and further having 1 substituent selected from $R_7$, $R_9$, —OR$_{10}$, —SR$_{10}$, —NR$_{10}$R$_{10}$, —C(O)R$_{10}$, —C(O)NR$_{10}$R$_{10}$, —CN, —NR$_{10}$C(O)R$_{10}$, —S(O)$_2$NR$_{10}$R$_{10}$, —NR$_{10}$S(O)$_2$R$_{10}$, —NO$_2$, phenyl, or substituted phenyl;

Alkenyl is straight- and branched-chain moieties having from 2–6 carbon atoms and having at least one carbon-carbon double bond;

Halogenated alkenyl is an unsaturated alkenyl moiety having from 2–6 carbon atoms and having 1 to (2n−1)

substituent(s) independently selected from F, Cl, Br, or I where n is the maximum number of carbon atoms in the moiety;

Substituted alkenyl is an unsaturated alkenyl moiety having from 2–6 carbon atoms and having 0–3 substituents independently selected from F, or Cl, and further having 1 substituent selected from $R_7$, $R_9$, —$OR_{10}$, —$SR_{10}$, —$N(R_{10})_2$, —$C(O)R_{10}$, —$C(O)N(R_{10})_2$, —$NR_{10}C(O)R_{10}$, —$S(O)_2N(R_{10})_2$, —$NR_{10}S(O)_2R_{10}$, —CN, phenyl, or substituted phenyl;

Alkynyl is straight- and branched-chained moieties having from 2–6 carbon atoms and having at least one carbon-carbon triple bond;

Halogenated alkynyl is an unsaturated alkynyl moiety having from 3–6 carbon atoms and having 1 to (2n–3) substituent(s) independently selected from F, Cl, Br, or I where n is the maximum number of carbon atoms in the moiety;

Substituted alkynyl is an unsaturated alkynyl moiety having from 3–6 carbon atoms and having 0–3 substituents independently selected from F, or Cl, and further having 1 substituent selected from $R_7$, $R_9$, —$OR_{10}$, —$SR_{10}$, —$N(R_{10})_2$, —$C(O)R_{10}$, —$C(O)N(R_{10})_2$, —$NR_{10}C(O)R_{10}$, —$S(O)_2N(R_{10})_2$, —$NR_{10}S(O)_2R_{10}$, —CN, phenyl, or substituted phenyl;

Cycloalkyl is a cyclic alkyl moiety having from 3–6 carbon atoms;

Lower cycloalkyl is a cyclic alkyl moiety having from 3–4 carbon atoms;

Halogenated cycloalkyl is a cyclic moiety having from 3–6 carbon atoms and having 1–4 substituents independently selected from F, or Cl;

Substituted cycloalkyl is a cyclic moiety having from 3–6 carbon atoms and having 0–3 substituents independently selected from F, or Cl, and further having 1 substituent selected from —$OR_{10}$, —$SR_{10}$, —$N(R_{10})_2$, —$C(O)R_{10}$, —CN, —$C(O)N(R_{10})_2$, —$NR_{10}C(O)R_{10}$, —$S(O)_2N(R_{10})_2$, —$NR_{10}S(O)_2R_{10}$, —$NO_2$, phenyl, or substituted phenyl;

Heterocycloalkyl is a cyclic moiety having 4–7 atoms with 1–2 atoms within the ring being —S—, —$N(R_{19})$—, or —O—;

Halogenated heterocycloalkyl is a cyclic moiety having from 4–7 atoms with 1–2 atoms within the ring being —S—, —$N(R_{19})$—, or —O—, and having 1–4 substituents independently selected from F, or Cl;

Substituted heterocycloalkyl is a cyclic moiety having from 4–7 atoms with 1–2 atoms within the ring being —S—, —$N(R_{19})$—, or —O— and having 0–3 substituents independently selected from F, or Cl, and further having 1 substituent selected from $R_7$, $R_9$, —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$NO_2$, —$S(O)_2NR_{10}R_{10}$, —$NR_{10}S(O)_2R_{10}$, phenyl, or phenyl having 1 substituent selected from $R_{20}$ and further having 0–3 substituents independently selected from F, Cl, Br, or I;

Lactam heterocycloalkyl is a cyclic moiety having from 4–7 atoms with one atom being only nitrogen with the bond to the lactam heterocycloalkyl thru said atom being only nitrogen and having a =O on a carbon adjacent to said nitrogen, and having up to 1 additional ring atom being oxygen, sulfur, or nitrogen and further having 0–2 substituents selected from F, Cl, Br, I, or $R_{14}$ where valency allows;

Substituted phenoxy is a phenoxy either having 1–3 substituents independently selected from F, Cl, Br, or I, or having 1 substituent selected from $R_{12}$ and 0–2 substituents independently selected from F, Cl, Br, or I;

Aryl is phenyl, substituted phenyl, naphthyl, or substituted naphthyl;

Substituted phenyl is a phenyl either having 1–4 substituents independently selected from F, Cl, Br, or I, or having 1 substituent selected from $R_{12}$ and 0–3 substituents independently selected from F, Cl, Br, or I;

Substituted naphthyl is a naphthalene moiety either having 1–4 substituents independently selected from F, Cl, Br, or I, or having 1 substituent selected from $R_{12}$ and 0–3 substituents independently selected from F, Cl, Br, or I, where the substitution can be independently on either only one ring or both rings of said naphthalene moiety;

$R_7$ is 5-membered heteroaromatic mono-cyclic moieties containing within the ring 1–3 heteroatoms independently selected from the group consisting of —O—, =N—, —$N(R_{19})$—, and —S—, and having 0–1 substituent selected from $R_{20}$ and further having 0–3 substituents independently selected from F, Cl, Br, or I, or $R_7$ is 9-membered fused-ring moieties having a 6-membered ring fused to a 5-membered ring and having the formula

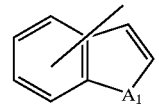

wherein $A_1$ is O, S, or $NR_{19}$,

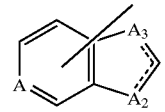

wherein A is $CR_{18}$ or N, $A_2$ and $A_3$ are independently selected from $CR_{18}$, $C(R_{18})_2$, O, S, N, or $NR_{19}$, provided that both $A_2$ and $A_3$ are not simultaneously O, simultaneously S, or simultaneously O and S, or

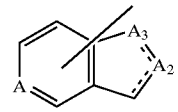

wherein $A_2$ and $A_3$ are independently selected from $CR_{18}$, $C(R_{18})_2$, O, S, N, or $NR_{19}$, and A is $CR_{18}$ or N, each 9-membered fused-ring moiety having 0–1 substituent selected from $R_{20}$ and further having 0–3 substituent(s) independently selected from F, Cl, Br, or I, and having a bond directly or indirectly attached to the core molecule where valency allows in either the 6-membered or the 5-membered ring of the fused-ring moiety;

Each $R_8$ is independently F, alkyl, substituted alkyl, halogenated alkyl, alkenyl, substituted alkenyl, halogenated alkenyl, alkynyl, substituted alkynyl, halogenated alkynyl, cycloalkyl, —$C(O)NH_2$, —$CO_2R_1$, or aryl;

$R_9$ is 6-membered heteroaromatic mono-cyclic moieties containing within the ring 1–3 heteroatoms selected from =N— and having 0–1 substituent selected from $R_{20}$ and 0–3 substituent(s) independently selected from F, Cl, Br, or I, or $R_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from $R_{20}$ and 0–3 substituent(s) independently selected from F, Cl, Br, or I and having a bond directly or indirectly attached to the core molecule where valency allows;

Each $R_{10}$ is independently H, alkyl, cycloalkyl, heterocycloalkyl, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, phenyl, or substituted phenyl;

Each $R_{11}$ is independently H, alkyl, cycloalkyl, heterocycloalkyl, halogenated alkyl, halogenated cycloalkyl, or halogenated heterocycloalkyl;

$R_{12}$ is $-OR_{11}$, $-SR_{11}$, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, $-NR_{11}R_{11}R_{11}$, $-C(O)R_{11}$, $-NO_2$, $-C(O)NR_{11}R_{11}$, $-CN$, $-NR_{11}C(O)R_{11}$, $-S(O)_2NR_{11}R_{11}$, or $-NR_{11}S(O)_2R_{11}$;

$R_{13}$ is $-OR_{11}$, $-SR_{11}$, $-N(R_{11})_2$, $-C(O)R_{11}$, $-C(O)NR_{11}R_{11}$, $-CN$, $-CF_3$, $-NR_{11}C(O)R_{11}$, $-S(O)_2N(R_{11})_2$, $-NR_{11}S(O)_2R_{11}$, or $-NO_2$;

$R_{14}$ is alkyl, substituted alkyl, halogenated alkyl, $-OR_{11}$, $-CN$, $-NO_2$, $-NR_{10}R_{10}$;

$R_{15}$ is aryl, $R_7$, or $R_9$;

$R_{16}$ is H, alkyl, substituted alkyl, cycloalkyl, halogenated alkyl, substituted phenyl, or substituted naphthyl;

One of $R_{17}$ is H, alkyl, substituted alkyl, halogenated alkyl, alkenyl, substituted alkenyl, halogenated alkenyl, alkynyl, substituted alkynyl, halogenated alkynyl, $-CN$, F, Br, Cl, I, $-OR_1$, $-C(O)NH_2$, $-NHR_1$, $-SR_1$, $-CO_2R_1$, aryl, $R_7$, or $R_9$, and each of the other two $R_{17}$ is independently alkyl, substituted alkyl, halogenated alkyl, alkenyl, substituted alkenyl, halogenated alkenyl, alkynyl, substituted alkynyl, halogenated alkynyl, $-CN$, F, Br, Cl, I, $-OR_1$, $-C(O)NH_2$, $-NHR_1$, $-SR_1$, $-CO_2R_1$, aryl, $R_7$, or $R_9$;

Each $R_{18}$ is independently selected from H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, $-OR_{11}$, $-SR_{11}$, $-NR_{11}R_{11}$, $-C(O)R_{11}$, $-NO_2$, $-C(O)N(R_{11})_2$, $-CN$, $-NR_{11}C(O)R_{11}$, $-S(O)_2N(R_{11})_2$, F, Cl, Br, or I, $-NR_{11}S(O)_2R_{11}$, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, $-OR_{11}$, $-SR_{11}$, $-NR_{11}R_{11}$, $-C(O)R_{11}$, $-NO_2$, $-C(O)NR_{11}R_{11}$, $-CN$, $-NR_{11}C(O)R_{11}$, $-S(O)_2NR_{11}R_{11}$, or $-NR_{11}S(O)_2R_{11}$, and further provided that the fused-ring moiety has 0–3 substituent(s) selected from F, Cl, Br, or I;

$R_{19}$ is H, alkyl, halogenated alkyl, substituted alkyl, cycloalkyl, halogenated cycloalkyl, substituted cycloalkyl, phenyl, or phenyl having 1 substituent selected from $R_{20}$ and further having 0–3 substituents independently selected from F, Cl, Br, or I;

$R_{20}$ is alkyl, cycloalkyl, heterocycloalkyl, halogenated alkyl, halogenated cycloalkyl, halogenated heterocycloalkyl, $-OR_{11}$, $-SR_{11}$, $-NR_{11}R_{11}$, $-C(O)R_{11}$, $-C(O)NR_{11}R_{11}$, $-CN$, $-NR_{11}C(O)R_{11}$, $-S(O)_2NR_{11}R_{11}$, $-NR_{11}S(O)_2R_{11}$, $-NO_2$, alkyl substituted with 1–4 substituent(s) independently selected from F, Cl, Br, I, or $R_{13}$, cycloalkyl substituted with 1–4 substituent(s) independently selected from F, Cl, Br, I, or $R_{13}$, or heterocycloalkyl substituted with 1–4 substituent(s) independently selected from F, Cl, Br, I, or $-R_{13}$;

$R_{21}$ is H, F, Cl, Br, I, alkyl, substituted alkyl, halogenated alkyl, cycloalkyl, $-CN$, $-NR_{22}R_{22}$, $-OR_{22}$, or $-SR_{22}$;

Each $R_{22}$ is independently H, alkyl, substituted alkyl, cycloalkyl, halogenated alkyl, substituted cycloalkyl, heterocycloalkyl, or substituted heterocycloalkyl;

$R_{23}$ is alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, substituted phenyl, naphthyl, substituted naphthyl, $R_7$, or $R_9$;

or pharmaceutical composition, pharmaceutically acceptable salt, racemic mixture, or pure enantiomer thereof useful to treat any one of or combination of cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, depression, general anxiety disorder, age-related macular degeneration, Parkinson's disease, tardive dyskinesia, Pick's disease, post traumatic stress disorder, dysregulation of food intake including bulimia and anorexia nervosa, withdrawal symptoms associated with smoking cessation and dependant drug cessation, Gilles de la Tourette's Syndrome, glaucoma, neurodegeneration associated with glaucoma, or symptoms associated with pain.

In another aspect, the invention includes methods of treating a mammal suffering from schizophrenia or psychosis by administering compounds of Formula I in conjunction with antipsychotic drugs. The compounds of Formula I and the antipsychotic drugs can be administered simultaneously or at separate intervals. When administered simultaneously the compounds of Formula I and the antipsychotic drugs can be incorporated into a single pharmaceutical composition. Alternatively, two separate compositions, i.e., one containing compounds of Formula I and the other containing antipsychotic drugs, can be administered simultaneously.

The present invention also includes the compounds of the present invention, pharmaceutical compositions containing the active compounds, and methods to treat the identified diseases.

Abbreviations which are well known to one of ordinary skill in the art may be used (e.g., "Ph" for phenyl, "Me" for methyl, "Et" for ethyl, "h" or "hr" for hour or hours, "min" for minute or minutes, and "rt" for room temperature).

All temperatures are in degrees Centigrade.

Room temperature is within the range of 15–25 degrees Celsius.

AChR refers to acetylcholine receptor.

nAChR refers to nicotinic acetylcholine receptor.

Pre-senile dementia is also known as mild cognitive impairment.

$5HT_3R$ refers to the serotonin-type 3 receptor.

α-btx refers to α-bungarotoxin.

FLIPR refers to a device marketed by Molecular Devices, Inc. designed to precisely measure cellular fluorescence in a high throughput whole-cell assay. (Schroeder et. al., *J. Biomolecular Screening*, 1(2), p 75–80, 1996).

TLC refers to thin-layer chromatography.

HPLC refers to high pressure liquid chromatography.
MeOH refers to methanol.
EtOH refers to ethanol.
IPA refers to isopropyl alcohol.
THF refers to tetrahydrofuran.
DMSO refers to dimethylsulfoxide.
DMF refers to N,N-dimethylformamide.
EtOAc refers to ethyl acetate.
TMS refers to tetramethylsilane.
TEA refers to triethylamine.
DIEA refers to N,N-diisopropylethylamine.
MLA refers to methyllycaconitine.
Ether refers to diethyl ether.
HATU refers to O-(7-azabenzotriazol-1-yl)-N,N,N', N'-tetramethyluronium hexafluorophosphate.
CDI refers to carbonyl diimidazole.
NMO refers to N-methylmorpholine-N-oxide.
TPAP refers to tetrapropylammonium perruthenate.
$Na_2SO_4$ refers to sodium sulfate.
$K_2CO_3$ refers to potassium carbonate.
$MgSO_4$ refers to magnesium sulfate.
When $Na_2SO_4$, $K_2CO_3$, or $MgSO_4$ is used as a drying agent, it is anhydrous.
Halogen is F, Cl, Br, or I.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-6}$ alkyl refers to alkyl of one to six carbon atoms.

Non-inclusive examples of heteroaryl compounds that fall within the definition of $R_7$ and $R_9$ include, but are not limited to, thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, benzoxazolyl, pyrazolyl, triazolyl, tetrazolyl, isoxazolyl, oxazolyl, pyrrolyl, isoquinolinyl, cinnolinyl, indazolyl, indolizinyl, phthalazinyl, pydridazinyl, triazinyl, isoindolyl, purinyl, oxadiazolyl, furazanyl, benzofurazanyl, benzothiophenyl, benzothiazolyl, quinazolinyl, quinoxalinyl, naphthridinyl, and furopyridinyl.

Non-inclusive examples of heterocycloalkyl include, but are not limited to, tetrahydrofurano, tetrahydropyrano, morpholino, pyrrolidino, piperidino, piperazine, azetidino, azetidinono, oxindolo, dihydroimidazolo, and pyrrolidinono Some of the amines described herein require the use of an amine-protecting group to ensure functionalization of the desired nitrogen. One of ordinary skill in the art would appreciate where, within the synthetic scheme to use said protecting group. Amino protecting group includes, but is not limited to, carbobenzyloxy (CBz), tert butoxy carbonyl (BOC) and the like. Examples of other suitable amino protecting groups are known to person skilled in the art and can be found in "Protective Groups in Organic synthesis," 3rd Edition, authored by Theodora Greene and Peter Wuts.

ω carbon with $R_{15}$ where said ω carbon is determined by counting the longest carbon chain of the alkyl moiety with the C-1 carbon being the carbon attached to the bicyclic moiety $W^0$ and the ω carbon being the carbon furthest, e.g., separated by the greatest number of carbon atoms in the chain, from said C-1 carbon:

The core molecule is [Azabicyclic-N—($R_1$)—C(=X)—]. The bond to the core molecule is between $W^0$ and the C(=X) of the core molecule. Therefore, when determining the ω carbon, the C-1 carbon will be the carbon attached, as valency allows, to the $W^0$ moiety and the ω carbon will be the carbon furthest from said C-1 carbon.

Mammal denotes human and other mammals.
Brine refers to an aqueous saturated sodium chloride solution.
Equ means molar equivalents.
IR refers to infrared spectroscopy.
Lv refers to leaving groups within a molecule, including Cl, OH, or mixed anhydride.
NMR refers to nuclear (proton) magnetic resonance spectroscopy, chemical shifts are reported in ppm (δ) downfield from TMS.
MS refers to mass spectrometry expressed as m/e or mass/charge unit. HRMS refers to high resolution mass spectrometry expressed as m/e or mass/charge unit. $M+H^+$ refers to the positive ion of a parent plus a hydrogen atom. $M-H^-$ refers to the negative ion of a parent minus a hydrogen atom. $M+Na^+$ refers to the positive ion of a parent plus a sodium atom. $M+K^+$ refers to the positive ion of a parent plus a potassium atom. EI refers to electron impact. ESI refers to electrospray ionization. CI refers to chemical ionization. FAB refers to fast atom bombardment.

Compounds of the present invention may be in the form of pharmaceutically acceptable salts. The term "pharmaceutically acceptable salts" refers to salts prepared from pharmaceutically acceptable non-toxic bases including inorganic bases and organic bases, and salts prepared from inorganic acids, and organic acids. Salts derived from inorganic bases include aluminum, ammonium, calcium, ferric, ferrous, lithium, magnesium, potassium, sodium, zinc, and the like. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and the like. Salts derived from inorganic acids include salts of hydrochloric acid, hydrobromic acid, hydroiodic acid, sulfuric acid, phosphoric acid, phosphorous acid and the like. Salts derived from pharmaceutically acceptable organic non-toxic acids include salts of $C_{1-6}$ alkyl carboxylic acids, di-carboxylic acids, and tri-carboxylic acids such as acetic acid, propionic acid, fumaric acid, succinic acid, tartaric acid, maleic acid, adipic acid, and citric acid, and aryl and alkyl sulfonic acids such as toluene sulfonic acids and the like.

By the term "effective amount" of a compound as provided herein is meant a nontoxic but sufficient amount of the compound(s) to provide the desired effect. As pointed out below, the exact amount required will vary from subject to subject, depending on the species, age, and general condition of the subject, the severity of the disease that is being treated, the particular compound(s) used, the mode of administration, and the like. Thus, it is not possible to specify an exact "effective amount." However, an appropriate effective amount may be determined by one of ordinary skill in the art using only routine experimentation.

The compounds of Formula I have optically active center (s) on the Azabicyclo moiety. Although it is desirable that the stereochemical purity be as high as possible, absolute purity is not required. This invention involves racemic mixtures and compositions of varying degrees of stereochemical purities. It is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions.

The amount of therapeutically effective compound(s) that is administered and the dosage regimen for treating a disease condition with the compounds and/or compositions of this invention depends on a variety of factors, including the age, weight, sex and medical condition of the subject, the severity of the disease, the route and frequency of administration, and the particular compound(s) employed, and thus may vary widely. The compositions contain well know carriers and excipients in addition to a therapeutically effective amount of compounds of Formula I. The pharmaceutical compositions may contain active ingredient in the range of about 0.001 to 100 mg/kg/day for an adult, preferably in the range of about 0.1 to 50 mg/kg/day for an adult. A total daily dose of about 1 to 1000 mg of active ingredient may be appropriate for an adult. The daily dose can be administered in one to four doses per day.

In addition to the compound(s) of Formula I, the composition for therapeutic use may also comprise one or more non-toxic, pharmaceutically acceptable carrier materials or excipients. The term "carrier" material or "excipient" herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, and then tableted or encapsulated for convenient administration. Such capsules or tablets may contain a controlled-release formulation as may be provided in a dispersion of active compound in hydroxypropyl-methyl cellulose, or other methods known to those skilled in the art. For oral administration, the pharmaceutical composition may be in the form of, for example, a tablet, capsule, suspension or liquid. If desired, other active ingredients may be included in the composition.

In addition to the oral dosing, noted above, the compositions of the present invention may be administered by any suitable route, in the form of a pharmaceutical composition adapted to such a route, and in a dose effective for the treatment intended. The compositions may, for example, be administered parenterally, e.g., intravascularly, intraperitoneally, subcutaneously, or intramuscularly. For parenteral administration, saline solution, dextrose solution, or water may be used as a suitable carrier. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, EtOH, corn oil, cottonseed oil, peanut oil, sesame oil, benzyl alcohol, sodium chloride, and/or various buffers. Other adjuvants and modes of administration are well and widely known in the pharmaceutical art.

The serotonin type 3 receptor ($5HT_3R$) is a member of a superfamily of ligand-gated ion channels, which includes the muscle and neuronal nAChR, the glycine receptor, and the γ-aminobutyric acid type A receptor. Like the other members of this receptor superfamily, the $5HT_3R$ exhibits a large degree of sequence homology with α7 nAChR but functionally the two ligand-gated ion channels are very different. For example, α7 nAChR is rapidly inactivated, is highly permeable to calcium and is activated by acetylcholine and nicotine. On the other hand, $5HT_3R$ is inactivated slowly, is relatively impermeable to calcium and is activated by serotonin. These experiments suggest that the α7 nAChR and $5HT_3R$ proteins have some degree of homology, but function very differently. Indeed the pharmacology of the channels is very different. For example, Ondansetron, a highly selective $5HT_3R$ antagonist, has little activity at the α7 nAChR. The converse is also true. For example, GTS-21, a highly selective α7 nAChR agonist, has little activity at the $5HT_3R$.

α7 nAChR is a ligand-gated $Ca^{++}$ channel formed by a homopentamer of α7 subunits. Previous studies have established that α-bungarotoxin (α-btx) binds selectively to this homopetameric, α7 nAChR subtype, and that α7 nAChR has a high affinity binding site for both α-btx and methyllycaconitine (MLA). α7 nAChR is expressed at high levels in the hippocampus, ventral tegmental area and ascending cholinergic projections from nucleus basilis to thalamocortical areas. α7 nAChR agonists increase neurotransmitter release, and increase cognition, arousal, attention, learning and memory.

Data from human and animal pharmacological studies establish that nicotinic cholinergic neuronal pathways control many important aspects of cognitive function including attention, learning and memory (Levin, E. D., *Psychopharmacology*, 108:417–31, 1992; Levin, E. D. and Simon B. B., *Psychopharmacology*, 138:217–30, 1998). For example, it is well known that nicotine increases cognition and attention in humans. ABT-418, a compound that activates α4β2 and α7 nAChR, improves cognition and attention in clinical trials of Alzheimer's disease and attention-deficit disorders (Potter, A. et. al., *Psychopharmacology* (Berl)., 142(4):334–42, March 1999; Wilens, T. E. et. al., *Am. J. Psychiatry*, 156(12):1931–7, December 1999). It is also clear that nicotine and selective but weak α7 nAChR agonists increase cognition and attention in rodents and non-human primates.

Schizophrenia is a complex multifactorial illness caused by genetic and non-genetic risk factors that produce a constellation of positive and negative symptoms. The positive symptoms include delusions and hallucinations and the negative symptoms include deficits in affect, attention, cognition and information processing. No single biological element has emerged as a dominant pathogenic factor in this disease. Indeed, it is likely that schizophrenia is a syndrome that is produced by the combination of many low penetrance risk factors. Pharmacological studies established that dopamine receptor antagonists are efficacious in treating the overt psychotic features (positive symptoms) of schizophrenia such as hallucinations and delusions. Clozapine, an "atypical" antipsychotic drug, is novel because it is effective in treating both the positive and some of the negative symptoms of this disease. Clozapine's utility as a drug is greatly limited because continued use leads to an increased risk of agranulocytosis and seizure. No other antipsychotic drug is effective in treating the negative symptoms of schizophrenia. This is significant because the restoration of cognitive functioning is the best predictor of a successful clinical and functional outcome of schizophrenic patients (Green, M. F., *Am J Psychiatry*, 153:321–30, 1996). By extension, it is clear that better drugs are needed to treat the cognitive disorders of schizophrenia in order to restore a better state of mental health to patients with this disorder.

One aspect of the cognitive deficit of schizophrenia can be measured by using the auditory event-related potential (P50) test of sensory gating. In this test, electroencepholographic (EEG) recordings of neuronal activity of the hippocampus are used to measure the subject's response to a series of auditory "clicks" (Adler, L. E. et. al., *Biol. Psychiatry*, 46:8–18, 1999). Normal individuals respond to the first click with greater degree than to the second click. In general, schizophrenics and schizotypal patients respond to both clicks nearly the same (Cullum, C. M. et. al., *Schizophr. Res.*, 10:131–41, 1993). These data reflect a schizophrenic's inability to "filter" or ignore unimportant information. The sensory gating deficit appears to be one of the key pathological features of this disease (Cadenhead, K. S. et. al., *Am. J. Psychiatry*, 157:55–9, 2000). Multiple studies show that nicotine normalizes the sensory deficit of schizophrenia (Adler, L. E. et. al., *Am. J. Psychiatry*, 150:1856–61, 1993). Pharmacological studies indicate that nicotine's effect on sensory gating is via the $\alpha 7$ nAChR (Adler, L. E. et. al., *Schizophr. Bull.*, 24:189–202, 1998). Indeed, the biochemical data indicate that schizophrenics have 50% fewer of $\alpha 7$ nAChR receptors in the hippocampus, thus giving a rationale to partial loss of $\alpha 7$ nAChR functionality (Freedman, R. et. al., *Biol. Psychiatry*, 38:22–33, 1995). Interestingly, genetic data indicate that a polymorphism in the promoter region of the $\alpha 7$ nAChR gene is strongly associated with the sensory gating deficit in schizophrenia (Freedman, R. et. al., *Proc. Nat'l Acad. Sci. USA*, 94(2):587–92, 1997; Myles-Worsley, M. et. al., *Am. J. Med. Genet*, 88(5):544–50, 1999). To date, no mutation in the coding region of the $\alpha 7$ nAChR has been identified. Thus, schizophrenics express the same $\alpha 7$ nAChR as non-schizophrenics.

Selective $\alpha 7$ nAChR agonists may be found using a functional assay on FLIPR (see WO 00/73431 A2). FLIPR is designed to read the fluorescent signal from each well of a 96 or 384 well plate as fast as twice a second for up to 30 minutes. This assay may be used to accurately measure the functional pharmacology of $\alpha 7$ nAChR and $5HT_3R$. To conduct such an assay, one uses cell lines that expressed functional forms of the $\alpha 7$ nAChR using the $\alpha 7/5\text{-}HT_3$ channel as the drug target and cell lines that expressed functional $5HT_3R$. In both cases, the ligand-gated ion channel was expressed in SH-EP1 cells. Both ion channels can produce robust signal in the FLIPR assay.

The compounds of the present invention are $\alpha 7$ nAChR agonists and may be used to treat a wide variety of diseases. For example, they may be used in treating schizophrenia, or psychosis.

Schizophrenia is a disease having multiple aspects. Currently available drugs are generally aimed at controlling the positive aspects of schizophrenia, such as delusions. One drug, Clozapine, is aimed at a broader spectrum of symptoms associated with schizophrenia. This drug has many side effects and is thus not suitable for many patients. Thus, there is a need for a drug to treat the cognitive and attention deficits associated with schizophrenia. Similarly, there is a need for a drug to treat the cognitive and attention deficits associated with schizoaffective disorders, or similar symptoms found in the relatives of schizophrenic patients.

Psychosis is a mental disorder characterized by gross impairment in the patient's perception of reality. The patient may suffer from delusions, and hallucinations, and may be incoherent in speech. His behavior may be agitated and is often incomprehensible to those around him. In the past, the term psychosis has been applied to many conditions that do not meet the stricter definition given above. For example, mood disorders were named as psychoses.

There are a variety of antipsychotic drugs. The conventional antipsychotic drugs include Chlorpromazine, Fluphenazine, Haloperidol, Loxapine, Mesoridazine, Molindone, Perphenazine, Pimozide, Thioridazine, Thiothixene, and Trifluoperazine. These drugs all have an affinity for the dopamine 2 receptor.

These conventional antipsychotic drugs have several side effects, including sedation, weight gain, tremors, elevated prolactin levels, akathisia (motor restlessness), dystonia and muscle stiffness. These drugs may also cause tardive dyskinesia. Unfortunately, only about 70% of patients with schizophrenia respond to conventional antipsychotic drugs. For these patients, atypical antipsychotic drugs are available.

Atypical antipsychotic drugs generally are able to alleviate positive symptoms of psychosis while also improving negative symptoms of the psychosis to a greater degree than conventional antipsychotics. These drugs may improve neurocognitive deficits. Extrapyramidal (motor) side effects are not as likely to occur with the atypical antipsychotic drugs, and thus, these atypical antipsychotic drugs have a lower risk of producing tardive dyskinesia. Finally these atypical antipsychotic drugs cause little or no elevation of prolactin. Unfortunately, these drugs are not free of side effects. Although these drugs each produce different side effects, as a group the side effects include: agranulocytosis; increased risk of seizures, weight gain, somnolence, dizziness, tachycardia, decreased ejaculatory volume, and mild prolongation of QTc interval.

In a combination therapy to treat multiple symptoms of diseases such as schizophrenia, the compounds of Formula I and the anti-psychotic drugs can be administered simultaneously or at separate intervals. When administered simultaneously the compounds of Formula I and the anti-psychotic drugs can be incorporated into a single pharmaceutical composition, e.g., a pharmaceutical combination therapy composition. Alternatively, two separate compositions, i.e., one containing compounds of Formula I and the other containing anti-psychotic drugs, can be administered simultaneously. Examples of anti-psychotic drugs, in addition to those listed above, include, but are not limited to, Thorazine, Mellaril, Trilafon, Navane, Stelazine, Permitil, Prolixin, Risperdal, Zyprexa, Seroquel, ZELDOX, Acetophenazine, Carphenazine, Chlorprothixene, Droperidol, Loxapine, Mesoridazine, Molindone, Ondansetron, Pimozide, Prochlorperazine, and Promazine.

A pharmaceutical combination therapy composition can include therapeutically effective amounts of the compounds of Formula I, noted above, and a therapeutically effective amount of anti-psychotic drugs. These compositions may be formulated with common excipients, diluents or carriers, and compressed into tablets, or formulated elixirs or solutions for convenient oral administration or administered by intramuscular intravenous routes. The compounds can be administered rectally, topically, orally, sublingually, or parenterally and maybe formulated as sustained relief dosage forms and the like.

When separately administered, therapeutically effective amounts of compositions containing compounds of Formula I and anti-psychotic drugs are administered on a different schedule. One may be administered before the other as long as the time between the two administrations falls within a therapeutically effective interval. A therapeutically effective interval is a period of time beginning when one of either (a) the compounds of Formula I, or (b) the anti-psychotic drugs is administered to a human and ending at the limit of the beneficial effect in the treatment of schizophrenia or psychosis of the combination of (a) and (b). The methods of administration of the compounds of Formula I and the anti-psychotic drugs may vary. Thus, either agent or both agents may be administered rectally, topically, orally, sublingually, or parenterally.

As discussed, the compounds of the present invention are $\alpha7$ nAChR agonists. Therefore, as another aspect of the present invention, the compounds of the present invention may be used to treat a variety of diseases including cognitive and attention deficit symptoms of Alzheimer's, neurodegeneration associated with diseases such as Alzheimer's disease, pre-senile dementia (also known as mild cognitive impairment), and senile dementia.

Alzheimer's disease has many aspects, including cognitive and attention deficits. Currently, these deficits are treated with cholinesterase inhibitors. These inhibitors slow the break down of acetylcholine, and thereby provide a general nonspecific increase in the activity of the cholinergic nervous system. Since the drugs are nonspecific, they have a wide variety of side effects. Thus, there is a need for a drug that stimulates a portion of the cholinergic pathways and thereby provides improvement in the cognitive and attention deficits associated with Alzheimer's disease without the side effects created by nonspecific stimulation of the cholinergic pathways.

Neurodegeneration is a common problem associated with diseases such as Alzheimer's disease. While the current drugs treat some of the symptoms of this disease, they do not control the underlying pathology of the disease. Accordingly, it would be desirable to provide a drug that can slow the progress of Alzheimer's disease.

Pre-senile dementia (mild cognitive impairment) concerns memory impairment rather than attention deficit problems and otherwise unimpaired cognitive functioning. Mild cognitive impairment is distinguished from senile dementia in that mild cognitive impairment involves a more persistent and troublesome problem of memory loss for the age of the patient. There currently is no medication specifically identified for treatment of mild cognitive impairment, due somewhat to the newness of identifying the disease. Therefore, there is a need for a drug to treat the memory problems associated with mild cognitive impairment.

Senile dementia is not a single disease state. However, the conditions classified under this name frequently include cognitive and attention deficits. Generally, these deficits are not treated. Accordingly, there is a need for a drug that provides improvement in the cognitive and attention deficits associated with senile dementia.

As discussed, the compounds of the present invention are $\alpha7$ nAChR agonists. Therefore, yet other diseases to be treated with compounds of the present invention include treating the cognitive and attention deficits as well as the neurodegeneration associated with any one or more or combination of the following: attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulemia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

Attention deficit disorder is generally treated with methylphenidate, an amphetamine-like molecule that has some potential for abuse. Accordingly, it would be desirable to provide a drug that treats attention deficit disorder while having fewer side effects than the currently used drug.

Attention deficit hyperactivity disorder, otherwise known as ADHD, is a neurobehavioral disorder affecting 3–5% of all American children. ADHD concerns cognitive alone or both cognitive and behavioral actions by interfering with a person's ability to stay on a task and to exercise age-appropriate inhibition. Several types of ADHD exist: a predominantly inattentive subtype, a predominantly hyperactive-impulsive subtype, and a combined subtype. Treatment may include medications such as methylphenidate, dextroamphetamine, or pemoline, which act to decrease impulsivity and hyperactivity and to increase attention. No "cure" for ADHD currently exists. Children with the disorder seldom outgrow it; therefore, there is a need for appropriate medicaments.

Depression is a mood disorder of varying lengths of normally several months to more than two years and of varying degrees of feelings involving sadness, despair, and discouragement. The heterocyclic antidepressants (HCA's) are currently the largest class of antidepressants, but monoamine oxidase inhibitors (MAOI's) are used in particular types of depression. Common side effects from HCA's are sedation and weight gain. In elderly patients with organic brain disease, the side effects from HCA's can also include seizures and behavioral symptoms. The main side effects from using MAOI's occur from dietary and drug interactions. Therefore, agents with fewer side effects would be useful.

Anxiety disorders (disorders with prominent anxiety or phobic avoidance), represent an area of umet medical needs in the treatment of psychiatric illness. See Diagnostic & Statistical Manual of Mental Disorders, IV (1994), pp 393–394, for various disease forms of anxiety.

General anxiety disorder (GAD) occurs when a person worries about things such as family, health, or work when there is no reason to worry and is unable not to worry. About 3 to 4% of the U.S. population has GAD during the course of a year. GAD most often strikes people in childhood or adolescence, but can begin in adulthood, too. It affects women more often than men. Currently, treatment involves cognitive-behavioral therapy, relaxation techniques, and biofeedback to control muscle tension and medications such as benzodiazepines, imipramine, and buspirone. These drugs are effective but all have side-effect liabilities. Therefore, there is a need of a pharmaceutical agent to address the symptoms with fewer side effects.

Anxiety also includes post-traumatic stress disorder (PTSD), which is a form of anxiety triggered by memories of a traumatic event that directly affected the patient or that the patient may have witnessed. The disorder commonly affects survivors of traumatic events including sexual assault, physical assault, war, torture, natural disasters, an automobile accident, an airplane crash, a hostage situation, or a death camp. The affliction also can affect rescue workers at an airplane crash or a mass shooting, someone who witnessed a tragic accident or someone who has unexpectedly lost a loved one. Treatment for PTSD includes cognitive-behavioral therapy, group psychotherapy, and medications such as Clonazepam, Lorazepam and selective serotonin-reuptake inhibitors such as Fluoxetine, Sertraline, Paroxetine, Citalopram and Fluvoxamine. These medications help control anxiety as well as depression. Various forms of exposure therapy (such as systemic desensitization and imaginal flooding) have all been used with PTSD patients. Exposure treatment for PTSD involves repeated reliving of the trauma, under controlled conditions, with the aim of facilitating the processing of the trauma. Therefore, there is a need for better pharmaceutical agents to treat post traumatic stress disorder.

Mood and affective disorders fall within a large group of diseases, including monopolar depression and bi-polar mood disorder. These diseases are treated with three major classes of compounds. The first group is the heterocyclic antidepressant (HCA's). This group includes the well-known tricyclic antidepressants. The second group of compounds used to treat mood disorders is the monoamine oxidase inhibitors (MAOI's) that are used in particular types of diseases. The third drug is lithium. Common side effects from HCA's are sedation and weight gain. In elderly patients with organic brain disease, the side effects of HCA's can also include seizures and behavioral symptoms. The main side effects from using MAOI's occur from dietary and drug interactions. Benign side effects from the use of lithium include, but are not limited to, weight gain, nausea, diarrhea, polyuria, polydipsia, and tremor. Toxic side effects from lithium can include persistent headache, mental confusion, and may reach seizures and cardiac arrhythmias. Therefore, agents with less side effects or interactions with food or other medications would be useful.

Borderline personality disorder, although not as well known as bipolar disorder, is more common. People having borderline personality disorder suffer from a disorder of emotion regulation. Pharmaceutical agents are used to treat specific symptoms, such as depression or thinking distortions.

Acquired immune deficiency syndrome (AIDS) results from an infection with the human immunodeficiency virus (HIV). This virus attacks selected cells and impairs the proper function of the immune, nervous, and other systems. HIV infection can cause other problems such as, but not limited to, difficulties in thinking, otherwise known as AIDS dementia complex. Therefore, there is a need to drugs to relieve the confusion and mental decline of persons with AIDS.

Amyotrophic lateral sclerosis, also known as Lou Gehrig's disease, belongs to a class of disorders known as motor neuron diseases wherein specific nerve cells in the brain and spinal cord gradually degenerate to negatively affect the control of voluntary movement. Currently, there is no cure for amyotrophic lateral sclerosis although patients may receive treatment from some of their symptoms and although Riluzole has been shown to prolong the survival of patients. Therefore, there is a need for a pharmaceutical agent to treat this disease.

Traumatic brain injury occurs when the brain is damaged from a sudden physical assault on the head. Symptoms of the traumatic brain injury include confusion and other cognitive problems. Therefore, there is a need to address the symptoms of confusion and other cognitive problems.

Brain tumors are abnormal growths of tissue found inside of the skull. Symptoms of brain tumors include behavioral and cognitive problems. Surgery, radiation, and chemotherapy are used to treat the tumor, but other agents are necessary to address associated symptoms. Therefore, there is a need to address the symptoms of behavioral and cognitive problems.

Persons with Down's syndrome have in all or at least some of their cells an extra, critical portion of the number 21 chromosome. Adults who have Down's syndrome are known to be at risk for Alzheimer-type dementia. Currently, there is no proven treatment for Down's syndrome. Therefore, there is a need to address the dementia associated with Down's syndrome.

Genetically programmed degeneration of neurons in certain areas of the brain cause Huntington's disease. Early symptoms of Huntington's disease include mood swings, or trouble learning new things or remembering a fact. Most drugs used to treat the symptoms of Huntington's disease have side effects such as fatigue, restlessness, or hyperexcitability. Currently, there is no treatment to stop or reverse the progression of Huntington's disease. Therefore, there is a need of a pharmaceutical agent to address the symptoms with fewer side effects.

Dementia with Lewy Bodies is a neurodegenerative disorder involving abnormal structures known as Lewy bodies found in certain areas of the brain. Symptoms of dementia with Lewy bodies include, but are not limited to, fluctuating cognitive impairment with episodic delirium. Currently, treatment concerns addressing the parkinsonian and psychiatric symptoms. However, medicine to control tremors or loss of muscle movement may actually accentuate the underlying disease of dementia with Lewy bodies. Therefore, there is a need of a pharmaceutical agent to treat dementia with Lewy bodies.

Parkinson's disease is a neurological disorder characterized by tremor, hypokinesia, and muscular rigidity. Currently, there is no treatment to stop the progression of the disease. Therefore, there is a need of a pharmaceutical agent to address Parkinson's.

Tardive dyskinesia is associated with the use of conventional antipsychotic drugs. This disease is characterized by involuntary movements most often manifested by puckering of the lips and tongue and/or writhing of the arms or legs. The incidence of tardive dyskinesia is about 5% per year of drug exposure among patients taking conventional antipsychotic drugs. In about 2% of persons with the disease, tardive dyskinesia is severely disfiguring. Currently, there is no generalized treatment for tardive dyskinesia. Furthermore, the removal of the effect-causing drugs is not always an option due to underlying problems. Therefore, there is a need for a pharmaceutical agent to address the symptoms of tardive dyskinesia.

Pick's disease results from a slowly progressive deterioration of social skills and changes in personality with the resulting symptoms being impairment of intellect, memory, and language. Common symptoms include memory loss, lack of spontaneity, difficulty in thinking or concentrating, and speech disturbances. Currently, there is no specific treatment or cure for Pick's disease but some symptoms can be treated with cholinergic and serotonin-boosting antidepressants. In addition, antipsychotic medications may alleviate symptoms in FTD patients who are experiencing delusions or hallucinations. Therefore, there is a need for a pharmaceutical agent to treat the progressive deterioration of social skills and changes in personality and to address the symptoms with fewer side effects.

Dysregulation of food intake associated with eating disease, including bulemia nervosa and anorexia nervosa, involve neurophysiological pathways. Anorexia nervosa is hard to treat due to patients not entering or remaining in after entering programs. Currently, there is no effective treatment for persons suffering from severe anorexia nervosa. Cognitive behavioral therapy has helped patients suffering from bulemia nervosa; however, the response rate is only about 50% and current treatment does not adequately address emotional regulation. Therefore, there is a need for pharmaceutical agents to address neurophysiological problems underlying diseases of dysregulation of food intake.

Cigarette smoking has been recognized as a major public health problem for a long time. However, in spite of the public awareness of health hazard, the smoking habit remains extraordinarily persistent and difficult to break. There are many treatment methods available, and yet people continue to smoke. Administration of nicotine transdermally, or in a chewing gum base is common treatments. However, nicotine has a large number of actions in the body, and thus can have many side effects. It is clear that there is both a need and a demand of long standing for a convenient and relatively easy method for aiding smokers in reducing or eliminating cigarette consumption. A drug that could selectively stimulate only certain of the nicotinic receptors would be useful in smoke cessation programs.

Smoke cessation programs may involve oral dosing of the drug of choice. The drug may be in the form of tablets. However, it is preferred to administer the daily dose over the waking hours, by administration of a series of incremental doses during the day. The preferred method of such administration is a slowly dissolving lozenge, troche, or chewing gum, in which the drug is dispersed. Another drug in treating nicotine addiction is Zyban. This is not a nicotine replacement, as are the gum and patch. Rather, this works on other areas of the brain, and its effectiveness is to help control nicotine craving or thoughts about cigarette use in people trying to quit. Zyban is not very effective and effective drugs are needed to assist smokers in their desire to stop smoking. These drugs may be administered transdermally through the use of skin patches. In certain cases, the drugs may be administered by subcutaneous injection, especially if sustained release formulations are used.

Drug use and dependence is a complex phenomenon, which cannot be encapsulated within a single definition. Different drugs have different effects, and therefore different types of dependence. Drug dependence has two basic causes, that is, tolerance and physical dependence. Tolerance exists when the user must take progressively larger doses to produce the effect originally achieved with smaller doses. Physical dependence exists when the user has developed a state of physiologic adaptation to a drug, and there is a withdrawal (abstinence) syndrome when the drug is no longer taken. A withdrawal syndrome can occur either when the drug is discontinued or when an antagonist displaces the drug from its binding site on cell receptors, thereby counteracting its effect. Drug dependence does not always require physical dependence.

In addition drug dependence often involves psychological dependence, that is, a feeling of pleasure or satisfaction when taking the drug. These feelings lead the user to repeat the drug experience or to avoid the displeasure of being deprived of the drug. Drugs that produce strong physical dependence, such as nicotine, heroin and alcohol are often abused, and the pattern of dependence is difficult to break. Drugs that produce dependence act on the CNS and generally reduce anxiety and tension; produce elation, euphoria, or other pleasurable mood changes; provide the user feelings of increased mental and physical ability; or alter sensory perception in some pleasurable manner. Among the drugs that are commonly abused are ethyl alcohol, opioids, anxiolytics, hypnotics, cannabis (marijuana), cocaine, amphetamines, and hallucinogens. The current treatment for drug-addicted people often involves a combination of behavioral therapies and medications. Medications, such as methadone or LAAM (levo-alpha-acetyl-methadol), are effective in suppressing the withdrawal symptoms and drug craving associated with narcotic addiction, thus reducing illicit drug use and improving the chances of the individual remaining in treatment. The primary medically assisted withdrawal method for narcotic addiction is to switch the patient to a comparable drug that produces milder withdrawal symptoms, and then gradually taper off the substitute medication. The medication used most often is methadone, taken orally once a day. Patients are started on the lowest dose that prevents the more severe signs of withdrawal and then the dose is gradually reduced. Substitutes can be used also for withdrawal from sedatives. Patients can be switched to long-acting sedatives, such as diazepam or phenobarbital, which are then gradually reduced.

Gilles de la Tourette's Syndrome is an inherited neurological disorder. The disorder is characterized by uncontrollable vocal sounds called tics and involuntary movements. The symptoms generally manifest in an individual before the person is 18 years of age. The movement disorder may begin with simple tics that progress to multiple complex tics, including respiratory and vocal ones. Vocal tics may begin as grunting or barking noises and evolve into compulsive utterances. Coprolalia (involuntary scatologic utterances) occurs in 50% of patients. Severe tics and coprolalia may be physically and socially disabling. Tics tend to be more complex than myoclonus, but less flowing than choreic movements, from which they must be differentiated. The patient may voluntarily suppress them for seconds or minutes.

Currently simple tics are often treated with benzodiazepines. For simple and complex tics, Clonidine may be used. Long-term use of Clonidine does not cause tardive dyskinesia; its limiting adverse effect is hypotension. In more severe cases, antipsychotics, such as Haloperidol may be required, but side effects of dysphoria, parkinsonism, akathisia, and tardive dyskinesia may limit use of such antipsychotics. There is a need for safe and effective methods for treating this syndrome.

Age-related macular degeneration (AMD) is a common eye disease of the macula which is a tiny area in the retina that helps produce sharp, central vision required for "straight ahead" activities that include reading and driving. Persons with AMD lose their clear, central vision. AMD takes two forms: wet and dry. In dry AMD, there is a slow breakdown of light-sensing cells in the macula. There currently is no cure for dry AMD. In wet AMD, new, fragile blood vessels growing beneath the macula as dry AMD worsens and these vessels often leak blood and fluid to cause rapid damage to the macula quickly leading to the loss of central vision. Laser surgery can treat some cases of wet AMD. Therefore, there is a need of a pharmaceutical agent to address AMD.

Glaucoma is within a group of diseases occurs from an increase in intraocular pressure causing pathological changes in the optical disk and negatively affects the field of vision. Medicaments to treat glaucoma either decrease the amount of fluid entering the eye or increase drainage of fluids from the eye in order to decrease intraocular pressure. However, current drugs have drawbacks such as not working over time or causing side effects so the eye-care professional has to either prescribe other drugs or modify the prescription of the drug being used. There is a need for safe and effective methods for treating problems manifesting into glaucoma.

Ischemic periods in glaucoma cause release of excitotoxic amino acids and stimulate inducible form of nitric oxide synthase (iNOS) leading to neurodegeneration. Alpha 7 nicotinic agonists may stimulate the release of inhibitory amino acids such as GABA which will dampen hyperexcitablity. Alpha 7 nicotinic agonists are also directly neuroprotective on neuronal cell bodies. Thus alpha 7 nicotinic agonists have the potential to be neuroprotective in glaucoma.

Persons afflicted with pain often have what is referred to as the "terrible triad" of suffering from the pain, resulting in sleeplessness and sadness, all of which are hard on the afflicted individual and that individual's family. Pain can manifest itself in various forms, including, but not limited to, headaches of all severity, back pain, neurogenic, and pain from other ailments such as arthritis and cancer from its existence or from therapy to irradicate it. Pain can be either chronic (persistent pain for months or years) or acute (short-lived, immediate pain to inform the person of possible injury and need of treatment). Persons suffering from pain respond differently to individual therapies with varying degrees of success. There is a need for safe and effective methods for treating pain.

Finally, the compounds of the present invention may be used in combination therapy with typical and atypical anti-psychotic drugs (also called an anti-psychotic agent). All compounds within the present invention are useful for and may also be used in combination with each other to prepare pharmaceutical compositions. Such combination therapy lowers the effective dose of the anti-psychotic drug and thereby reduces the side effects of the anti-psychotic drugs. Some typical anti-psychotic drugs that may be used in the practice of the invention include Haldol. Some atypical anti-psychotic drugs include Ziprasidone, Olanzapine, Resperidone, and Quetiapine.

Compounds of Formula I can be prepared as shown in Scheme 1. The key step in the preparation of this class of compounds is the coupling of an azabicyclic moiety with the requisite acid chloride (Lv=Cl), mixed anhydride (e.g., Lv=diphenyl phosphoryl, bis(2-oxo-3-oxazolidinyl) phosphinyl, or acyloxy of the general formula of O—C(O)—$R_{Lv}$, where $R_{Lv}$ includes phenyl or t-butyl), or carboxylic acid (Lv=OH) in the presence of an activating reagent. Suitable activating reagents are well known in the art, for examples see Kiso, Y., Yajima, H. "Peptides" pp. 39–91, San Diego, Calif., Academic Press, (1995), and include, but are not limited to, agents such as carbodiimides, phosphonium and uronium salts (such as HATU).

Scheme I

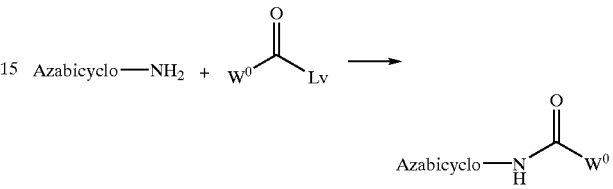

Generally, for most Azabicyclo moieties, the acid is activated using HATU or is converted to the acyl azide by using DPPA. The appropriate amine precursor is added to a solution of the appropriate anhydride or azide to give the desired final compounds. In some cases, the ester (Lv being OMe or OEt) may be reacted directly with the amine precursor in refluxing methanol or ethanol to give the compounds of Formula I.

Preferably, for Azabicyclo V, the acid is converted into a mixed anhydride by treatment with bis (2-oxo-3-oxazolidinyl) phosphinic chloride in the presence of TEA with $CH_2Cl_2$ or $CHCl_3$ as the solvent. The resulting anhydride solution is directly reacted with 1-azabicyclo[3.2.1] octan-3-amine added neat or using DMF or aqueous DMF as solvent. In some cases, the ester (Lv being OMe or OEt) may be reacted directly with the amine in refluxing methanol or ethanol to give the compounds of Formula I.

Certain 6-substituted-[2.2.2]-3-amines (Azabicyclo I) are known in the art. The preparation of compounds where $R_2$ is other than H is described in *Acta Pol. Pharm.* 179–85 (1981). Alternatively, the 6-substituted-[2.2.2]-3-amine can be prepared by reduction of an oxime or an imine of the corresponding 6-substituted-3-quinuclidinone by methods known to one of ordinary skill in the art (see *J. Labelled Compds. Radiopharm.*, 53–60 (1995), *J. Med. Chem.* 988–995, (1998), *Synth. Commun.* 1895–1911 (1992), *Synth. Commun.* 2009–2015 (1996)). Alternatively, the 6-substituted-[2.2.2]-3-amine can be prepared from a 6-substituted-3-hydroxyquinuclidine by Mitsunobu reaction followed by deprotection as described in *Synth. Commun.* 1895–1911 (1995). Alternatively, the 6-substituted-[2.2.2]-3-amine can be prepared by conversion of a 6-substituted-3-hydroxyquinuclidine into the corresponding mesylate or tosylate, followed by displacement with sodium azide and reduction as described in *J. Med. Chem.* 587–593 (1975).

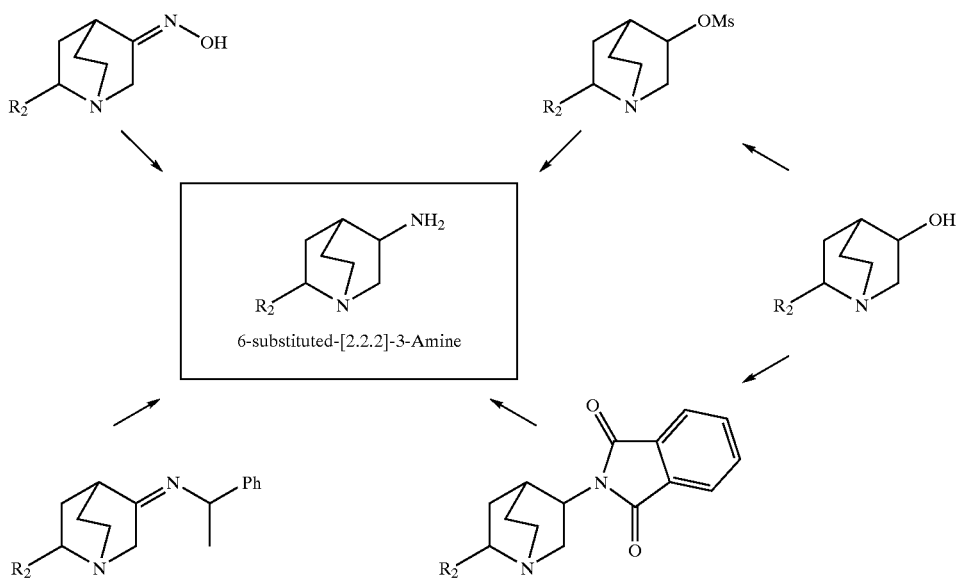

The oximes can be prepared by treatment of the 3-quinuclidinones with hydroxylamine hydrochloride in the presence of base. The imines can be prepared by treatment of the 3-quinuclidinones with a primary amine under dehydrating conditions. The 3-hydroxyquinuclidines can be prepared by reduction of the 3-quinuclidinones. The 6-substituted-3-quinuclidinones can be prepared by known procedures (see *J. Gen. Chem. Russia* 3791–3795, (1963), *J. Chem. Soc. Perkin Trans. I* 409–420 (1991), *J. Org. Chem.* 3982–3996 (2000)).

53, p. 11121 as shown below. Methods to synthesize nitro alcohols are well known in the art (see *J. Am. Chem. Soc.* (1947), 69, p 2608). The scheme below is a modification of the synthesis of exo-3-amino-1-azabicyclo[2.2.1]heptane as the bis(hydro para-toluenesulfonate) salt, described in detail herein, to show how to obtain these amine precursors. The desired salt can be made using standard procedures.

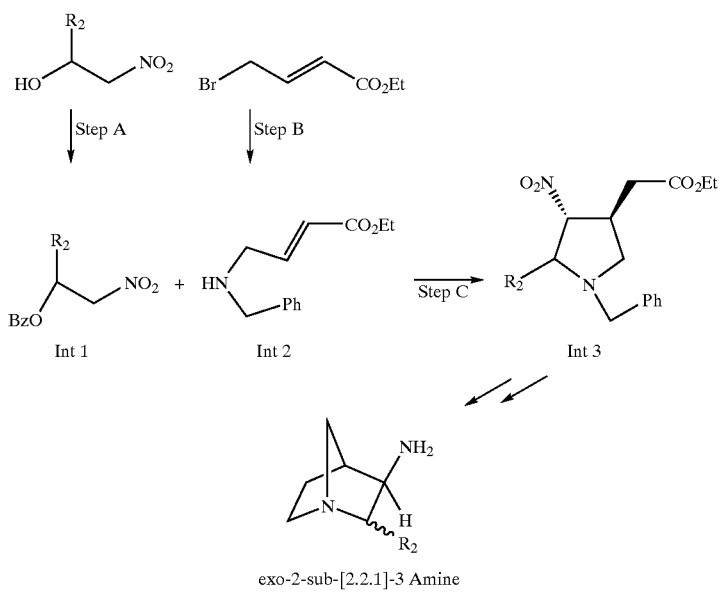

One of ordinary skill in the art will recognize that the methods described for the reaction of the unsubstituted 3-amino-1-azabicyclo[2.2.1]heptane ($R_2$=absent) are equally applicable to substituted compounds ($R_2 \approx H$). For where Azabicyclo is II, compounds where $R_2$ is other than H can be prepared from appropriately substituted nitro alcohols using procedures described in *Tetrahedron* (1997), Compounds for Azabicyclo II where $R_2$ is other than H can also be prepared by modification of intermediates described in the synthesis of exo-3-amino-1-azabicyclo [2.2.1]heptane as the bis(hydro para-toluenesulfonate) salt, described in detail herein. For example, Int 6 can be oxidized to the aldehyde and treated with an organometallic reagent to provide Int 20 using procedures described in *Tetrahedron*

(1999), 55, p 13899. Int 20 can be converted into the amine using methods described for the synthesis of exo-3-amino-1-azabicyclo[2.2.1]heptane as the bis(hydro para-toluenesulfonate) salt. Once the amine is obtained, the desired salt can be made using standard procedures.

The schemes used are for making exo-3-amino-1-azabicyclo[2.2.1]heptane. However, the modifications discussed are applicable to make the endo isomer also.

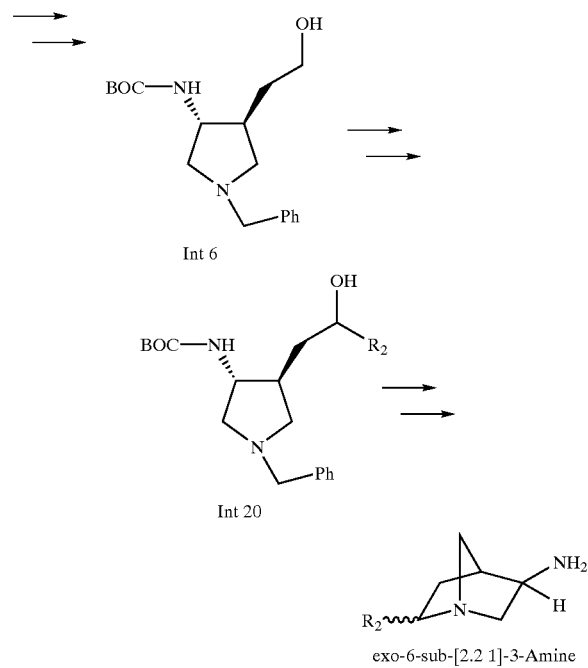

Int 6

Int 20 exo-6-sub-[2.2 1]-3-Amine

There are several methods by which the amine precursor for Azabicyclo III and Azabicyclo IV can be obtained.

N-(2-azabicyclo[2.2.1]hept)-5-amine and 6-amine

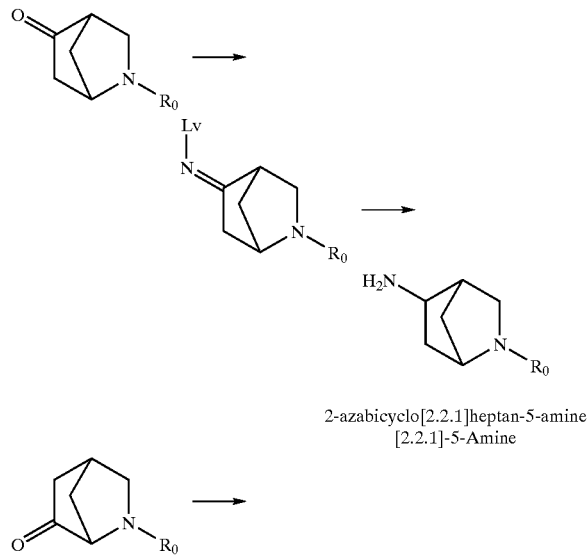

2-azabicyclo[2.2.1]heptan-5-amine
[2.2.1]-5-Amine

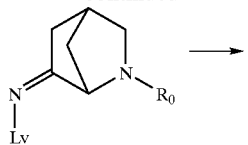

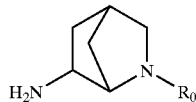

2-azabicyclo[2.2.1]heptan-6-amine
[2.2.1]-6-Amine where Lv can be —CH$_2$Ph, —CH(Me)Ph, —OH, —OMe, or —OCH$_2$Ph.

The respective amine precursors for Azabicyclo III and Azabicyclo IV can be prepared by reduction of an oxime or an imine of the corresponding N-2-azabicyclo[2.2.1]-heptanone by methods known to one skilled in the art (see J. Labelled Compds. Radiopharm., 53–60 (1995), J. Med. Chem. 988–995, (1998), Synth. Commun. 1895–1911 (1992), Synth. Commun. 2009–2015 (1996)). The oximes can be prepared by treatment of the N-2-azabicyclo[2.2.1] heptanones with hydroxylamine hydrochloride in the presence of a base. The imines can be prepared by treatment of the N-2-azabicyclo[2.2.1]-heptanones with a primary amine under dehydrating conditions. The N-2-azabicyclo[2.2.1] heptanones can be prepared by known procedures (see Tet. Lett. 1419–1422 (1999), J. Med. Chem. 2184–2191 (1992), J. Med. Chem. 706–720 (2000), J. Org. Chem., 4602–4616 (1995)).

The exo- and endo-1-azabicyclo[3.2.1]octan-3-amines are prepared from 1-azabicyclic[3.2.1]octan-3-one (Thill, B. P., Aaron, H. S., J. Org. Chem., 4376–4380 (1968)) according to the general procedure as discussed in Lewin, A. H., et al., J. Med. Chem., 988–995 (1998).

One of ordinary skill in the art will also recognize that the methods described for the reaction of the unsubstituted 1-azabicyclo[3.2.1]octan-3-amine or 1-azabicyclo[3.2.2] nonan-3-amine (R$_2$=absent) are equally applicable to substituted compounds (R$_2$ present). The R$_2$ substituent may be introduced as known to one skilled in the art through standard alkylation chemistry. Exposure of 1-azabicyclo [3.2.1]octan-3-one or 1-azabicyclo[3.2.2]nonan-3-one to a hindered base such as LDA (lithium diisopropylamide) in a solvent such as THF or ether between 0° C. to −78° C. followed by the addition of an alkylating agent (R$_2$Lv, where Lv=Cl, Br, I, OTs, etc.) will, after being allowed to warm to about 0° C. to rt followed by an aqueous workup, provide the desired compound as a mixture of isomers. Chromatographic resolution (flash, HPLC, or chiral HPLC) will provided the desired purified alkylated ketones. From there, formation of the oxime and subsequent reduction will provide the desired endo or exo isomers.

It will be apparent to those skilled in the art that the requisite carboxylic acids can be obtained through synthesis via literature procedures or through the slight modification thereof.

Thioamides can be prepared from the requisite thioester by direct displacement of the thioester with an amino precursor of the Azabicyclo, for example, see Scheme 2. The thioester can be prepared as described in *J. Organometallic Chem.*, 95–98 (1987). One of ordinary skill in the art would quickly identify that said compounds could also be prepared directly from the amides exemplified throughout this patent by direct treatment with a reagent such and Lawesson's reagent (see Lawesson et. al. in *Bull. Soc. Chim. Belg.*, 229 (1978)) or $P_4S_{10}$ (see *Chem. Rev.*, 45 (1961)). Alternatively one can react a dithiocarboxylic ester with the corresponding amino-azabicyclo compound to form the same thioamide.

Furthermore, the examples provided are carried out using one amine. However, either amine could be used making non-critical changes but starting with the amine not identified. Therefore, the stereospecificity of the resulting compound is not drawn. But, the scope of this invention includes the four different stereoisomers as described herein as well as racemic mixtures.

Preparation of the 2.2.1 Amines

Synthesis of exo-3-amino-1-azabicyclo[2.2.1]heptane as the bis(hydro para-toluenesulfonate) salt:

Step B. Preparation of ethyl E-4-(benzylamino)-2-butenoate (Int 2).

Ethyl E-4-bromo-2-butenoate (10 mL, 56 mmol, tech grade) is added to a stirred solution of benzylamine (16 mL, 146 mmol) in $CH_2Cl_2$ (200 mL) at rt. The reaction mixture stirs for 15 min, and is diluted with ether (1 L). The mixture is washed with saturated aqueous $NaHCO_3$ solution (3×) and water, dried over $Na_2SO_4$, filtered and concentrated in vacuo. The residue is purified by flash chromatography on silica gel. Elution with hexanes-EtOAc (70:30) affords Int 2 as a clear oil (62% yield): $^1H$ NMR ($CDCl_3$) δ 7.4–7.2, 7.0, 6.0, 4.2, 3.8, 3.4, 2.1–1.8, 1.3.

Step C. Preparation of trans-4-nitro-1-(phenylmethyl)-3-pyrrolidineacetic acid ethyl ester (Int 3).

A solution of Int 1 (6.81 g, 34.9 mmol) and Int 2 (7.65 g, 34.9 mmol) in EtOH (70 mL) stirs at rt for 15 h and is then concentrated in vacuo. The residue is diluted with ether (100 mL) and saturated aqueous $NaHCO_3$ solution (100 mL). The organic layer is separated and dried over $Na_2SO_4$, filtered and concentrated in vacuo. The crude product is purified by flash chromatography on silica gel. Elution with hexanes-EtOAc (85:15) affords Int 3 as a clear oil (76% yield): $^1H$ NMR ($CDCl_3$) δ 7.4–7.3, 4.8–4.7, 4.1, 3.8–3.6, 3.3–3.0, 2.7–2.6, 2.4–2.3, 1.2.

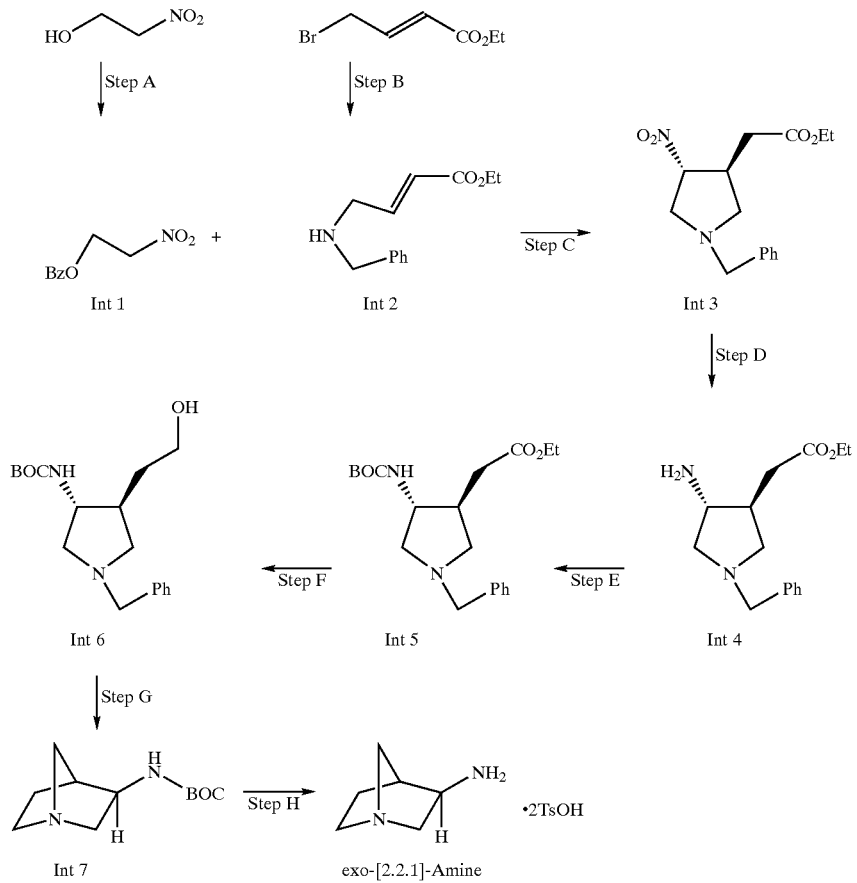

Step A. Preparation of 2-(benzoyloxy)-1-nitroethane (Int 1).

Benzoyl chloride (14.9 mL, 128 mmol) is added to a stirred solution of nitroethanol (9.2 mL, 128 mmol) in dry benzene (120 mL). The solution is refluxed for 24 hr and then concentrated in vacuo. The crude product is purified by flash chromatography on silica gel. Elution with hexanes-EtOAc (80:20) affords Int 1 as a white solid (68% yield): $^1H$ NMR ($CDCl_3$) δ 8.0, 7.6, 7.4, 4.9, 4.8.

Step D. Preparation of trans-4-amino-1-(phenylmethyl)-3-pyrrolidineacetic acid ethyl ester (Int 4).

A mixture of Int 3 (3.28 g, 11.2 mmol) and RaNi (1.5 g) in EtOH (100 mL) is placed in a Parr bottle and hydrogenated for 4 h under an atmosphere of hydrogen (46 psi) at rt. The mixture is filtered through a pad of Celite, and the solvent is removed in vacuo to afford Int 4 as a clear oil (100% yield): $^1H$ NMR (300 MHz, $CDCl_3$) δ 7.3–7.2, 4.1, 3.6, 3.2, 3.0–2.9, 2.8, 2.8–2.6, 2.6–2.4, 2.30–2.2, 1.2.

Step E. Preparation of trans-4-(1,1-dimethylethoxycarbonylamido-1-(phenylmethyl)-3-pyrrolidineacetic acid ethyl ester (Int 5).

Di-tert-butyldicarbonate (3.67 g, 16.8 mmol) is added to a stirred solution of Int 4 (2.94 g, 11.2 mmol) in $CH_2Cl_2$ (30 mL) cooled in an ice bath. The reaction is allowed to warm to rt and stirred overnight. The mixture is concentrated in vacuo. The crude product is purified by flash chromatography on silica gel. Elution with hexanes-EtOAc (80:20) affords Int 5 as a white solid (77% yield): $^1$H NMR (300 MHz, $CDCl_3$) δ 7.4–7.2, 5.1–4.9, 4.1, 4.0–3.8, 3.6, 3.2–3.0, 2.8–2.6, 2.5–2.4, 2.3–2.1, 1.4, 1.3.

Step F. Preparation of trans (tert-butoxycarbonylamino-4-(2-hydroxyethyl)-1-(N-phenylmethyl) pyrrolidine (Int 6).

$LiAlH_4$ powder (627 mg, 16.5 mmol) is added in small portions to a stirred solution of Int 5 (3.0 g, 8.3 mmol) in anhydrous THF (125 mL) in a −5° C. bath. The mixture is stirred for 20 min in a −5° C. bath, then quenched by the sequential addition of water (0.6 mL), 15% (w/v) aqueous NaOH (0.6 mL) and water (1.8 mL). Excess anhydrous $K_2CO_3$ is added, and the mixture is stirred for 1 h, then filtered. The filtrate is concentrated in vacuo. The residue is purified by flash chromatography on silica gel. Elution with EtOAc affords Int 6 as a white solid (94% yield): $^1$H NMR ($CDCl_3$) δ 7.4–7.3, 5.3–5.2, 4.1–4.0, 3.9–3.7, 3.3–3.2, 2.8–2.7, 2.3–2.1, 1.7, 1.5.

Int 6 is a racemic mixture that can be resolved via chromatography using a Diacel chiral pack AD column. From the two enantiomers thus obtained, the (+)-enantiomer, $[\alpha]^{25}_D$+35 (c 1.0, MeOH), gives rise to the corresponding optically pure exo-4-S final compounds, whereas the (−)-enantiomer, $[\alpha]^{25}_D$−34 (c 0.98, MeOH), gives rise to optically pure exo-4-R final compounds. The methods described herein use the (+)-enantiomer of Int 6 to obtain the optically pure exo-4-S final compounds. However, the methods used are equally applicable to the (−)-enantiomer of Int 6, making non-critical changes to the methods provided herein to obtain the optically pure exo-4-R final compounds.

Step G. Preparation of exo 3-(tert-butoxycarbonylamino-1-azabicyclo[2.2.1]heptane (Int 7).

TEA (8.0 g, 78.9 mml) is added to a stirred solution of Int 6 (2.5 g, 7.8 mmol) in $CH_2Cl_2$ (50 mL), and the reaction is cooled in an ice-water bath. $CH_3SO_2Cl$ (5.5 g, 47.8 mmol) is then added dropwise, and the mixture is stirred for 10 min in an ice-water bath. The resulting yellow mixture is diluted with saturated aqueous $NaHCO_3$ solution, extracted with $CH_2Cl_2$ several times until no product remains in the aqueous layer by TLC. The organic layers are combined, washed with brine, dried over $Na_2SO_4$ and concentrated in vacuo. The residue is dissolved in EtOH (85 mL) and is heated to reflux for 16 h. The reaction mixture is allowed to cool to rt, transferred to a Parr bottle and treated with 10% Pd/C catalyst (1.25 g). The bottle is placed under an atmosphere of hydrogen (53 psi) for 16 h. The mixture is filtered through Celite, and fresh catalyst (10% Pd/C, 1.25 g) is added. Hydrogenolysis continues overnight. The process is repeated three more times until the hydrogenolysis is complete. The final mixture is filtered through Celite and concentrated in vacuo. The residue is purified by flash chromatography on silica gel. Elution with $CHCl_3$—MeOH—$NH_4OH$ (90:9.5:0.5) affords Int 7 as a white solid (46% yield): $^1$H NMR ($CDCl_3$) δ 5.6–5.5, 3.8–3.7, 3.3–3.2, 2.8–2.7, 2.0–1.8, 1.7–1.5, 1.5.

Step H. Preparation of exo-3-amino-1-azabicyclo[2.2.1]heptane bis(hydro-para-toluenesulfonate).

Para-toluenesulfonic acid monohydrate (1.46 g, 7.68 mmol) is added to a stirred solution of Int 7 (770 mg, 3.63 mmol) in EtOH (50 mL). The reaction mixture is heated to reflux for 10 h, followed by cooling to rt. The precipitate is collected by vacuum filtration and washed with cold EtOH to give exo-[2.2.1]-Amine as a white solid (84% yield): $^1$H NMR ($CD_3OD$) δ 7.7, 7.3, 3.9–3.7, 3.7–3.3, 3.2, 2.4, 2.3–2.2, 1.9–1.8. The corresponding amines can be obtained by using the resolved Int 6 to give exo-(4R)-[2.2.1]-3-Amine and exo-(4S)-[2.2.1]-3-Amine.

Synthesis of endo-3-amino-1-azabicyclo[2.2.1]heptane as the bis(hydro para-toluenesulfonate) salt:

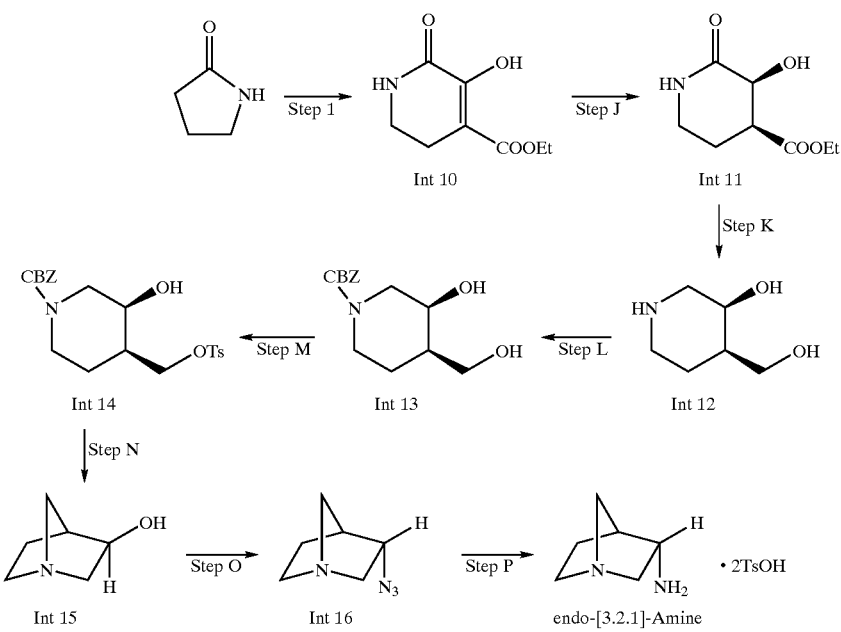

Step I. Preparation of ethyl 5-hydroxy-6-oxo-1,2,3,6-tetrahydropyridine-4-carboxylate (Int 10).

Absolute EtOH (92.0 mL, 1.58 mol) is added to a mechanically stirred suspension of potassium ethoxide (33.2 g, 395 mmol) in dry toluene (0.470 L). When the mixture is homogeneous, 2-pyrrolidinone (33.6 g, 395 mmol) is added, and then a solution of diethyl oxalate (53.1 mL, 390 mmol) in toluene (98 mL) is added via an addition funnel. After complete addition, toluene (118 mL) and EtOH (78 mL) is added sequentially. The mixture is heated to reflux for 18 h. The mixture is cooled to rt and aqueous HCl (150 mL of a 6.0 M solution) is added. The mixture is mechanically stirred for 15 min. The aqueous layer is extracted with $CH_2Cl_2$, and the combined organic layers are dried over $MgSO_4$, filtered and concentrated in vacuo to a yellow residue. The residue is recrystallized from EtOAc to afford Int 10 as a yellow solid (38% yield): $^1H$ NMR ($CDCl_3$) δ 11.4, 7.4, 4.3, 3.4, 2.6, 1.3.

Step J. Preparation of ethyl cis-3-hydroxy-2-oxopiperidine-4-carboxylate (Int 11).

A mixture of Int 10 (15 g, 81 mmol) and 5% rhodium on carbon (2.0 g) in glacial acetic acid is placed under an atmosphere of hydrogen (52 psi). The mixture is shaken for 72 h. The mixture is filtered through Celite, and the filtrate is concentrated in vacuo to afford Int 11 as a white solid (98% yield): $^1H$ NMR ($CDCl_3$) δ 6.3, 4.2, 4.0–3.8, 3.4, 3.3–3.2, 2.2, 1.3.

Step K. Preparation of cis-4-(hydroxymethyl)piperidin-3-ol (Int 12).

Int 11 (3.7 g, 19.9 mmol) as a solid is added in small portions to a stirred solution of $LiAlH_4$ in THF (80 mL of a 1.0 M solution) in an ice-water bath. The mixture is warmed to rt, and then the reaction is heated to reflux for 48 h. The mixture is cooled in an ice-water bath before water (3.0 mL, 170 mmol) is added dropwise, followed by the sequential addition of NaOH (3.0 mL of a 15% (w/v) solution) and water (9.0 mL, 500 mmol). Excess $K_2CO_3$ is added, and the mixture is stirred vigorously for 15 min. The mixture is filtered, and the filtrate is concentrated in vacuo to afford Int 12 as a yellow powder (70% yield): $^1H$ NMR (DMSO-$d_6$) δ 4.3, 4.1, 3.7, 3.5–3.2, 2.9–2.7, 2.5–2.3, 1.5, 1.3.

Step L. Preparation of benzyl cis-3-hydroxy-4-(hydroxymethyl)piperidine-1-carboxylate (Int 13).

N-(benzyloxy carbonyloxy)succinimide (3.04 g, 12.2 mmol) is added to a stirred solution of Int 12 (1.6 g, 12.2 mmol) in saturated aqueous $NaHCO_3$ (15 mL) at rt. The mixture is stirred at rt for 18 h. The organic and aqueous layers are separated. The aqueous layer is extracted with ether (3×). The combined organic layers are dried over anhydrous $K_2CO_3$, filtered and concentrated in vacuo to afford Int 13 as a yellow oil (99% yield): $^1H$ NMR ($CDCl_3$) δ 7.4–7.3, 5.2, 4.3, 4.1, 3.8–3.7, 3.0–2.8, 2.1, 1.9–1.7, 1.4.

Step M. Preparation of benzyl cis-3-hydroxy-4-[(4-methylphenyl)sulfonyl oxymethyl]piperidine-1-carboxylate (Int 14).

Para-toluenesulfonyl chloride (1.0 g, 5.3 mmol) is added to a stirred solution of Int 13 (3.6 g, 5.3 mmol) in pyridine (10 mL) in a −15° C. bath. The mixture is stirred for 4 h, followed by addition of HCl (4.5 mL of a 6.0 M solution). $CH_2Cl_2$ (5 mL) is added. The organic and aqueous layers are separated. The aqueous layer is extracted with $CH_2Cl_2$. The combined organic layers are washed with brine, dried over $MgSO_4$, filtered and concentrated in vacuo to afford Int 14 as a colorless oil (78% yield): $^1H$ NMR ($CDCl_3$) δ 7.8, 7.4–7.2, 5.1, 4.3–4.2, 4.1, 3.9–3.8, 2.9–2.7, 2.4, 1.9, 1.6–1.3.

Step N. Preparation of exo-1-azabicyclo[2.2.1]heptan-3-ol (Int 15).

A mixture of Int 14 (3.6 g, 8.6 mmol) and 10% Pd/C catalyst (500 mg) in EtOH (50 mL) is placed under an atmosphere of hydrogen. The mixture is shaken for 16 h. The mixture is filtered through Celite. Solid $NaHCO_3$ (1.1 g, 13 mmol) is added to the filtrate, and the mixture is heated in an oil bath at 50° C. for 5 h. The solvent is removed in vacuo. The residue is dissolved in saturated aqueous $K_2CO3$ solution. Continuous extraction of the aqueous layer using a liquid-liquid extraction apparatus (18 h), followed by drying the organic layer over anhydrous $K_2CO_3$ and removal of the solvent in vacuo affords Int 15 as a white solid (91% yield): $^1H$ NMR δ 3.8, 3.0–2.8, 2.6–2.5, 2.4–2.3, 1.7, 1.1.

Step O. Preparation of endo-3-azido-1-azabicyclo[2.2.1]heptane (Int 16).

To a mixture of Int 15 (1.0 g, 8.9 mmol) and triphenyl phosphine (3.0 g, 11.5 mmol) in toluene-THF (50 mL, 3:2) in an ice-water bath are added sequentially a solution of hydrazoic acid in toluene (15 mL of ca. 2 M solution) and a solution of diethyl azadicarboxylate (1.8 mL, 11.5 mmol) in toluene (20 mL). The mixture is allowed to warm to rt and stir for 18 h. The mixture is extracted with aqueous 1.0M HCl solution. The aqueous layer is extracted with EtOAc, and the combined organic layers are discarded. The pH of the aqueous layer is adjusted to 9 with 50% aqueous NaOH solution. The aqueous layer is extracted with $CH_2Cl_2$ (3×), and the combined organic layers are washed with brine, dried over $Na_2SO_4$, filtered and concentrated in vacuo. The crude product is purified by flash chromatography on silica gel. Elution with $CHCl_3$—MeOH—$NH_4OH$ (92:7:1) affords Int 16 as a colorless oil (41% yield): $^1H$ NMR ($CDCl_3$) δ 4.1, 3.2, 2.8, 2.7–2.5, 2.2, 1.9, 1.5.

Step P. Preparation of endo-3-amino-1-azabicyclo[2.2.1]heptane bis(hydro-para-toluenesulfonate).

A mixture of Int 16 (250 mg, 1.8 mmol) and 10% Pd/C catalyst (12 mg) in EtOH (10 mL) is placed under an atmosphere of hydrogen (15 psi). The mixture is stirred for 1 h at rt. The mixture is filtered through Celite, and the filtrate is concentrated in vacuo. The residue is dissolved in EtOH (10 mL) and para-toluenesulfonic acid monohydrate (690 mg, 3.7 mmol) is added. The mixture is stirred for 30 min, and the precipitate is filtered. The precipitate is washed sequentially with cold EtOH and ether. The precipitate is dried in vacuo to afford endo-[2.2.1]-Amine as a white solid (85% yield): $^1H$ NMR ($CD_3OD$) δ 7.7, 7.3, 4.2, 3.9, 3.6–3.4, 3.3–3.2, 2.4, 2.3, 2.1.

Preparation of the 3.2.1-Amine exo-1-Azabicyclo[3.2.1]octan-3-amine dihydrochloride (exo-[3.2.1]-Amine):

A mixture of 1-azabicyclo[3.2.1]octan-3-one hydrochloride (2.80 g, 17.3 mmol), ethanol (25 mL), and hydroxylamine hydrochloride (1.56 g, 22.4 mmol) is treated with sodium acetate trihydrate (7.07 g, 51.2 mmol). The mixture is stirred for 3 h and evaporated in vacuo. The residue is diluted with $CH_2Cl_2$, treated with charcoal, filtered and evaporated. The resulting material is taken up in 1-propanol (45 mL) and heated in a 100° C. oil bath. The solution is treated with sodium metal (6.4 g in portions). Heating is continued for 3 h and the mixture cooled to rt. Water is added carefully and the organic layer is extracted, dried ($MgSO_4$), filtered, acidified with MeOH/HCl(g), and evaporated. 2-Propanol is added and the resulting solid is filtered and dried in vacuo to give exo-[3.2.1]-Amine in 49% yield. MS for $C_7H_{14}N_2 \cdot (HCl)_2$ (ESI) $(M+H)^+$ m/z=127.

endo-1-Azabicyclo[3.2.1]octan-3-amine dihydrochloride (endo-[3.2.1]-Amine):

A mixture of 1-azabicyclo[3.2.1]octan-3-one hydrochloride (2.80 g, 17.3 mmol), ethanol (25 mL), and hydroxylamine hydrochloride (1.56 g, 22.4 mmol) is treated with sodium acetate trihydrate (7.07 g, 51.2 mmol). The mixture is stirred for 3 h and evaporated in vacuo. The residue is diluted with CH$_2$Cl$_2$, treated with charcoal, filtered and evaporated. The resulting oxime (3.1 mmol) is treated with acetic acid (30 mL) and hydrogenated at 50 psi over PtO$_2$ (50 mg) for 12 h. The mixture is then filtered and evaporated. The residue is taken up in a minimal amount of water (6 mL) and the pH is adjusted to >12 using solid NaOH. The mixture is then extracted with ethyl acetate (4×25 mL), dried over MgSO$_4$, filtered, treated with ethereal HCl, and evaporated to give endo-[3.2.1]-Amine.

1-Azabicyclo[3.2.1]octan-3-amine

Preparation of the 3R,5R-[3.2.1]-Amine

This amine can also be prepared according to the following method:
(3S)-1-[(S)-1-Phenethyl]-5-oxo-3-pyrrolidine-carboxylic acid:

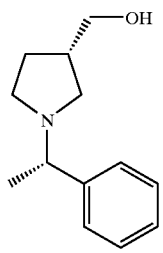

According to the literature procedure (Nielsen et al. J. Med. Chem 1990, 70–77), a mixture of itaconic acid (123.17 g, 946.7 mmol) and (S)-(−)-α-methyl benzylamine (122.0 mL, 946.4 mmol) are heated (neat) in a 160° C. oil bath for 4 h. Upon cooling, MeOH (~200 mL) is added and the resulting solid collected by filtration. The solid is treated with EtOH (~700 mL) and warmed using a steam bath until ~450 mL solvent remained. After cooling to rt, the solid is collected and dried to afford 83.2 g as a crystalline solid: [α]$^{25}_D$=−80 (c 0.97, DMSO). $^1$H NMR (400 MHz, DMSO-d$_6$) δ 12.66, 7.20–7.40, 5.23, 3.40–3.55, 3.10–3.25, 2.40–2.65, 1.45; MS (EI) m/z 233 (M$^+$).
(3S)-1-[(S)-1-Phenethyl]-3-(hydroxymethyl)pyrrolidine:

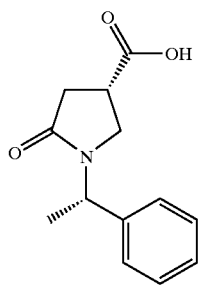

A suspension (3S)-1-[(S)-1-phenethyl]-5-oxo-3-pyrrolidine-carboxylic acid (82.30 g, 352.8 mmol) in Et$_2$O (200 mL) is added in small portions to a slurry of LiAlH$_4$ (17.41 g, 458.6 mmol) in Et$_2$O (700 mL). The mixture begins to reflux during the addition. The addition funnel containing the suspension is rinsed with Et$_2$O (2×50 mL), and the mixture is heated in a 50° C. oil bath for an additional 2 h and first allowed to cool to rt and then further cooled using an ice bath. The mixture is carefully treated with H$_2$O (62 mL). The resulting precipitate is filtered, rinsed with Et$_2$O, and discarded. The filtrate is concentrated to a yellow oil. When EtOAc is added to the oil, a solid began to form. Hexane is then added, and the mixture is filtered and the solid is dried to afford 43.3 g. [α]$^{25}_D$=−71 (c 0.94, CHCl$_3$); $^1$H NMR (400 MHz, CDCl$_3$) δ 7.20–7.45, 3.60–3.70, 3.40–3.60, 3.19, 3.05–3.15, 2.35–2.55, 2.25–2.35, 1.95–2.10, 1.75–1.90, 1.42; HRMS (FAB) calcd for C$_{13}$H$_{19}$NO (MH$^+$) 206.1545, found 206.1532.

(3R)-1-[(S)-1-Phenethyl]-3-(cyanomethyl)pyrrolidine:

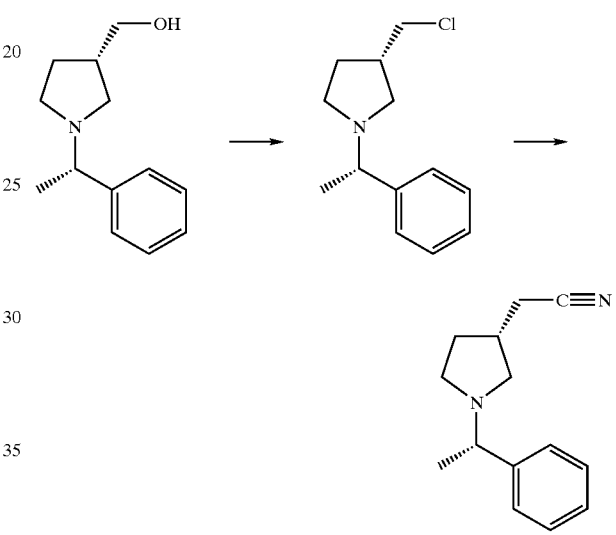

A solution of (3S)-1-[(S)-1-phenethyl]-3-(hydroxymethyl)pyrrolidine (42.75 g, 208.23 mmol) in chloroform (350 mL) is heated to reflux under N$_2$. The solution is treated with a solution of thionyl chloride (41.8 mL, 573 mmol) in chloroform (40 mL) dropwise over 45 min. The mixture is stirred for an additional 30 min, is cooled and concentrated. The residue is diluted with H$_2$O (~200 mL), 1 N NaOH is added until a pH~8 (pH paper). A small portion (~50 mL) of sat. NaHCO$_3$ is added and the basic mixture is extracted with EtOAc (3×400 mL), washed with brine, dried over MgSO$_4$, filtered and concentrated to give 46.51 g of (3S)-1-[(S)-1-phenethyl]-3-(chloromethyl)pyrrolidine: MS (ESI+) m/z 224.2 (MH$^+$). The chloride (46.35 g, 208.0 mmol) is transferred to a flask, DMSO (200 mL) is added, and the solution is treated with NaCN (17.84 g, 363.9 mmol). The mixture is heated under N$_2$ in a 100° C. oil bath overnight and is cooled. The brown mixture is poured into H$_2$O (300 mL) and is extracted with EtOAc (1000 mL in portions). The combined organic layer is washed with H$_2$O (6×~50 mL), brine (~100 mL), dried (MgSO$_4$), filtered and concentrated to give 40.61 g of an oil: $^1$H NMR (400 MHz, CDCl$_3$) δ 7.20–7.40, 3.26, 2.70–2.85, 2.40–2.60, 2.27, 2.10–2.20, 1.50–1.70, 1.41; MS (ESI+) for m/z 215.2 (M+H$^+$).

(3R)-Methyl 1-[(S)-1-phenylethyl]pyrrolidine-3-acetate:

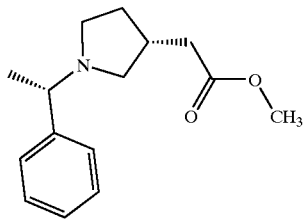

Acetyl chloride (270 mL, 3.8 mol) is carefully added to a flask containing chilled (0° C.) methanol (1100 mL). After the addition is complete, the acidic solution is stirred for 45 min (0° C.) and then (3R)-1-[(S)-1-phenethyl]-3-(cyanomethyl)pyrrolidine (40.50 g, 189.0 mmol) in methanol (200 mL) is added. The ice bath is removed and the mixture is stirred for 100 h at rt. The resulting suspension is concentrated. Water (~600 mL) is added, the mixture stirred for 45 min and then the pH is adjusted (made basic) through the addition of ~700 mL sat. aq. NaHCO$_3$. The mixture is extracted with EtOAc (3×300 mL). The combined organic layers are washed with brine, dried (MgSO$_4$), filtered through celite and concentrated to give 36.86 g as an oil: $^1$H NMR (400 MHz, CDCl$_3$) δ 7.20–7.40, 3.69, 3.30–3.40, 2.85–2.95, 2.40–2.70, 2.00–2.20, 1.10–1.65; MS (ESI+) m/z 248.2 (M+H$^+$).

(5R)-1-Azabicyclo[3.2.1]octan-3-one hydrochloride:

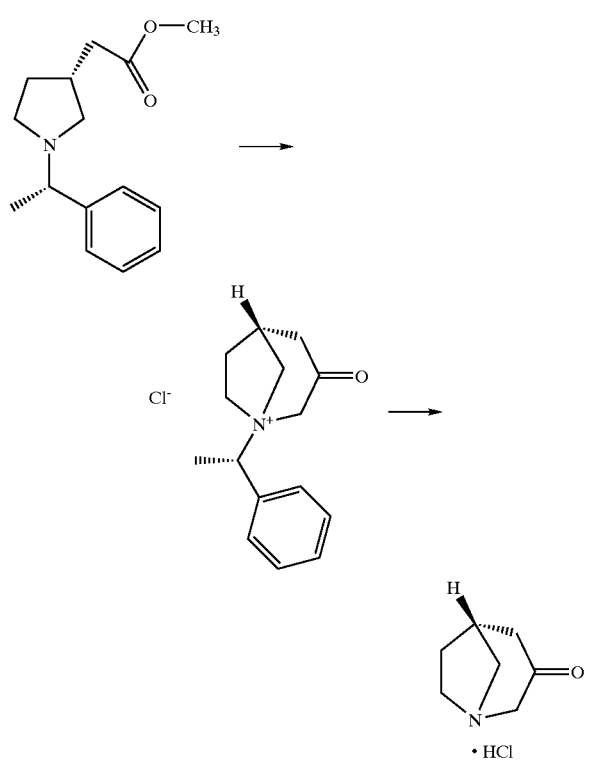

A solution of (3R)-methyl 1-[(S)-1-phenylethyl] pyrrolidine-3-acetate (25.72 g, 104.0 mmol) in THF (265 mL) is cooled under N$_2$ in a CO$_2$/acetone bath. Next, ICH$_2$Cl (22.7 mL, 312.0 mmol) is added, and the mixture stirred for 30 min. A solution of 2.0M lithium diisopropylamide (heptane/THF/ethylbenzene, 156 mL, 312 mmol) is added slowly over 30 min. The internal temperature reached a maximum of −40° C. during this addition. After 1 h, sat. NH$_4$Cl (100 mL) is added and the mixture is allowed to warm to rt. The organic layer is separated, dried (MgSO$_4$), filtered and concentrated. The resulting foam is chromatographed (300 g SiO$_2$, CHCl$_3$—MeOH—NH$_4$OH (89:10:1) followed by CHCl$_3$—MeOH (3:1). The product fractions are pooled and concentrated to afford (5R)-3-oxo-1-[(1S)-1-phenylethyl]-1-azoniabicyclo[3.2.1]octane chloride (10.12 g) as a foam (MS (ESI+) m/z 230.1 (M+H$^+$). This foam (10.1 g, 38 mmol) is taken up in MeOH (500 mL), 10% Pd(C) (3.0 g) added and the mixture is hydrogenated (45 psi) overnight. The mixture is filtered and re-subjected to the reduction conditions (9.1 g, 10% Pd/C, 50 psi). After 5 h, TLC indicates the consumption of the (5R)-3-oxo-1-[(1S)-1-phenylethyl]-1-azoniabicyclo[3.2.1]octane chloride. The mixture is filtered, concentrated and triturated (minimal iPrOH) to give 3.73 g in two crops, as a solid: $[\alpha]^{25}_D$=−33 (c 0.97, DMSO); HRMS (FAB) calcd for C$_7$H$_{11}$NO (M+H$^+$) 126.0919, found 126.0937.

(3R,5R)-1-azabicyclo[3.2.1]octan-3-amine dihydrochloride:

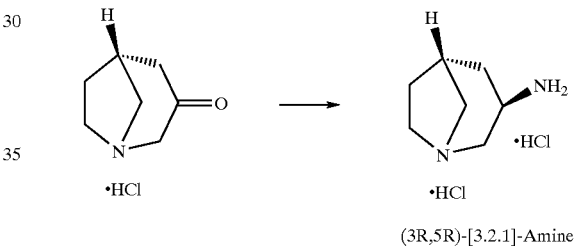

(3R,5R)-[3.2.1]-Amine

To a flask containing (5R)-1-azabicyclo[3.2.1]octan-3-one hydrochloride (3.64 g, 22.6 mmol), hydroxylamine hydrochloride (2.04 g, 29.4 mmol), and ethanol (130 mL) is added sodium acetate trihydrate (9.23 g, 67.8 mmol). The mixture stirred for 3 h and is filtered and concentrated. The resulting white solid is taken up in n-propanol (100 mL) and sodium (~13.6 g, 618 mmol) is added in 20–25 portions. The reaction spontaneously begins to reflux, and the reaction is heated in an oil bath (100° C.). The addition is complete in ~20 min and the mixture solidifies after ~40 min. The oil bath is removed and n-propanol (2×25 mL) is added dissolving the remaining sodium metal. The mixture is carefully quenched through the dropwise addition of H$_2$O (100 mL). Saturated aq. NaCl (20 mL) is added, and the layers are separated. The organic layer is dried (MgSO$_4$), filtered, treated with freshly prepared MeOH/HCl, and concentrated. The resulting solid is triturated with 30 mL EtOH, filtered and dried in vaccuo to afford 3.51 g as a white solid: $[\alpha]^{25}_D$=−3 (c 0.94, DMSO); $^1$H NMR (400 MHz, DMSO-d$_6$) δ 3.60–3.80, 2.95–3.10, 2.65–2.75, 1.90–2.15, 1.70–1.90; HRMS (FAB) calcd for C$_7$H$_{14}$N$_2$ (M+H$^+$) 127.1235, found 127.1235.

Preparation of the 3.2.2 Amines

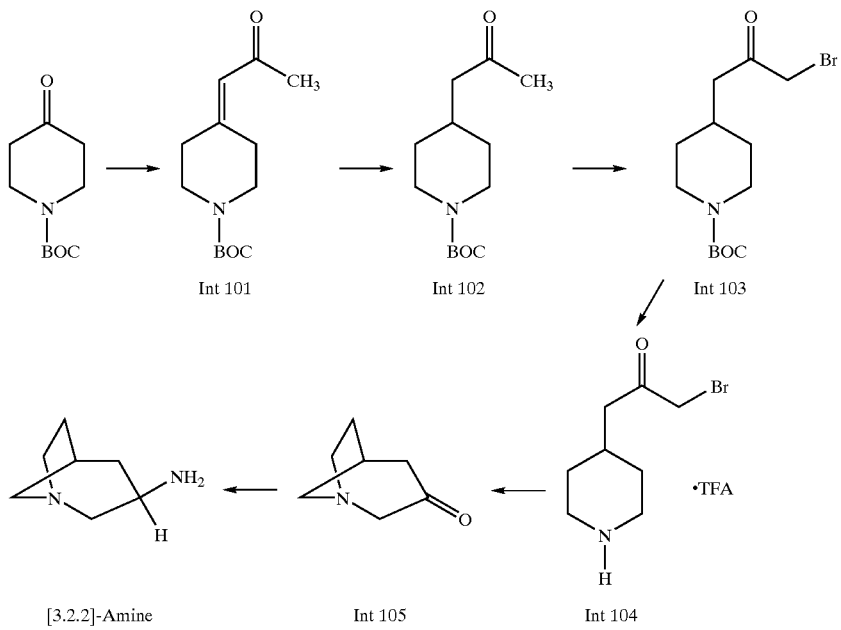

Preparation of tert-butyl 4-(2-oxopropylidene)piperidine-1-carboxylate (Int 101):

Sodium hydride (60% oil dispersion, 2.01 g, 50.2 mmol) was washed with pentane (3×) and suspended in dry THF (40 mL). The solution was cooled to 0° C. before diethyl (2-oxopropyl)phosphonate (9.75 g, 50.2 mmol) was added dropwise. After complete addition, the solution was warmed to rt and stirred for 30 min. tert-Butyl 4-oxo-1-piperidinecarboxylate (5.0 g, 25.1 mmol) was added in portions over 10 min, followed by stirring at rt for 2 h. A saturated aqueous solution of ammonium chloride was added, followed by dilution with ether. The organic layer was extracted with water. The organic layer is dried over anhydrous $MgSO_4$, filtered and concentrated to a yellow oil. The crude product was purified by flash chromatography on silica gel. Elution with hexanes-ether (60:40) gave 4.5 g (75%) of Int 101 as a white solid: $^1$H NMR ($CDCl_3$) δ 6.2, 3.5, 3.4, 2.9, 2.3, 2.2, 1.5.

Preparation of tert-butyl 4-(2-oxopropyl)piperidine-1-carboxylate (Int 102):

A mixture of Int 101 (4.5 g, 19 mmol) and 10% palladium on activated carbon (450 mg) in EtOH (150 mL) was placed in a Parr bottle and hydrogenated for 5 h at 50 psi. The mixture was filtered through Celite, and the filtrate was concentrated in vacuo to afford 4.3 g (94%) of Int 102 as a clear oil: $^1$H NMR ($CDCl_3$) δ 4.1, 2.8, 2.4, 2.2, 2.0, 1.7, 1.5, 1.1.

Preparation of tert-butyl 4-(3-bromo-2-oxopropyl) piperidine-1-carboxylate (Int 103):

To a stirred solution lithium hexamethyldisilylamide in THF (20.0 mL, 1.0 M) in a −78° C. bath was added chlorotrimethylsilane (11.0 mL, 86.4 mmol) dropwise. The mixture was stirred at −78° C. for 20 min, followed by addition of 102 (3.21 g, 13.3 mmol) in a solution of THF (50 mL) dropwise. After complete addition, the mixture was stirred at −78° C. for 30 min. The mixture was warmed to 0° C. in an ice-water bath and phenyltrimethylammonium tribromide (5.25 g, 14.0 mmol) was added. The mixture was stirred in an ice-bath for 30 min, followed by the addition of water and ether. The aqueous layer was washed with ether, and the combined organic layers were washed with saturated aqueous sodium thiosulfate solution. The organic layer was dried over anhydrous $MgSO_4$, filtered and concentrated in vacuo to afford a yellow oil. The crude product was purified by flash chromatography on silica gel. Elution with hexanes-ether (60:40) gave 2.2 g (52%) of Int 103 as a lt. yellow oil: $^1$H NMR ($CDCl_3$) δ 4.2–4.1, 3.9, 2.8, 2.7, 2.6, 2.1–2.0, 1.7, 1.5, 1.2–1.1.2.

Preparation of 1-bromo-3-piperidin-4-ylacetone trifluoroacetate (Int 104):

To a stirred solution of 103 (2.2 g, 6.9 mmol) in $CH_2Cl_2$ (30 mL) in an ice-water bath was added trifluoroacetic acid (10 mL, 130 mmol). The mixture was stirred at 0° C. for 30 min. The volatiles were removed in vacuo to afford 2.0 g (87%) of Int 104 as a yellow residue: MS (ESI) for $C_8H_{15}BrNO$ [M+H] m/e 220.

Preparation of 1-azabicyclo[3.2.2]nonan-3-one (Int 105):

To a stirred solution of DIEA (13 mL) in acetonitrile (680 mL) at reflux temperature was added a solution of Int 104 (2.0 g, 6.0 mmol) in acetonitrile (125 mL) over a 4 h period via syringe pump. The mixture was kept at reflux temperature overnight. The mixture was concentrated in vacuo and the remaining residue was partitioned between a saturated aqueous $K_2CO_3$ solution and $CHCl_3$—MeOH (90:10). The aqueous layer was extracted with $CHCl_3$—MeOH (90:10), and the combined organic layers were dried over $MgSO_4$, filtered and concentrated in vacuo to a brown oil. The crude product was purified by flash chromatography on silica gel. Elution with $CHCl_3$—MeOH—$NH_4OH$ (95:4.5:0.5) gave 600 mg (72%) of Int 105 as a clear solid: $^1$H NMR ($CDCl_3$) δ 3.7, 3.3–3.2, 3.1–3.0, 2.7, 2.3, 2.0–1.8.

Preparation of 1-azabicyclo[3.2.2]nonan-3-amine bis(4-methylbenzenesulfonate) ([3.2.2]-Amine):

To a stirred mixture of Int 105 (330 mg, 2.4 mmol) and sodium acetate.trihydrate (670 mg, 4.8 mmol) in EtOH (6.0 mL) was added hydroxylamine.hydrochloride (200 mg, 2.8 mmol). The mixture was stirred at rt for 10 h. The mixture was filtered and the filtrate was concentrated in vacuo to a yellow solid. To a solution of the solid (350 mg, 2.3 mmol)

in n-propanol (30 mL) at reflux temperature was added sodium metal (2.0 g, 87 mmol) in small portions over 30 min. Heating at reflux was continued for 2 h. The solution is cooled to rt and brine is added. The mixture is extracted with n-propanol, and the combined organic layers are concentrated in vacuo. The residue was taken up in CHCl$_3$ and the remaining solids were filtered. The filtrate was dried over anhydrous MgSO$_4$, filtered and concentrated in vacuo to a clear solid. To a stirred solution of the solid (320 mg, 2.3 mmol) in EtOH (4 mL) was added p-toluenesulfonic acid monohydrate (875 mg, 4.6 mmol). The solution was warmed in a water bath to 45° C. for 30 min, followed by concentration of the solvent to afford 710 mg (62%) of [3.2.2]-Amine as a white solid:

$^1$H NMR (CD$_3$OD) δ 7.7, 7.3, 4.1–3.9, 3.6–3.4, 2.6–2.5, 2.4, 2.2–2.1, 2.1–2.0, 1.9.

Resolution of Stereoisomers:

The amine can be coupled to form the appropriate amides or thioamides as a racemic mixture. The racemic mixture can then be resolved by chromatography using chiral columns or chiral HPLC, techniques widely known in the art, to provide the requisite resolved enantiomers 3(R) and 3(S) of said amides or thioamides.

Preparation of Acids and Coupling to Appropriate Amine

The following examples are provided as examples and are not intended to limit the scope of this invention to only those provided examples and named compounds. Also, the salts made in the examples are only exemplary and are not intended to limit the invention. Any pharmaceutically acceptable salt can be made by one of ordinary skill in the art. Further, the naming of specific stereoisomers is for exemplification, and is not intended to limit in anyway the scope of the invention. The invention includes the following examples in pure stereoisomeric form or as racemic mixtures.

EXAMPLE 1

N-(exo-4(S)-1-azabicyclo[2.2.1]hept-3-yl)-1,3-benzoxazole-5-carboxamide.fumarate

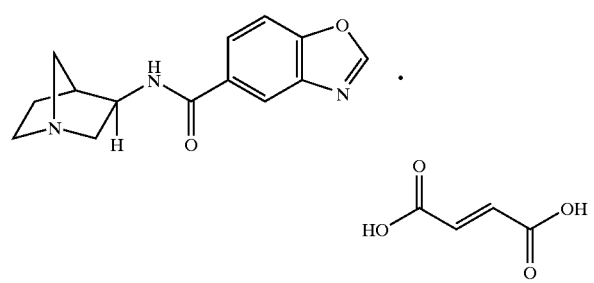

A mixture of 4-amino-3-hydroxybenzoic acid (1.0 g, 6.5 mmol) and trimethyl orthoformate (2.0 mL, 18.3 mmol) is heated in an oil bath at 100° C. for 30 h. The mixture is cooled to rt and diluted with MeOH. The resulting solution is filtered through a pad of Celite, and the filtrate is concentrated in vacuo to give 1,3-benzoxazole-5-carboxylic acid as a brown solid (290 mg, 27%): $^1$H NMR (DMSO-d$_6$) δ 13.0, 8.9, 8.3, 8.1, 7.9.

Coupling:

To a stirred solution of 1,3-benzoxazole-5-carboxylic acid (290 mg, 1.78 mmol) in dry DMF (15 mL) is added DIEA (928 μL, 5.34 mmol), followed by exo-4(S)-[2.2.1]-Amine (740 mg, 1.62 mmol). The solution is cooled with an ice bath before 676 mg (1.78 mmol) of HATU is added. The solution is allowed to warm to rt and stir for 16 h. The solvent is removed in vacuo, and the remaining residue is partitioned between saturated aqueous K$_2$CO$_3$ solution and 9:1 chloroform-methanol. The aqueous layer is extracted with 9:1 chloroform-methanol, and the combined organic layers are washed with brine, dried over MgSO$_4$, filtered and concentrated in vacuo to afford the desired material as a yellow solid (401 mg, 96%): low-resolution MS (ESI) m/e 258 [M+H].

Salt Formation:

To a stirred solution of the above amide (231 mg, 0.90 mmol) in acetone (5 mL) is added a hot solution of fumaric acid (100 mg, 0.90 mmol) in IPA (2 mL). The mixture is stirred for 30 min at 50° C. The solvents are removed in vacuo, acetone (5 mL) is added. The mixture is stirred overnight at rt. The solid is collected by filtration and washed with acetone. The solid is dried under high vacuum overnight to give 160 mg (50%) of the title compound as an off-white solid: HRMS (FAB) calculated for C$_{14}$H$_{16}$N$_3$O$_2$ [M+H] m/e 258.1242, found 258.1239.

EXAMPLE 2

N-(1-azabicyclo[2.2.1]hept-3-yl)-2-methyl-1,3-benzoxazole-5-carboxamide

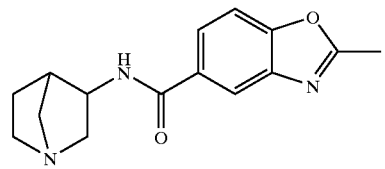

A mixture of 4-amino-3-hydroxybenzoic acid (480 mg, 3.1 mmol) and trimethyl orthoacetate (1.0 mL, 7.9 mmol) are heated in an oil bath to 107° C. for 2 h. The mixture is cooled to rt and diluted with MeOH. The resulting solution is filtered through a pad of silica gel and the filtrate is concentrated in vacuo to give 2-methyl-1,3-benzoxazole-5-carboxylic acid as an orange solid (490 mg, 88%): $^1$H NMR (DMSO-d$_6$) δ 13.0, 8.2, 8.0, 7.8, 2.7.

Coupling:

2-Methyl-1,3-benzoxazole-5-carboxylic acid can be coupled with the exo- or endo-[2.2.1]-Amine using procedures discussed herein to obtain Example 2(i).

EXAMPLE 3

N-(1-azabicyclo[2.2.1]hept-3-yl)-1,3-benzoxazole-6-carboxamide

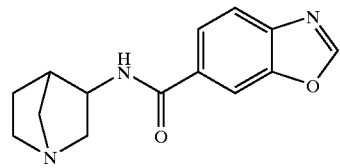

A mixture of 4-amino-3-hydroxybenzoic acid (250 mg, 1.63 mmol) and trimethyl orthoformate (500 μL, 4.57 mmol) are heated in an oil bath at 100° C. for 2 h. The mixture is cooled to rt and diluted with MeOH. The resulting solution is filtered through a pad of Celite, and the filtrate is concentrated in vacuo to give 1,3-benzoxazole-6-carboxylic acid as a brown solid (237 mg, 89%): $^1$H NMR (DMSO-d$_6$) δ 13.2, 8.9, 8.3, 8.0, 7.9.

Coupling:

1,3-Benzoxazole-6-carboxylic acid can be coupled with the exo- or endo-[2.2.1]-Amine using procedures discussed herein to obtain Example 3(i).

EXAMPLE 4

N-(1-azabicyclo[2.2.1]hept-3-yl)-2-methyl-1,3-benzoxazole-6-carboxamide

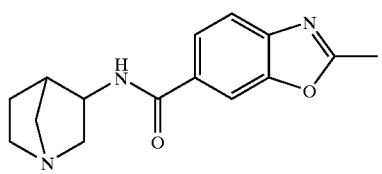

A mixture of 4-amino-3-hydroxybenzoic acid (500 mg, 3.7 mmol) and trimethyl orthoacetate (1.0 mL, 7.9 mmol) is heated in an oil bath to 100° C. for 2 h. The mixture is cooled to rt and diluted with MeOH. The resulting solution is filtered through a pad of Celite, and the filtrate is concentrated in vacuo to give 2-methyl-1,3-benzoxazole-6-carboxylic acid as an off-white solid (266 mg, 46%): $^1$H NMR (DMSO-d$_6$) δ 13.1, 8.2, 8.0, 7.7, 2.7.

Coupling:

2-Methyl-1,3-benzoxazole-6-carboxylic acid can be coupled with the exo- or endo-[2.2.1]-Amine using procedures discussed herein to give Example 4(i).

EXAMPLE 5

N-(exo-4(S)-1-azabicyclo[2.2.1]hept-3-yl)-1,3-benzothiazole-6-carboxamide.fumarate

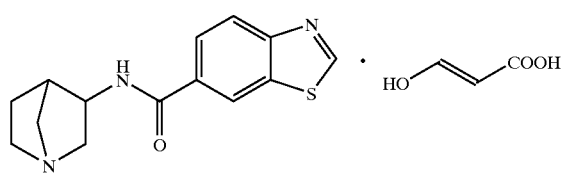

Coupling and Salt Formation:

Using the procedure outlined for Example 1(i), 1,3-benzothiazole-6-carboxylic acid is coupled with the exo-[2.2.1]-Amine and the fumarate salt made to give the title compound in 75% yield. $^1$H NMR (CD$_3$OD) δ 9.4, 8.6, 8.2, 8.1, 6.7, 4.3, 3.8, 3.5–3.4, 3.3–3.2, 3.1, 2.2, 1.9–1.8.

EXAMPLE 6

N-[exo-(4S)-1-azabicyclo[2.2.1]hept-3-yl]-indane-5-carboxamide.fumarate

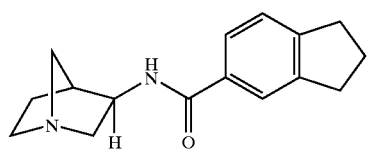

-continued

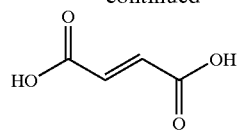

To a stirred 6% aqueous sodium hypochlorite solution in an oil bath to 55° C. is added 1-indane-5-yl-ethanone (1.0 g, 6.2 mmol). The solution is stirred at 55° C. for 2 h, followed by cooling to rt. Solid sodium bisulfite is added until the solution becomes clear. The mixture is diluted with water, followed by aqueous hydrochloric acid (6.0 M). The solid that forms is filtered and washed several times with water. The solid is dried under high vacuum at 60° C. for 5 h to afford 5-indancarboxylic acid as a white solid (0.96 g, 95%): $^1$H NMR (CDCl$_3$) δ 8.0, 7.9, 7.3, 3.0, 2.1.

Coupling:

The free base of Example 6(i) is obtained in 99% using the coupling procedure for Example 1(i), making non-critical changes.

Salt formation: To a stirred solution of the free base (128 mg, 0.5 mmol) in MeOH (5 mL) is added a warm solution of fumaric acid (58 mg, 0.5 mmol) in MeOH (5 mL). The mixture is warmed to 40° C. for 10 min. The solvent is removed in vacuo, and the remaining residue is diluted with acetone (5 mL). The mixture is stirred overnight at rt. The solid precipitate is collected by filtration, washed with acetone, and dried in vacuo overnight to give 113 mg (59%) of Example 6(i) as a white solid: $^1$H NMR (400 MHz, CD$_3$OD) δ 7.72, 7.64, 7.32, 6.71, 4.22–4.19, 3.71–3.66, 3.43–3.36, 3.25–3.19, 3.03, 2.97, 2.20–2.10, 1.86–1.79.

EXAMPLE 7

N-(exo-4(S)-1-azabicyclo[2.2.1]hept-3-yl)-1,3-benzodioxole-5-carboxamide.4-methylbenzenesulfonate

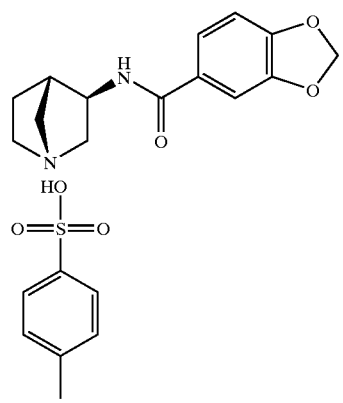

To a stirred solution of piperonylic acid (166 mg, 1.0 mmol) in anhydrous DMF (10 mL) are added DIEA (530 μL, 3.05 mmol) and exo-(4S)-[2.2.1]-3-Amine (456 mg, 1.0 mmol). The mixture is cooled to 0° C. in an ice bath, and HATU (380 mg, 0.5 mmol) is added in one portion. The reaction mixture is allowed to warm to rt and is stirred overnight. The solvent is removed in vacuo, and the residue is partitioned between saturated aqueous K$_2$CO$_3$ solution and chloroform. The aqueous layer is extracted with chloroform (2×). The combined organic layers are washed with brine, dried over Na$_2$SO$_4$, filtered and concentrated in vacuo. The crude product is purified by flash chromatography on silica gel. Elution with CHCl₃—MeOH—NH₄OH (89:9:1) gives 260 mg (99%) of the corresponding amide as a solid.

To a stirred solution of the amide (182 mg, 0.70 mmol) in MeOH (5 mL) is added a solution of p-toluenesulfonic acid monohydrate (133 mg, 0.70 mmol) in MeOH (5 mL). The mixture is stirred for 10 min at 50° C. The solvent is removed in vacuo, and the remaining residue is diluted with acetone (10 mL). The mixture is stirred overnight at rt. The solid precipitate is collected by filtration, washed with acetone, and dried under high vacuum overnight to give 191 mg (63.5%) of title compound as a white solid: ¹H NMR (400 MHz, CD₃OD) δ 7.73–7.12, 7.48–7.45, 7.35, 7.26–7.24, 6.92–6.90, 6.06, 4.22–4.19, 3.75–3.70, 3.48–3.35, 3.30–3.25, 3.05–3.04, 2.39, 2.23–2.14, 1.88–1.81.

EXAMPLE 8

N-[1-azabicyclo[2.2.1]hept-3-yl]-1,3-oxazolo[5,4-c]pyridine-6-carboxamide intervals and then the final 2.3 mL after the reaction stirs for 15 h at 90° C. The reaction is stirred at 90° C. for another 4 h and then cooled by placing the flask in an ice bath. The pH of the reaction is then adjusted to 1 using 6N HCl. The reaction is stirred for 1.5 h in an ice bath allowing an undesired solid to form. The undesired solid is removed by filtration, and the filtrate is extracted seven times with EtOAc. The combined organic extracts are concentrated in vacuo, toluene is added to the flask and removed in vacuo to azeotrope water, and then CH₂Cl₂ is added and removed in vacuo to obtain 2-chloro-6-(hydroxymethyl)-3-pyridinol as a pale yellow solid (81% yield) sufficiently pure for subsequent reaction. MS (EI) for C₆H₆ClNO₂, m/z: 159(M)⁺.

2-Chloro-6-(hydroxymethyl)-3-pyridinol (11.6 g, 72.7 mmol) and NaHCO₃ (18.3 g, 218 mmol) are added to 200 mL water. The mixture is stirred until homogeneous, the flask is placed in an ice bath, iodine (19.4 g, 76.3 mmol) is added, and the reaction is stirred over the weekend at rt. The pH of the mixture is adjusted to 3 with 2N NaHSO₄, and the mixture is extracted with 4×50 mL EtOAc. The combined organic layer is dried over anhydrous MgSO₄, is filtered, and the filtrate is concentrated in vacuo to a yellow solid. The

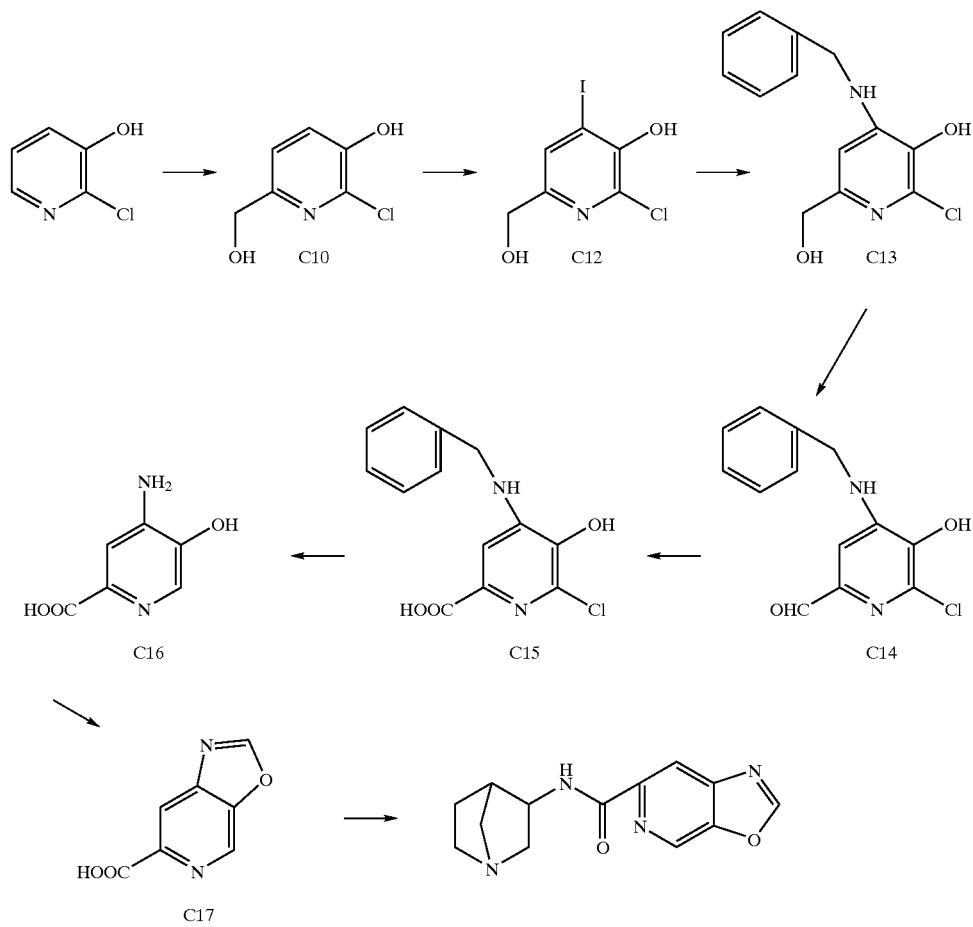

Preparation of the Acid:

2-Chloro-3-pyridinol (20.0 g, 0.154 mole), NaHCO₃ (19.5 g, 0.232 mole, 1.5 equ), and 150 mL of water are placed in a flask. The flask is placed in an oil bath at 90° C., and after 5 min, 37% aqueous formaldehyde (40.5 mL, 0.541 mole, 3.5 equ) is added in six unequal doses in the following order: 12 mL, 3×8 mL, then 2.2 mL all at 90-min crude solid is washed with EtOAc to provide 2-chloro-6-(hydroxymethyl)-4-iodo-3-pyridinol as an off-white solid (62% yield), and the filtrate is concentrated to a small volume and is chromatographed over 250 g silica gel (230–400 mesh) eluting with 2.5:4.5:4:0.1 EtOAc/CH₂Cl₂/hexane/acetic acid. The desiredd fractionawere combined and concentrated to afford additional pure (12% yield). MS (EI) for C$_6$H$_5$ClINO$_2$, m/z: 285(M)$^+$.

4-(Benzylamino-2-chloro-6-(hydroxymethyl)-3-pyridinol (C13) maybe produced by amination of 2-chloro-6-(hydroxymethyl)-4-iodo-3-pyridinol (C12) with benzylamine under palladium catalysis. Amination of aryl iodides with primary amines such as benzylamine under palladium catalysis is generally described in a review by B. H. Yang and S. L. Buchwald in *J. Organomet. Chem.*, 576, 125–146, 1999 and in greater detail in the references therein.

4-(Benzylamino-2-chloro-6-(hydroxymethyl)-3-pyridinol may be oxidized to 4-(benzylamino-2-chloro-3-hydroxypyridine-6-carboxaldehyde (C14) under a wide variety of conditions (e.g., TPAP and NMO in CH$_2$Cl$_2$). 4-(Benzylamino-2-chloro-3-hydroxypyridine-6-carboxaldehyde may be oxidized to produce the corresponding carboxylic acid C15 using an oxidizing reagent such as NaClO$_2$ and KH$_2$PO$_4$ in DMSO/H$_2$O or Ag$_2$O, or hydrogen peroxide or ruthenium tetroxide.

Removal of the benzyl group and the chloro group of Acid C15 may be accomplished by utilizing hydrogen or a hydrogen source (e.g., cyclohexene, cyclohexadiene, ammonium formate, hydrazine, etc.) in the presence of Pd/C or other catalyst, under a variety of conditions and in various solvents, to produce 4-amino-5-hydroxypyridine-2-carboxylic acid (Acid C16).

Cyclocondensation of Acid C16 with trimethyl orthoformate in the presence of catalytic para-toluenesulfonic acid may be conducted to produce [1,3]-oxazolo[5,4-c]pyridine-6-carboxylic acid (Acid C17).

[1,3]-Oxazolo[5,4-c]pyridine-6-carboxylic acid can be coupled with the exo- or endo-[2.2.1]-Amine using procedures discussed herein to give Example 8(i).

EXAMPLE 9

N-[1-azabicyclo[2.2.1]hept-3-yl]-2-benzoisothiophene-5-benzamide

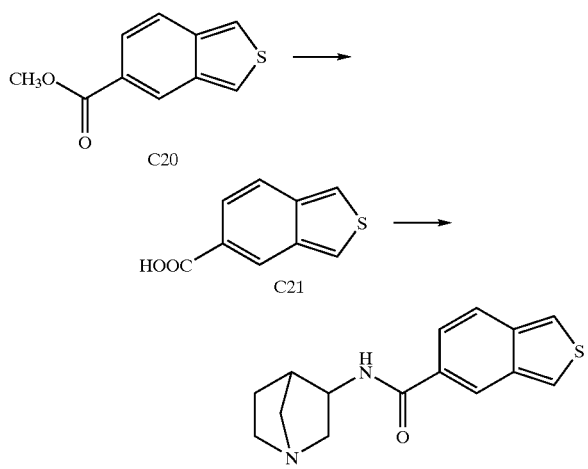

Acid C21 can be made by the saponification of the methyl ester C20, which can be made pursuant to Wynberg, Hans, et al., *Recl. Trav. Chim. Pays-Bas* (1968), 87(10), 1006–1010. Acid C21 can then be coupled with the exo- or endo-[2.2.1]-Amine using methods discussed herein to provide Example 9 as the free base that can be made into a suitable salt.

EXAMPLE 10

N-[exo-(4S)-1-azabicyclo[2.2.1]hept-3-yl]-1H-indazole-5-carboxamide.fumarate

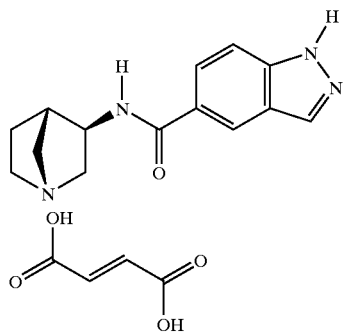

To a stirred mixture of methyl 3-methyl-4-aminobenzoate (5.0 g, 30.0 mmol) and potassium acetate (2.94 g, 30.0 mmol) in chloroform (50 mL) is added acetic anhydride (5.66 mL, 60.0 mmol). The mixture is stirred for 30 min at rt, followed by the addition of 18-crown-6 (1.58 g, 6.0 mmol) and n-amyl nitrite (7.78 g, 66.0 mmol). The mixture is heated to reflux for 16 h, followed by cooling to rt. The mixture is washed sequentially with aqueous sodium bicarbonate solution (2×), water and brine. The organic layer is dried over MgSO$_4$, filtered and concentrated in vacuo. The crude product is purified by flash chromatography on silica gel. Elution with hexanes-EtOAc (80:20) gives 3.1 g (47%) of methyl 1-acetyl-1H-indazole-5-carboxylate as a yellow solid: $^1$H NMR (400 MHz, CDCl$_3$) δ 8.52–8.50, 8.3, 8.2, 4.0, 2.8.

To a stirred solution of methyl 1-acetyl-1H-indazole-5-carboxylate (1.16 g, 5.31 mmol) in methanol (10 mL) is added HCl (10 mL of a 6.0 M aqueous solution). The mixture is stirred at rt overnight. The methanol is removed in vacuo, and the remaining aqueous solution is basified with 30% aqueous NH$_4$OH to pH=8. The resulting precipitate is collected by filtration, washed with water and dried in vacuo to afford 900 mg (96%) of methyl 1H-indazole-5-carboxylate as a light yellow solid: $^1$H NMR (400 MHz, DMSO-d$_6$) δ 13.4, 8.5, 8.3, 7.9, 7.6, 3.9.

To a stirred solution of methyl 1H-indazole-5-carboxylate (500 mg, 2.84 mmol) in MeOH (15 mL) is added sodium hydroxide (20 mL of 2.5% aqueous solution). The mixture is heated at reflux for 1 h, followed by removal of the methanol in vacuo. The remaining aqueous solution is washed with EtOAc (5 mL), acidified with 1 N aqueous HCl to pH~5–6. The resulting precipitate is collected by filtration, washed with water and dried in vacuo to afford 410 mg (89%) of 1H-indazole-5-carboxylic acid as a tan solid: IR (diffuse reflectance) 3290, 3115, 2964, 2954, 2813, 2606, 2557, 2505, 1687, 1627, 1321, 1274, 948, 937, 769 cm$^{-1}$; $^1$H NMR (400 MHz, DMSO-d$_6$) δ 13.4 12.7, 8.5 8.2, 7.9, 7.6.

To a stirred solution 1H-indazole-5-caboxylic acid (162 mg, 1.00 mmol) in anhydrous DMF (10 mL) are added DIEA (531 µL, 3.05 mmol) and exo-(4S)-[2.2.1]-3-amine (456 mg, 1.00 mmol). The mixture is cooled to 0° C., and HATU (380 mg, 1.00 mmol) is added in one portion. The reaction mixture is allowed to warm to rt and stirred overnight. The solvent is removed in vacuo, and the residue is partitioned between saturated aqueous K$_2$CO$_3$ solution and chloroform. The aqueous layer is extracted with chloroform (4×). The combined organic layers are washed with brine, dried over Na$_2$SO$_4$, filtered and concentrated in vacuo. The crude product is purified by flash chromatography on silica gel. Elution with CHCl$_3$—MeOH—NH$_4$OH (89:9:1) gives 70 mg (27%) of the amide as a white solid.

To a stirred solution of the amide (70 g, 0.27 mmol) in MeOH (5 mL) is added a warm solution of fumaric acid (32 mg, 0.27 mmol) in MeOH (5 mL). The mixture is stirred for 10 min at 40° C. The solvent is removed in vacuo, and the remaining residue is diluted with acetone (5 mL). The mixture is stirred overnight at rt. The solid precipitate is collected by filtration, washed with acetone, and dried under high vacuum overnight to give 82 mg (81%) of Example 10(i) as a white solid: $^1$H NMR (400 MHz, CD$_3$OD) δ 8.43, 8.35, 8.21, 7.87–7.84, 7.58–7.56, 6.53, 3.81, 3.15, 2.80, 2.70–2.60, 1.75, 1.35.

EXAMPLE 11

N-[exo-(4S)-1-azabicyclo[2.2.1]hept-3-yl]-1H-indazole-6-carboxamide.fumarate.H$_2$O

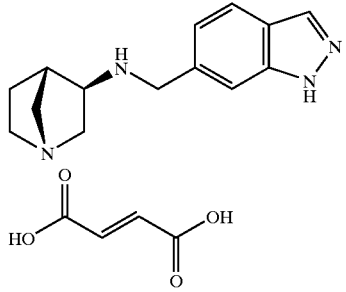

To a stirred solution of aqueous HCl (15 mL of concentrated HCl and 50 mL of water) is added 3-amino-4-methyl benzoic acid (5.0 g, 33 mmol). The mixture is cooled in an acetone-ice water bath, followed by the slow addition of a solution of sodium nitrite (2.28 g, 33 mmol) in water (12 mL). The mixture is allowed to stir for 10 min at which point the mixture becomes homogeneous. A saturated aqueous solution of sodium acetate is added until pH~6. 2-Methylpropane-2-thiol (1.8 mL, 16 mmol) is added and the mixture is stirred for 1 h. The resulting precipitate is collected by filtration, washed with water and dried in vacuo to give 3.85 g (96%) of 3-(tert-butylthio)diazenyl-4-methylbenzoic acid as a tan solid: $^1$H NMR (400 MHz, DMSO-d$_6$) δ 13.2, 7.8, 7.5, 7.3, 2.1, 1.6.

To a stirred solution of potassium tert-butoxide (8.14 g, 72.7 mmol) in DMSO (30 mL) is added a solution of 3-(tert-butylthio)diazenyl-4-methylbenzoic acid (1.85 g, 7.34 mmol) in DMSO (20 mL). The mixture is stirred overnight at rt. The mixture is diluted with ice-water, acidified with 1N aqueous HCl to a pH of about 5 to about 6 and extracted with EtOAc (3×). The combined organic layers are washed sequentially with water and brine, dried over MgSO$_4$ and concentrated in vacuo to afford 1.17 g (98%) of 1H-indazole-6-carboxylic acid as a tan solid: IR (diffuse reflectance) 3171, 3135, 3067, 3014, 2950, 2889, 2865, 1685, 1326, 1308, 1240, 960, 945, 762, 740 cm$^{-1}$; $^1$H NMR (400 MHz, DMSO-d$_6$) δ 13.4, 13.0, 8.2, 8.2, 7.9, 7.7.

Example 11(i) is obtained in 81% yield by coupling 1H-indazole-6-carboxylic acid with exo-(4S)-[2.2.1]-3-amine using conditions according to Example 10(i), making non-critical changes. The salt is then formed to obtain Example 11(i) in 77% yield from the coupling to salt: $^1$H NMR (400 MHz, CD$_3$OD) δ 8.15, 8.10, 7.88, 7.63, 6.71, 4.27–4.25, 3.74–3.69, 3.46–3.36, 3.23–3.21, 3.08, 2.24–2.14, 1.88–1.81.

EXAMPLE 12

N-[(exo-4S)-1-azabicyclo[2.2.1]hept-3-yl]-1,3-dioxolo[4,5-c]pyridine-6-carboxamide

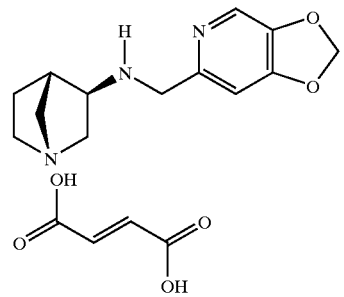

To a stirred solution of ethyl [1,3]dioxolo[4,5-c]pyridine-6-carboxylate (see: Dallacker, F. Z. Naturforsch. 1979, 34b, 1729–1736.) (462 mg, 2.37 mmol) in EtOH (5 mL) is added NaOH (10 mL of a 5% aqueous solution). The mixture is heated to reflux for 1.5 h, followed by cooling to rt. The ethanol is removed in vacuo, and the remaining aqueous layer is acidified to pH=4 with 1N HCl, extracted with CH$_2$Cl$_2$ continuously for 2 days. The organic layer is concentrated to a white solid (315 mg, 80%): $^1$H NMR (400 MHz, DMSO-d$_6$) δ 8.12, 7.52, 6.21.

To a stirred solution of [1,3]dioxolo[4,5-c]pyridine-6-carboxylic acid (100 mg, 0.60 mmol) in anhydrous DMF (10 mL) in an ice bath is added sequentially DIEA (318 µL, 1.83 mmol), (3R, 4S)-1-azabicyclo[2.2.1]heptan-3-amine bis(hydro-para-toluenesulfonate) (273 mg, 0.60 mmol) and HATU (228 mg, 0.60 mmol). The mixture is stirred at 0° C. for 30 min, followed by warming to rt and stirring overnight. The mixture is concentrated in vacuo to a yellow residue. The residue is partitioned between CHCl$_3$—MeOH (90:10) and half saturated aqueous potassium carbonate solution. The aqueous layer is extracted with CHCl$_3$—MeOH (90:10), and the combined organic layers are washed with brine, dried(MgSO$_4$), filtered and concentrated in vacuo. The crude product is purified by flash chromatography on silica gel. Elution with CHCl$_3$—MeOH—NH$_4$OH (90:9:1) gives 150 mg (96%) of a white solid.

To a stirred solution of the amide (150 mg, 0.58 mmol) in MeOH (5 mL) is added fumaric acid (66 mg, 0.58 mmol). The mixture is warmed on a water bath to 40° C. for 30 min, followed by removal of the solvent in vactio. Acetone (10 mL) and water (0.1 mL) are added to the residue, which produced a white precipitate. The solid precipitate is filtered, washed with acetone and dried in vacuo to afford 209 mg (92%) of Example 12(i) as a white solid: $^1$H NMR (400 MHz, DMSO-d$_6$) δ 8.61, 8.18, 7.55, 6.54, 6.25, 3.76, 3.06, 2.89–2.79, 2.63–2.58, 2.46, 1.68, 1.30.

The following examples can be prepared according to the coupling procedures discussed herein using the azabicyclic amines and acids discussed herein:

EXAMPLE 21
N-(1-(6-methyl)-azabicyclo[2.2.1]hept-3-yl)-1,3-benzoxazole-5-carboxamide

EXAMPLE 22
N-(1-(6-methyl)-azabicyclo[2.2.1]hept-3-yl)-2-methyl-1,3-benzoxazole-5-carboxamide

EXAMPLE 23
N-(1-(6-methyl)-azabicyclo[2.2.1]hept-3-yl)-1,3-benzoxazole-6-carboxamide

EXAMPLE 24
N-(1-(6-methyl)-azabicyclo[2.2.1]hept-3-yl)-2-methyl-1,3-benzoxazole-6-carboxamide

EXAMPLE 25
N-(1-(6-methyl)-azabicyclo[2.2.1]hept-3-yl)-1,3-benzothiazole-6-carboxamide

EXAMPLE 26
N-(1-(6-methyl)-azabicyclo[2.2.1]hept-3-yl)indane-5-carboxamide

EXAMPLE 27
N-(1-(6-methyl)-azabicyclo[2.2.1]hept-3-yl)-1,3-benzodioxole-5-carboxamide

EXAMPLE 28
N-(1-(6-methyl)-azabicyclo[2.2.1]hept-3-yl)-1,3-oxazolo[5,4-c]pyridine-6-carboxamide

EXAMPLE 29
N-(1-(6-methyl)-azabicyclo[2.2.1]hept-3-yl)-2-benzoisothiophene-5-benzamide

EXAMPLE 30
N-(1-(6-methyl)-azabicyclo[2.2.1]hept-3-yl)-1H-indazole-5-carboxamide

EXAMPLE 31
N-(1-(6-methyl)-azabicyclo[2.2.1]hept-3-yl)-1H-indazole-6-carboxamide

EXAMPLE 32
N-(1-(6-methyl)-azabicyclo[2.2.1]hept-3-yl)-1,3-dioxolo[4,5-c]pyridine-6-carboxamide

EXAMPLE 41
N-(1-(6-methyl)-azabicyclo[2.2.2]oct-3-yl)-1,3-benzoxazole-5-carboxamide

EXAMPLE 42
N-(1-(6-methyl)-azabicyclo[2.2.2]oct-3-yl)-2-methyl-1,3-benzoxazole-5-carboxamide

EXAMPLE 43
N-(1-(6-methyl)-azabicyclo[2.2.2]oct-3-yl)-1,3-benzoxazole-6-carboxamide

EXAMPLE 44
N-(1-(6-methyl)-azabicyclo[2.2.2]oct-3-yl)-2-methyl-1,3-benzoxazole-6-carboxamide

EXAMPLE 45
N-(1-(6-methyl)-azabicyclo[2.2.2]oct-3-yl)-1,3-benzothiazole-6-carboxamide

EXAMPLE 46
N-(1-(6-methyl)-azabicyclo[2.2.2]oct-3-yl)indane-5-carboxamide

EXAMPLE 47
N-(1-(6-methyl)-azabicyclo[2.2.2]oct-3-yl)-1,3-benzodioxole-5-carboxamide

EXAMPLE 48
N-(1-(6-methyl)-azabicyclo[2.2.2]oct-3-yl)-1,3-oxazolo[5,4-c]pyridine-6-carboxamide

EXAMPLE 49
N-(1-(6-methyl)-azabicyclo[2.2.2]oct-3-yl)-2-benzoisothiophene-5-benzamide

EXAMPLE 50
N-(1-(6-methyl)-azabicyclo[2.2.2]oct-3-yl)-1H-indazole-5-carboxamide

EXAMPLE 51
N-(1-(6-methyl)-azabicyclo[2.2.2]oct-3-yl)-1H-indazole-6-carboxamide

EXAMPLE 52
N-(1-(6-methyl)-azabicyclo[2.2.2]oct-3-yl)-1,3-dioxolo[4,5-c]pyridine-6-carboxamide

EXAMPLE 61
N-(2-azabicyclo[2.2.1]hept-5-yl)-1,3-benzoxazole-5-carboxamide

EXAMPLE 62
N-(2-azabicyclo[2.2.1]hept-5-yl)-2-methyl-1,3-benzoxazole-5-carboxamide

EXAMPLE 63
N-(2-azabicyclo[2.2.1]hept-5-yl)-1,3-benzoxazole-6-carboxamide

EXAMPLE 64
N-(2-azabicyclo[2.2.1]hept-5-yl)-2-methyl-1,3-benzoxazole-6-carboxamide

EXAMPLE 65
N-(2-azabicyclo[2.2.1]hept-5-yl)-1,3-benzothiazole-6-carboxamide

EXAMPLE 66
N-(2-azabicyclo[2.2.1]hept-5-yl)indane-5-carboxamide

EXAMPLE 67
N-(2-azabicyclo[2.2.1]hept-5-yl)-1,3-benzodioxole-5-carboxamide

EXAMPLE 68
N-(2-azabicyclo[2.2.1]hept-5-yl)-1,3-oxazolo[5,4-c]pyridine-6-carboxamide

EXAMPLE 69
N-(2-azabicyclo[2.2.1]hept-5-yl)-2-benzoisothiophene-5-benzamide

EXAMPLE 70
N-(2-azabicyclo[2.2.1]hept-5-yl)-1H-indazole-5-carboxamide

EXAMPLE 71
N-(2-azabicyclo[2.2.1]hept-5-yl)-1H-indazole-6-carboxamide

EXAMPLE 72
N-(2-azabicyclo[2.2.1]hept-5-yl)-1,3-dioxolo[4,5-c]pyridine-6-carboxamide

EXAMPLE 81
N-(2-azabicyclo[2.2.1]hept-6-yl))-1,3-benzoxazole-5-carboxamide

EXAMPLE 82
N-(2-azabicyclo[2.2.1]hept-6-yl))-2-methyl-1,3-benzoxazole-5-carboxamide

EXAMPLE 83
N-(2-azabicyclo[2.2.1]hept-6-yl))-1,3-benzoxazole-6-carboxamide

EXAMPLE 84
N-(2-azabicyclo[2.2.1]hept-6-yl))-2-methyl-1,3-benzoxazole-6-carboxamide

EXAMPLE 85
N-(2-azabicyclo[2.2.1]hept-6-yl))-1,3-benzothiazole-6-carboxamide

EXAMPLE 86
N-(2-azabicyclo[2.2.1]hept-6-yl))indane-5-carboxamide

EXAMPLE 87

N-(2-azabicyclo[2.2.1]hept-6-yl))-1,3-benzodioxole-5-carboxamide

EXAMPLE 88

N-(2-azabicyclo[2.2.1]hept-6-yl))-1,3-oxazolo[5,4-c]pyridine-6-carboxamide

EXAMPLE 89

N-(2-azabicyclo[2.2.1]hept-6-yl))-2-benzoisothiophene-5-benzamide

EXAMPLE 90

N-(2-azabicyclo[2.2.1]hept-6-yl))-1H-indazole-5-carboxamide

EXAMPLE 91

N-(2-azabicyclo[2.2.1]hept-6-yl))-1H-indazole-6-carboxamide

EXAMPLE 92

N-(2-azabicyclo[2.2.1]hept-6-yl))-1,3-dioxolo[4,5-c]pyridine-6-carboxamide

EXAMPLE 101

N-[(3R,5R)-1-azabicyclo[3.2.1]oct-3-yl]-1,3-benzoxazole-5-carboxamide

EXAMPLE 102

N-[(3R,5R)-1-azabicyclo[3.2.1]oct-3-yl]-2-methyl-1,3-benzoxazole-5-carboxamide

EXAMPLE 103

N-[(3R,5R)-1-azabicyclo[3.2.1]oct-3-yl]-1,3-benzoxazole-6-carboxamide

EXAMPLE 104

N-[(3R,5R)-1-azabicyclo[3.2.1]oct-3-yl]-2-methyl-1,3-benzoxazole-6-carboxamide

EXAMPLE 105

N-[(3R,5R)-1-azabicyclo[3.2.1]oct-3-yl]-1,3-benzothiazole-6-carboxamide.fumarate

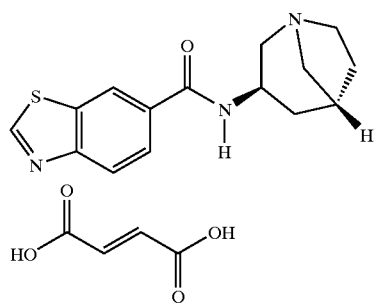

A mixture of benzothiazole-6-carboxylic acid (0.182 g, 1.02 mmol), exo-(3R,5R)-[3.2.1]-Amine (0.209 g, 1.05 mmol), THF (18 mL), DMF (4 mL) and DIEA (0.57 mL, 3.3 mmol) is cooled in an ice bath under $N_2$. HATU (0.388 g, 1.02 mmol) is then added and the mixture stirred at rt overnight. The mixture is then concentrated and the crude product is purified by chromatography (Biotage 40S, (1-9-90) $NH_4OH$—MeOH—$CHCl_3$). The product fractions are pooled and concentrated. The residue is treated with EtOH and fumaric acid (0.95 eq) and evaporated. The residue is treated with EtOAc and the solid collected washed with $Et_2O$ and dried in vaccuo to afford 0.332 g (81%) of the title compound. MS (EI) m/z 287 ($M^+$).

EXAMPLE 106

N-[(3R,5R)-1-azabicyclo[3.2.1]oct-3-yl]indane-5-carboxamide

EXAMPLE 107

N-[(3R,5R)-1-azabicyclo[3.2.1]oct-3-yl]-1,3-benzodioxole-5-carboxamide

EXAMPLE 108

N-[(3R,5R)-1-azabicyclo[3.2.1]oct-3-yl]-1,3-oxazolo[5,4-c]pyridine-6-carboxamide

EXAMPLE 109

N-[(3R,5R)-1-azabicyclo[3.2.1]oct-3-yl]-2-benzoisothiophene-5-benzamide

EXAMPLE 110

N-[(3R,5R)-1-azabicyclo[3.2.1]oct-3-yl]-1H-indazole-5-carboxamide

EXAMPLE 111

N-[(3R,5R)-1-azabicyclo[3.2.1]oct-3-yl]-1H-indazole-6-carboxamide

EXAMPLE 112

N-[(3R,5R)-1-azabicyclo[3.2.1]oct-3-yl]-1,3-dioxolo[4,5-c]pyridine-6-carboxamide

EXAMPLE 121

N-((3R)-1-azabicyclo[3.2.2]nonan-3-yl)-1,3-benzoxazole-5-carboxamide

EXAMPLE 122

N-((3R)-1-azabicyclo[3.2.2]nonan-3-yl)-1,3-benzothiazole-6-carboxamide

EXAMPLE 123

N-((3R)-1-azabicyclo[3.2.2]nonan-3-yl)indane-5-carboxamide

EXAMPLE 124

N-((3R)-1-azabicyclo[3.2.2]nonan-3-yl)-1,3-benzodioxole-5-carboxamide

EXAMPLE 125

N-[(3R)-1-azabicyclo[3.2.2]nonan-3-yl]-1H-indazole-6-carboxamide

EXAMPLE 126

N-[(3R)-1-azabicyclo[3.2.2]nonan-3-yl]-1,3-dioxolo[4,5-c]pyridine-6-carboxamide

The benzothiazole and benzimidazole intermediates can be prepared using the methods as shown in Scheme 4 or Scheme 5, respectively. The benzoxazole intermediates can be prepared using methods described in Campaigne, E.; Van Verth, J. E., *J. Org. Chem.*, 1958, 23, 1344–1346, whereby the requisite o-aminophenol is treated with diethyloxalate. An alternate preparation of these compounds utilizes an approach described in *Pol. J. Pharm.*, 1984, 683–688, wherein the o-aminophenol is treated with glycolic acid. The resultant alcohol is then oxidized with $KMnO_4$ to afford the desired benzoxazole-2-carboxylic acid derivative. Similar approaches can be followed to afford the desired benzothiazole and benzimidazole derivatives.

The synthetic route to other compounds of interest is shown in Scheme 4. Heating C1010 in neat diethyl oxalate provides C1011. Alternatively, heating C1010 in neat glycolic acid provides an alcohol which is subsequently oxidized with $KMnO_4$ to afford C1012 (*Pol. J. Pharm.* 1984, 683–688). In yet another approach to compounds of the present invention, 2-halonitroaryl or heteroaryl compounds are subjected to amines wherein a well documented ipso-displacement of the halogen group occurs to provide a nitro-derivative that can be reduced, using methods well known to those or ordinary skill in the art, yielding C1016. Finally, using methods

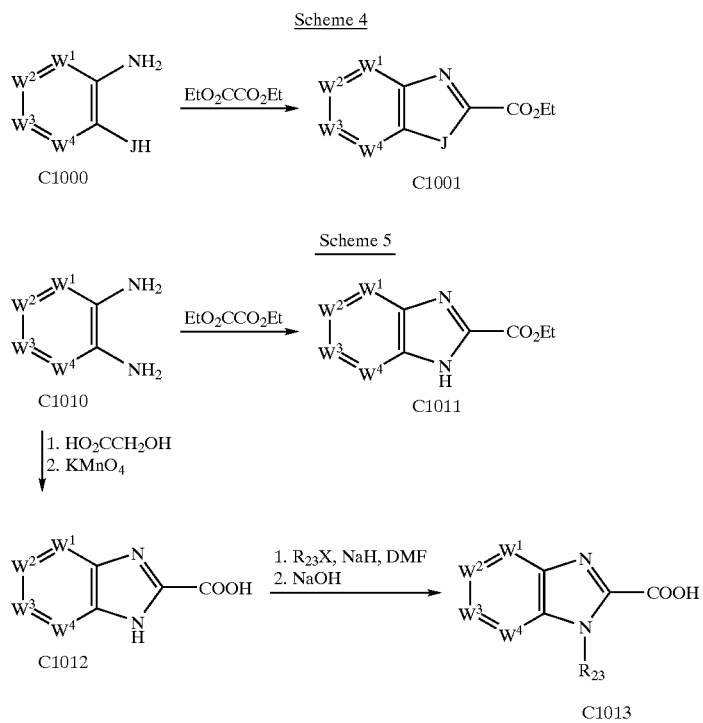

Alterntively, for where there is substitution on the imidazole:

described earlier, C1016 can be transformed into C1013

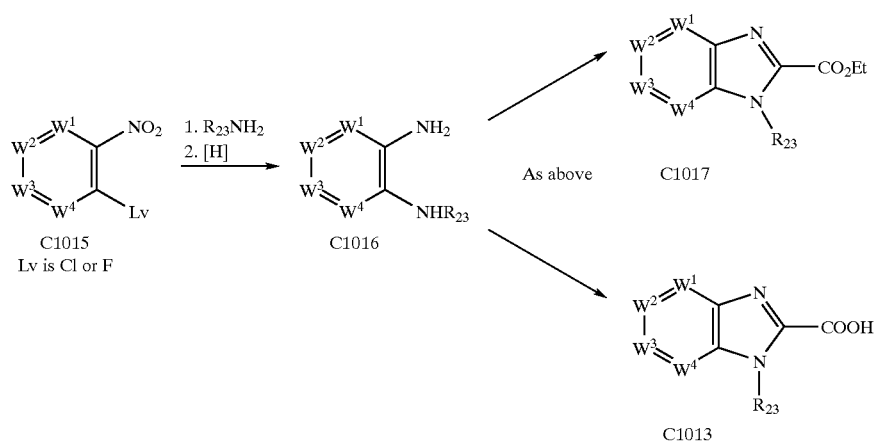

directly using diethyloxalate or into C1017 using glycolic acid followed by oxidation of the alcohol to the carboxylic acid.

The coupling of the Azabicyclo moiety occurs using either the carboxylic acids, such as C1012 or C1013, or the ethyl esters, such as C1001, C1011, or C1017, as shown in Scheme 6.

Scheme 6

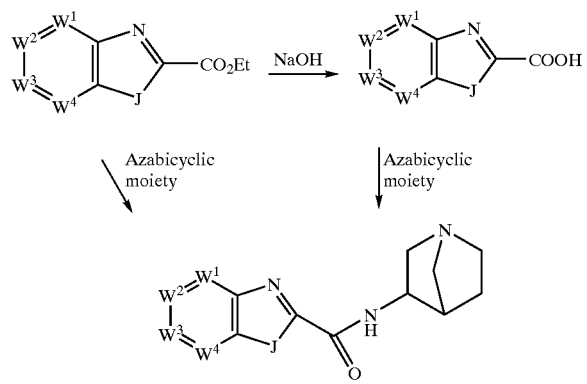

2-Carboethoxy derivatives can be directly coupled to the amino-azabicyclo moiety upon heating in the ester in ethanol at reflux. An alternate route entails subjecting the ester to hydrolysis providing a carboxylic acid. The carboxylic acid can then be coupled to the amino-azabicyclo moiety using a variety of amide bond coupling reagents.

EXAMPLE 1000

N-[1-azabicyclo[2.2.1]hept-3-yl]-1,3-benzothiazole-2-carboxamide

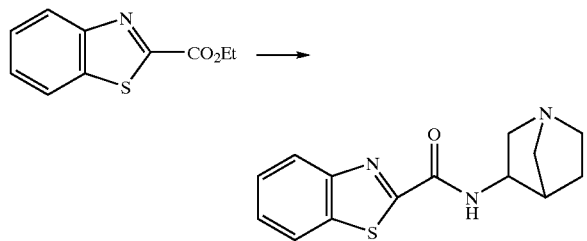

A solution of 2-aminothiophenol (10.7 mL, 0.1 mol) in diethyl oxalate (27.3 mL, 0.2 mol) is heated at reflux for 4 hr. The solution is cooled to rt and poured into a solution consisting of water (150 mL), conc. HCl (50 mL) and 95% EtOH (70 mL). With stirring, the oil dissolved and a solid formed. The solution is cooled in an ice bath, the solid is collected by vacuum filtration and the solids are washed with a solution consisting of EtOH/water (25/75) to afford a dark solid. This material is purified by crystallization from hot (68° C.) ligroin to yield ethyl 2-benzothiazolecarboxylate (7.5 g, 36%): Elemental analysis for $C_{10}H_9NO_2S$: Calc: C, 57.95; H, 4.38; N, 6.76. Found: C, 57.99; H, 4.28; N, 6.78.

Using procedures discussed herein, ethyl 2-benzothiazolecarboxylate and the exo- or endo-[2.2.1]-Amine are coupled to give the desired compound.

Materials and Methods for Determining α7 nAChR Agonist Activity

Cell-based Assay for Measuring the $EC_{50}$ of α7 nAChR Agonists

Construction and Expression of the α7-5HT$_3$ Receptor:

The cDNA encoding the N-terminal 201 amino acids from the human α7 nAChR that contain the ligand binding domain of the ion channel is fused to the cDNA encoding the pore forming region of the mouse 5HT$_3$ receptor as described by Eisele J L, et al., Chimaeric nicotinic-serotonergic receptor combines distinct ligand binding and channel specificities, Nature (1993), Dec. 2;366(6454):479–83, and modified by Groppi, et al., WO 00/73431. The chimeric α7-5HT$_3$ ion channel is inserted into pGS175 and pGS179 which contain the resistance genes for G-418 and hygromycin B, respectively. Both plasmids were simultaneously transfected into SH-EP1 cells and cell lines were selected that were resistant to both G-418 and hyrgromycin B. Cell lines expressing the chimeric ion channel were identified by their ability to bind fluorescent α-bungarotoxin on their cell surface. The cells with the highest amount of fluorescent α-bungarotoxin binding were isolated using a Fluorescent Activated Cell Sorter (FACS). Cell lines that stably expressed the chimeric α7-5HT$_3$ were identified by measuring fluorescent α-bungarotoxin binding after growing the cells in minimal essential medium containing nonessential amino acids supplemented with 10% fetal bovine serum, L-glutamine, 100 units/ml penicillin/streptomycin, 250 ng/mg fungizone, 400 μg/ml hygromycin B, and 400 μg/ml G-418 at 37° C. with 6% $CO_2$ in a standard mammalian cell incubator for at least 4 weeks in continuous culture.

Assay of the Activity of the Chimeric α7-5HT$_3$ Receptor

To assay the activity of the α7-5HT$_3$ ion channel, cells expressing the channel were plated into each well of either a 96 or 384 well dish (Coming #3614) and grown to confluence prior to assay. On the day of the assay, the cells were loaded with a 1:1 mixture of 2 mM Calcium Green 1, AM (Molecular Probes) dissolved in anhydrous DMSO and 20% pluronic F-127 (Molecular Probes). This solution is added directly to the growth media of each well to achieve a final concentration 2 μM. The cells were incubated with the dye for 60 min at 37° C. and then washed with a modified version of Earle's balanced salt solution (MMEBSS) as described in WO 00/73431. The ion conditions of the MMEBSS is adjusted to maximize the flux of calcium ion through the chimeric α7-5HT$_3$ ion channel as described in WO 00/73431. The activity of compounds on the chimeric α7-5HT$_3$ ion channel is analyzed on FLIPR. The instrument is set up with an excitation wavelength of 488 nanometers using 500 milliwatts of power. Fluorescent emission is measured above 525 nanometers with an appropriate F-stop to maintain a maximal signal to noise ratio. Agonist activity of each compound is measured by directly adding the compound to cells expressing the chimeric α7-5HT$_3$ ion channel and measuring the resulting increase in intracellular calcium that is caused by the agonist-induced activation of the chimeric ion channel. The assay is quantitative such that concentration-dependent increase in intracelluar calcium is measured as concentration-dependent change in Calcium Green fluorescence. The effective concentration needed for a compound to cause a 50% maximal increase in intracellular calcium is termed the $EC_{50}$. The following examples of the present invention have $EC_{50}$ values from about 180 nM to about 5700 nM: Example 1, Example 5, Example 6, Example 7, Example 10, Example 11, Example 12, and Example 105.

Binding Constants:

Another way for measuring α7 nAChR agonist activity is to determine binding constants of a potential agonist in a competition binding assay. For α7 nAChR agonists, there is good correlation between functional $EC_{50}$ values using the chimeric $\alpha7$-$5HT_3$ ion channel as a drug target and binding affinity of compounds to the endogenous $\alpha7$ nAChR.

Membrane Preparation.

Male Sprague-Dawley rats (300–350 g) are sacrificed by decapitation and the brains (whole brain minus cerebellum) are dissected quickly, weighed and homogenized in 9 volumes/g wet weight of ice-cold 0.32 M sucrose using a rotating pestle on setting 50 (10 up and down strokes). The homogenate is centrifuged at 1,000×g for 10 minutes at 4° C. The supernatant is collected and centrifuged at 20,000×g for 20 minutes at 4° C. The resulting pellet is resuspended to a protein concentration of 1–8 mg/mL. Aliquots of 5 mL homogenate are frozen at −80° C. until needed for the assay. On the day of the assay, aliquots are thawed at rt and diluted with Kreb's—20 mM Hepes buffer pH 7.0 (at rt) containing 4.16 mM $NaHCO_3$, 0.44 mM $KH_2PO_4$, 127 mM NaCl, 5.36 mM KCl, 1.26 mM $CaCl_2$, and 0.98 mM $MgCl_2$, so that 25–150 μg protein are added per test tube. Proteins are determined by the Bradford method (Bradford, M. M., *Anal. Biochem.*, 72, 248–254, 1976) using bovine serum albumin as the standard.

Binding Assay.

For saturation studies, 0.4 mL homogenate are added to test tubes containing buffer and various concentrations of radioligand, and are incubated in a final volume of 0.5 mL for 1 hour at 25° C. Nonspecific binding is determined in tissues incubated in parallel in the presence of 0.05 mls MLA for a final concentration of 1 μM, added before the radioligand. In competition studies, drugs are added in increasing concentrations to the test tubes before addition of 0.05 mls [$^3$H]-MLA for a final concentration 3.0 to 4.0 nM. The incubations are terminated by rapid vacuum filtration through Whatman GF/B glass filter paper mounted on a 48 well Brandel cell harvester. Filters are pre-soaked in 50 mM Tris HCl pH 7.0–0.05% polyethylenimine. The filters are rapidly washed two times with 5 mL aliquots of cold 0.9% saline and then counted for radioactivity by liquid scintillation spectrometry.

Data Analysis.

In competition binding studies, the inhibition constant (Ki) is calculated from the concentration dependent inhibition of [$^3$H]-MLA binding obtained from non-linear regression fitting program according to the Cheng-Prusoff equation (Cheng, Y. C. and Prussoff, W. H., *Biochem. Pharmacol.*, 22, p. 3099–3108, 1973). Hill coefficients were obtained using non-linear regression (GraphPad Prism sigmoidal dose-response with variable slope).

What is claimed is:

1. A compound of the Formula I:

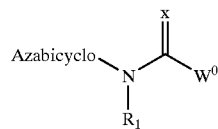

Formula I wherein X is O, or S;

Each $R_1$ is H, alkyl, cycloalkyl, halogenated alkyl, substituted phenyl, or substituted naphthyl;

Azabicyclo is

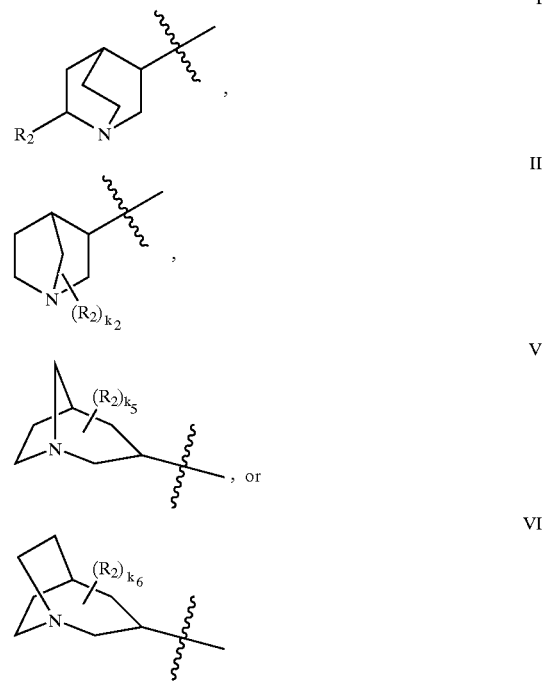

Each $R_2$ is independently alkyl, cycloalkyl, substituted phenyl, or substituted naphthyl, or $R_2$ is absent provided that $k_2$, $k_5$, or $k_6$ is 0;

$k_2$ is 0 or 1;

$k_5$ and $k_6$ are independently 0, 1, or 2;

$W^0$ is a bicyclic moiety and is

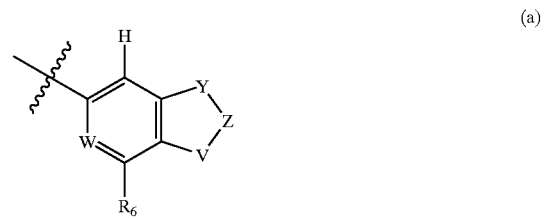

W is C(H) where
V---Z---Y is selected from O—C($R_3$)=N, O—C($R_5$)$_2$—N($R_4$), O—C($R_5$)$_2$—S, O—N=C($R_5$), C($R_5$)$_2$—O—C($R_5$)$_2$, S—C($R_3$)=N, S—C($R_5$)$_2$—N($R_4$), S—N=C($R_5$), N=C($R_3$)—O, N=C($R_3$)—S, N=C($R_3$)—N($R_4$), N($R_4$)—N=C($R_5$), N($R_4$)—C($R_5$)$_2$—O, N($R_4$)—C($R_5$)$_2$—S, N($R_4$)—C($R_5$)$_2$—N($R_4$), C($R_5$)$_2$—O—N($R_4$), C($R_5$)$_2$—S—C($R_5$)$_2$, C($R_5$)$_2$—N($R_4$)—C($R_5$)$_2$, C($R_5$)$_2$—N($R_4$)—O, C($R_5$)$_2$—N($R_4$)—S, C($R_5$)=N—O, C($R_5$)=N—S, C($R_5$)=N—N($R_4$), or C($R_5$)$_2$—C($R_3$)($R_5$)—C($R_5$)$_2$;

W is N where
V---Z---Y is selected from O—C($R_3$)=N, O—C($R_5$)$_2$—N($R_4$), O—C($R_5$)$_2$—S, O—N=C($R_5$) O—C($R_5$)$_2$—O, S—C($R_3$)=N, S—C($R_5$)$_2$—N($R_4$), S—N=C($R_5$), N=C($R_3$)—O, N=C($R_3$)—S, N=C($R_3$)—N($R_4$), N($R_4$)—N=C($R_3$), N($R_4$)—C($R_5$)$_2$—O, N($R_4$)—C($R_5$)$_2$—S, N($R_4$)—C($R_5$)$_2$—N($R_4$), C($R_5$)$_2$—O—N($R_4$), C($R_5$)$_2$—N($R_4$)—O, C($R_5$)$_2$—N($R_4$)—S, C($R_5$)=N—O, C($R_5$)=N—S, C($R_3$)=N—N($R_4$), or C($R_5$)=C($R_5$)—C($R_5$)$_2$;

Each $R_3$ is independently H, F, Cl, Br, I, alkyl, halogenated alkyl, substituted alkyl, cycloalkyl, lactam heterocycloalkyl, phenoxy, substituted phenoxy, $R_7$, $R_9$, —N($R_4$)-aryl, —N($R_4$)-halogenated phenyl, —N($R_4$)-halogenated naphthyl, —O-halogenated phenyl, —O-substituted phenyl, —O-halogenated naphthyl, —O-substituted naphthyl, —S-halogenated phenyl, —S-substituted phenyl, —S-halogenated naphthyl, —S-substituted naphthyl, or alkyl substituted on the ω carbon with $R_{15}$ where said ω carbon is determined by counting the longest carbon chain of the alkyl moiety with the C-1 carbon being the carbon attached to the bicyclic moiety $W^0$ and the ω carbon being the carbon furthest, e.g., separated by the greatest number of carbon atoms in the chain, from said C-1 carbon;

Each $R_4$ is H, or alkyl;

Each $R_5$ is independently H, F, alkyl, substituted alkyl, halogenated alkyl, alkenyl, substituted alkenyl, halogenated alkenyl, alkynyl, substituted alkynyl, halogenated alkynyl, cycloalkyl, —C(O)NH$_2$, —CO$_2R_1$, or aryl;

$R_6$ is H, F, Br, I, Cl, —CN, —CF$_3$, —OR$_{16}$, —SR$_{16}$, or —N(R$_{16}$)$_2$;

$R_7$ is 5-membered heteroaromatic mono-cyclic moieties containing within the ring 1–3 heteroatoms independently selected from the group consisting of —O—, =N—, —N(R$_{19}$)—, and —S—, and having 0–1 substituent selected from $R_{20}$ and further having 0–3 substituents independently selected from F, Cl, Br, or I, or $R_7$ is 9-membered fused-ring moieties having a 6-membered ring fused to a 5-membered ring and having the formula

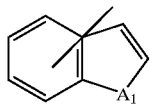

wherein $A_1$ is O, S, or $NR_{19}$,

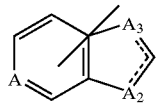

wherein A is $CR_{18}$ or N, $A_2$ and $A_3$ are independently selected from $CR_{18}$, $C(R_{18})_2$, O, S, N, or $NR_{19}$, provided that both $A_2$ and $A_3$ are not simultaneously O, simultaneously S, or simultaneously O and S, or

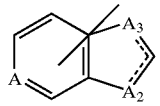

wherein $A_2$ and $A_3$ are independently selected from $CR_{18}$, $C(R_{18})_2$, O, S, N, or $NR_{19}$, and A is $CR_{18}$ or N, each 9-membered fused-ring moiety having 0–1 substituent selected from $R_{20}$ and further having 0–3 substituent(s) independently selected from F, Cl, Br, or I, and having a bond directly or indirectly attached to the core molecule where valency allows in either the 6-membered or the 5-membered ring of the fused-ring moiety;

$R_9$ is 6-membered heteroaromatic mono-cyclic moieties containing within the ring 1–3 heteroatoms selected from =N— and having 0–1 substituent selected from $R_{20}$ and 0–3 substituent(s) independently selected from F, Cl, Br, or I, or $R_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from $R_{20}$ and 0–3 substituent(s) independently selected from F, Cl, Br, or I and having a bond directly or indirectly attached to the core molecule where valency allows;

Each $R_{11}$ is independently H, alkyl, cycloalkyl, heterocycloalkyl, halogenated alkyl, halogenated cycloalkyl, or halogenated heterocycloalkyl;

$R_{13}$ is —OR$_{11}$, —SR$_{11}$, —N(R$_{11}$)$_2$, —C(O)R$_{11}$, —C(O)NR$_{11}$R$_{11}$, —CN, —CF$_3$, —NR$_{11}$C(O)R$_{11}$, —S(O)$_2$N(R$_{11}$)$_2$, —NR$_{11}$S(O)$_2$R$_{11}$, or —NO$_2$;

$R_{15}$ is aryl, $R_7$, or $R_9$;

$R_{16}$ is H, alkyl, substituted alkyl, cycloalkyl, halogenated alkyl, substituted phenyl, or substituted naphthyl;

Each $R_{18}$ is independently selected from H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)N(R$_{11}$)$_2$, —CN, —NR$_{11}$C(O)R$_{11}$, —S(O)$_2$N(R$_{11}$)$_2$, F, Cl, Br, or I, —NR$_{11}$S(O)$_2$R$_{11}$, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, or —NR$_{11}$S(O)$_2$R$_{11}$, and further provided that the fused-ring moiety has 0–3 substituent(s) selected from F, Cl, Br, or I;

$R_{19}$ is H, alkyl, halogenated alkyl, substituted alkyl, cycloalkyl, halogenated cycloalkyl, substituted cycloalkyl, phenyl, or phenyl having 1 substituent selected from $R_{20}$ and further having 0–3 substituents independently selected from F, Cl, Br, or I;

$R_{20}$ is alkyl, cycloalkyl, heterocycloalkyl, halogenated alkyl, halogenated cycloalkyl, halogenated heterocycloalkyl, —OR$_{11}$, —SR$_{11}$, —NR$_{11}$R$_{11}$, —C(O)R$_{11}$, —C(O)NR$_{11}$R$_{11}$, —CN, —NR$_{11}$C(O)R$_{11}$, —S(O)$_2$NR$_{11}$R$_{11}$, —NR$_{11}$S(O)$_2$R$_{11}$, —NO$_2$, alkyl substituted with 1–4 substituent(s) independently selected from F, Cl, Br, I, or $R_{13}$, cycloalkyl substituted with 1–4 substituent(s) independently selected from F, Cl, Br, I, or $R_{13}$, or heterocycloalkyl substituted with 1–4 substituent(s) independently selected from F, Cl, Br, I, or —R$_{13}$;

or a pharmaceutically acceptable salt thereof.

2. The compound of claim 1, wherein X is O.

3. The compound of claim 2, wherein $R_1$ is H, alkyl, or cycloalkyl.

4. The compound of claim 3, wherein (a) is 1,3-oxazolo[4,5-c]pyridin-6-yl, 1,3-oxazolo[5,4-c]pyridin-6-yl, 1,3-dioxolo[4,5-c]pyridin-6-yl, 1,3-benzoxazol-5-yl, 1,3-benzoxazol-6-yl, 1,2-benzisothiazol-5-yl, 1,2-benzisothiazol-6-yl, 1,3-thiazolo[4,5-c]pyridin-6-yl, 1,3-thiazolo[5,4-c]pyridin-6-yl, 1,3-benzothiazol-5-yl, 1,3- benzothiazol-6-yl, 1H-benzimidazole-5-yl, 1H-indazol-5-yl, 1H-indazol-6-yl, or indan-5-yl, any of which is optionally substituted as defined in claim 1.

5. The compound of claim 4, wherein each $k_2$, $k_5$, and $k_6$ is independently 0 or 1.

6. The compound of claim 5, wherein $R_2$ is alkyl, or $R_2$ is absent provided that Azabicyclo is II, V or VI and further provided that $k_2$, $k_5$, and $k_6$ are 0.

7. The compound of claim 6, wherein $R_1$ is H or lower alkyl, and wherein $R_2$ is lower alkyl or is absent provided that $k_2$, $k_5$, or $k_6$ is 0.

8. The compound of claim 7, wherein the compound is
N-(exo-4(S)-1-azabicyclo[2.2.1]hept-3-yl)-1,3-benzoxazole-5-carboxamide;
N-(exo-4(S)-1-azabicyclo[2.2.1]hept-3-yl)-1,3-benzothiazole-6-carboxamide;
N-[(exo-4S)-1-azabicyclo[2.2.1]hept-3-yl]-indane-5-carboxamide;
N-[(exo-4S)-1-azabicyclo[2.2.1]hept-3-yl]-1H-indazole-5-carboxamide;
N-[(exo-4S)-1-azabicyclo[2.2.1]hept-3-yl]-1H-indazole-6-carboxamide;
N-[(exo-4S)-1-azabicyclo[2.2.1]hept-3-yl]-1,3-dioxolo[4,5-c]pyridine-6-carboxamide;
N-[(3R,5R)-1-azabicyclo[3.2.1]oct-3-yl]-1,3-benzothiazole-6-carboxamide; or a pharmaceutically acceptable salt thereof, wherein the compound is the pure enantiomer or racemic mixture thereof.

9. The compound of claim 7, wherein the compound is
N-(1-(6-methyl)-azabicyclo[2.2.2]oct-3-yl)-1,3-benzoxazole-5-carboxamide;
N-(1-(6-methyl)-azabicyclo[2.2.2]oct-3-yl)-2-methyl-1,3-benzoxazole-5-carboxamide;
N-(1-(6-methyl)-azabicyclo[2.2.2]oct-3-yl)-1,3-benzoxazole-6-carboxamide;
N-(1-(6-methyl)-azabicyclo[2.2.2]oct-3-yl)-2-methyl-1,3-benzoxazole-6-carboxamide;
N-(1-(6-methyl)-azabicyclo[2.2.2]oct-3-yl)-1,3-benzothiazole-6-carboxamide;
N-(1-(6-methyl)-azabicyclo[2.2.2]oct-3-yl)indane-5-carboxamide;
N-(1-(6-methyl)-azabicyclo[2.2.2]oct-3-yl)-1,3-oxazolo[5,4-c]pyridine-6-carboxamide;
N-(1-(6-methyl)-azabicyclo[2.2.2]oct-3-yl)-1H-indazole-5-carboxamide;
N-(1-(6-methyl)-azabicyclo[2.2.2]oct-3-yl)-1H-indazole-6-carboxamide;
N-(1-(6-methyl)-azabicyclo[2.2.2]oct-3-yl)-1,3-dioxolo[4,5-c]pyridine-6-carboxamide;
N-(exo-4(S)-1-azabicyclo[2.2.1]hept-3-yl)-2-methyl-1,3-benzoxazole-5-carboxamide;
N-(exo-4(S)-1-azabicyclo[2.2.1]hept-3-yl)-1,3-benzoxazole-6-carboxamide;
N-(exo-4(S)-1-azabicyclo[2.2.1]hept-3-yl)-2-methyl-1,3-benzoxazole-6-carboxamide;
N-[exo-4(S)-1-azabicyclo[2.2.1]hept-3-yl]-1,3-oxazolo[5,4-c]pyridine-6-carboxamide;
N-(exo-4(S)-1-(6-methyl)-azabicyclo[2.2.1]hept-3-yl)-1,3-benzoxazole-5-carboxamide;
N-(exo-4(S)-1-(6-methyl)-azabicyclo[2.2.1]hept-3-yl)-2-methyl-1,3-benzoxazole-5-carboxamide;
N-(exo-4(S)-1-(6-methyl)-azabicyclo[2.2.1]hept-3-yl)-1,3-benzoxazole-6-carboxamide;
N-(exo-4(S)-1-(6-methyl)-azabicyclo[2.2.1]hept-3-yl)-2-methyl-1,3-benzoxazole-6-carboxamide;
N-(exo-4(S)-1-(6-methyl)-azabicyclo[2.2.1]hept-3-yl)-1,3-benzothiazole-6-carboxamide;
N-(exo-4(S)-1-(6-methyl)-azabicyclo[2.2.1]hept-3-yl)indane-5-carboxamide;
N-(exo-4(S)-1-(6-methyl)-azabicyclo[2.2.1]hept-3-yl)-1,3-oxazolo[5,4-c]pyridine-6-carboxamide;
N-(exo-4(S)-1-(6-methyl)-azabicyclo[2.2.1]hept-3-yl)-1H-indazole-5-carboxamide;
N-(exo-4(S)-1-(6-methyl)-azabicyclo[2.2.1]hept-3-yl)-1H-indazole-6-carboxamide;
N-(exo-4(S)-1-(6-methyl)-azabicyclo[2.2.1]hept-3-yl)-1,3-dioxolo[4,5-c]pyridine-6-carboxamide;
N-[(3R,5R)-1-azabicyclo[3.2.1]oct-3-yl]-1,3-benzoxazole-5-carboxamide;
N-[(3R,5R)-1-azabicyclo[3.2.1]oct-3-yl]-2-methyl-1,3-benzoxazole-5-carboxamide;
N-[(3R,5R)-1-azabicyclo[3.2.1]oct-3-yl]-1,3-benzoxazole-6-carboxamide;
N-[(3R,5R)-1-azabicyclo[3.2.1]oct-3-yl]-2-methyl-1,3-benzoxazole-6-carboxamide;
N-[(3R,5R)-1-azabicyclo[3.2.1]oct-3-yl]indane-5-carboxamide;
N-[(3R,5R)-1-azabicyclo[3.2.1]oct-3-yl]-1,3-oxazolo[5,4-c]pyridine-6-carboxamide;
N-[(3R,5R)-1-azabicyclo[3.2.1]oct-3-yl]-1H-indazole-5-carboxamide;
N-[(3R,5R)-1-azabicyclo[3.2.1]oct-3-yl]-1H-indazole-6-carboxamide;
N-[(3R,5R)-1-azabicyclo[3.2.1]oct-3-yl]-1,3-dioxolo[4,5-c]pyridine-6-carboxamide;
N-((3R)-1-azabicyclo[3.2.2]nonan-3-yl)-1,3-benzoxazole-5-carboxamide;
N-((3R)-1-azabicyclo[3.2.2]nonan-3-yl)-1,3-benzothiazole-6-carboxamide;
N-((3R)-1-azabicyclo[3.2.2]nonan-3-yl)indane-5-carboxamide;
N-[(3R)-1-azabicyclo[3.2.2]nonan-3-yl]-1H-indazole-6-carboxamide;
N-[(3R)-1-azabicyclo[3.2.2]nonan-3-yl]-1,3-dioxolo[4,5-c]pyridine-6-carboxamide; or a pharmaceutically acceptable salt thereof, wherein the compound is the pure enantiomer or racemic mixture thereof.

10. The compound of claim 7, wherein the compound is
N-[exo-4(S)-1-azabicyclo[2.2.1]hept-3-yl]-1,2-benzisothiazole-6-carboxamide;
N-[exo-4(S)-1-azabicyclo[2.2.1]hept-3-yl]-1,2-benzisothiazole-5-carboxamide;
N-[(3R,5R)-1-azabicyclo[3.2.1]oct-3-yl]-1H-indazole-5-carboxamide;
N-[(3R,5R)-1-azabicyclo[3.2.1]oct-3-yl]-3-methyl-1H-indazole-6-carboxamide;
N-[(3R,5R)-1-azabicyclo[3.2.1]oct-3-yl]-3-methyl-1H-indazole-5-carboxamide;
N-[(3R,5R)-1-azabicyclo[3.2.1]oct-3-yl]-3-ethyl-1H-indazole-6-carboxamide;
N-[(3R,5R)-1-azabicyclo[3.2.1]oct-3-yl]-3-ethyl-1H-indazole-5-carboxamide;
N-[(3R,5R)-1-azabicyclo[3.2.1]oct-3-yl]-1,2-benzisothiazole-6-carboxamide;
N-[(3R,5R)-1-azabicyclo[3.2.1]oct-3-yl]-1,2-benzisothiazole-5-carboxamide;

N-[(3R,5R)-1-azabicyclo[3.2.1]oct-3-yl]-3-ethyl-1,2-benzisothiazole-6-carboxamide;

N-[(3R,5R)-1-azabicyclo[3.2.1]oct-3-yl]-3-ethyl-1,2-benzisothiazole-5-carboxamide;

N-[(3R,5R)-1-azabicyclo[3.2.1]oct-3-yl]-3-methyl-1,2-benzisothiazole-6-carboxamide;

N-[(3R,5R)-1-azabicyclo[3.2.1]oct-3-yl]-3-methyl-1,2-benzisothiazole-5-carboxamide;

N-[(3R,5R)-1-azabicyclo[3.2.1]oct-3-yl]-2-cyclopropyl-1,3-benzoxazole-6-carboxamide;

N-[(3R,5R)-1-azabicyclo[3.2.1]oct-3-yl]-2-cyclopropyl-1,3-benzoxazole-5-carboxamide;

N-[(3R,5R)-1-azabicyclo[3.2.1]oct-3-yl]-2-cyclopropyl-1,3-benzothiazole-6-carboxamide;

N-[(3R,5R)-1-azabicyclo[3.2.1]oct-3-yl]-2-cyclopropyl-1,3-benzothiazole-5-carboxamide;

N-[(3R,5R)-1-azabicyclo[3.2.1]oct-3-yl]-2-methyl-1,3-benzothiazole-6-carboxamide;

N-[(3R,5R)-1-azabicyclo[3.2.1]oct-3-yl]-2-methyl-1,3-benzothiazole-5-carboxamide;

N-[(3R,5R)-1-azabicyclo[3.2.1]oct-3-yl]-2-methyl-1,3-benzodioxole-6-carboxamide;

N-[(3R,5R)-1-azabicyclo[3.2.1]oct-3-yl]-2-ethyl-1,3-benzodioxole-5-carboxamide;

N-[(3R,5R)-1-azabicyclo[3.2.1]oct-3-yl]-1H-benzimidazole-5-carboxamide;

N-[(3R,5R)-1-azabicyclo[3.2.1]oct-3-yl]-1,3-thiazolo[5,4-c]pyridine-6-carboxamide;

N-[(3R,5R)-1-azabicyclo[3.2.1]oct-3-yl]-1,3-thiazolo[4,5-c]pyridine-6-carboxamide;

N-[(3R,5R)-1-azabicyclo[3.2.1]oct-3-yl]-1,3-dioxolo[4,5-c]pyridine-6-carboxamide;

N-[(3R,5R)-1-azabicyclo[3.2.1]oct-3-yl]-1,3-oxazolo[4,5-c]pyridine-6-carboxamide; or a pharmaceutically acceptable salt thereof, wherein the compound is the pure enantiomer or racemic mixture thereof.

11. A pharmaceutical composition comprising a compound according to claim 1 and a pharmaceutically acceptable excipient.

12. The pharmaceutical composition according to claim 11, wherein said compound is administered rectally, topically, orally, sublingually, or parenterally for a therapeutically effective interval.

13. The pharmaceutical composition according to claim 11, wherein said compound is administered in an amount of from about 0.001 to about 100 mg/kg of body weight of said mammal per day.

14. The pharmaceutical composition according to claim 11, wherein said compound is administered in an amount of from about 0.1 to about 50 mg/kg of body weight of said mammal per day.

15. A method for treating a disease or condition in a mammal in need thereof, wherein the mammal would receive symptomatic relief from the administration of an α7 nicotinic acetylcholine receptor agonist comprising administering to the mammal a therapeutically effective amount of a compound according to claim 1.

16. The method according to claim 15, wherein the disease or condition is cognitive and attention deficit symptoms of Alzheimer's, neurodegeneration associated with diseases such as Alzheimer's disease, pre-senile dementia (mild cognitive impairment), or senile dementia.

17. The method according to claim 15, wherein the disease or condition is schizophrenia or psychosis.

18. The method of claim 17, wherein the mammal would receive symptomatic relief from the administration of a therapeutically effective amount of α7 nicotinic acetylcholine receptor agonist and an anti-psychotic agent for a therapeutically effective interval comprising adminstering to the mammal in addition a therapeutically effective amount of an anti-psychotic agent.

19. The method according to claim 15, wherein the disease or condition is depression, or anxiety and general anxiety disorders and post traumatic stress disorder.

20. The method according to claim 15, wherein the disease or condition is attention deficit disorder, or attention deficit hyperactivity disorder.

21. The method according to claim 15, wherein the disease or condition is mood and affective disorders, amyotrophic lateral sclerosis, borderline personality disorder, traumatic brain injury, behavioral and cognitive problems in general and associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulemia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

22. A compound of the Formula I;

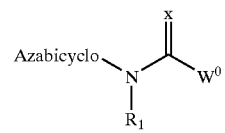

Formula I wherein X is O, or S;

Each $R_1$ is H, alkyl, cycloalkyl, halogenated alkyl, substituted phenyl, or substituted naphthyl;

Azabicyclo is

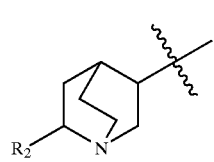

I

,

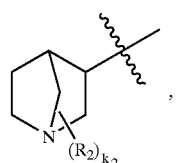

II

,

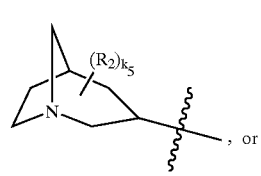

V

, or

-continued

VI

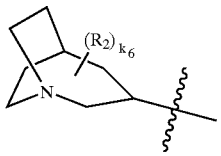

Each R$_2$ is independently alkyl, cycloalkyl, substituted phenyl, or substituted naphthyl, or R$_2$ is absent provided that k$_2$, k$_5$, or k$_6$ is 0;
k$_2$ is 0 or 1;
k$_5$ and k$_6$ are independently 0, 1, or 2;
W$^0$ is a bicyclic moiety and is (a)

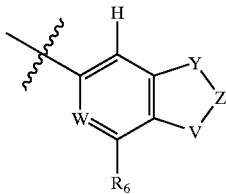

W is N where
V---Z---Y is selected from O—C(R$_3$)=N, O—C(R$_5$)$_2$—N(R$_4$), O—C(R$_5$)$_2$—S, O—N=C(R$_5$) O—C(R$_5$)$_2$—O, S—C(R$_3$)=N, S—C(R$_5$)$_2$—N(R$_4$), S—N=C(R$_5$), N=C(R$_3$)—O, N=C(R$_3$)—S, N=C(R$_3$)—N(R$_4$), N(R$_4$)—N=C(R$_3$), N(R$_4$)—C(R$_5$)$_2$—O, N(R$_4$)—C(R$_5$)$_2$—S, N(R$_4$)—C(R$_5$)$_2$—N(R$_4$), C(R$_5$)$_2$—O—N(R$_4$), C(R$_5$)$_2$—N(R$_4$)—O, C(R$_5$)$_2$—N(R$_4$)—S, C(R$_5$)=N—O, C(R$_5$)=N—S, C(R$_3$)=N—N(R$_4$), or C(R$_5$)=C(R$_5$)—C(R$_5$)$_2$;
Each R$_3$ is independently H, F, Cl, Br, I, alkyl, halogenated alkyl, substituted alkyl, cycloalkyl, lactam heterocycloalkyl, phenoxy, substituted phenoxy, R$_7$, R$_9$, —N(R$_4$)-aryl —N(R$_4$)-halogenated phenyl, —N(R$_4$)-halogenated naphthyl, —O-halogenated phenyl, —O-substituted phenyl, —O-halogenated naphthyl, —O-substituted naphthyl, —S-halogenated phenyl, —S-substituted phenyl, —S-halogenated naphthyl, —S-substituted naphthyl, or alkyl substituted on the ω carbon with R$_{15}$ where said ω carbon is determined by counting the longest carbon chain of the alkyl moiety with the C-1 carbon being the carbon attached to the bicyclic moiety W$^0$ and the ω carbon being the carbon furthest, e.g., separated by the greatest number of carbon atoms in the chain, from said C-1 carbon;
Each R$_4$ is H, or alkyl;
Each R$_5$ is independently H, F, alkyl, substituted alkyl, halogenated alkyl, alkenyl, substituted alkenyl, halogenated alkenyl, alkynyl, substituted alkynyl, halogenated alkynl, cycloalkyl, —C(O)NH$_2$, —CO$_2$R$_1$, or aryl;
R$_6$ is H, F, Br, I, Cl, —CN, —CF$_3$, —OR$_{16}$, —SR$_{16}$, or —N(R$_{16}$)$_2$;
R$_7$ is 5-membered heteroaromatic mono-cyclic moieties containing within the ring 1–3 heteroatoms independently selected from the group consisting of —O—, =N—, —N(R$_{19}$)—, and —S—, and having 0–1 substituent selected from R$_{20}$ and further having 0–3 substituents independently selected from F, Cl, Br, or I, or R$_7$ is 9-membered fused-ring moieties having a 6-membered ring fused to a 5-membered ring and having the formula

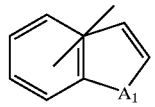

wherein A$_1$ is O, S, or NR$_{19}$,

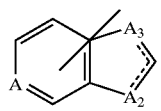

wherein A is CR$_{18}$ or N, A$_2$ and A$_3$ are independently selected from CR$_{18}$, C(R$_{18}$)$_2$, O, S, N, or NR$_{19}$, provided that both A$_2$ and A$_3$ are not simultaneously O, simultaneously S, or simultaneously O and S, or

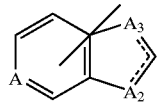

wherein A$_2$ and A$_3$ are independently selected from CR$_{18}$, C(R$_{18}$)$_2$, O, S, N, or NR$_{19}$, and A is CR$_{18}$ or N, each 9-membered fused-ring moiety having 0–1 substituent selected from R$_{20}$ and further having 0–3 substituent(s) independently selected from F, Cl, Br, or I, and having a bond directly or indirectly attached to the core molecule where valency allows in either the 6-membered or the 5-membered ring of the fused-ring moiety;
R$_9$ is 6-membered heteroaromatic mono-cyclic moieties containing within the ring 1–3 heteroatoms selected from =N— and having 0–1 substituent selected from R$_{20}$ and 0–3 substituent(s) independently selected from F, Cl, Br, or I, or R$_9$ is 10-membered heteroaromatic bi-cyclic moieties containing within one or both rings 1–3 heteroatoms selected from =N—, including, but not limited to, quinolinyl or isquinolinyl, each 10-membered fused-ring moiety having 0–1 substituent selected from R$_{20}$ and 0–3 substituent(s) independently selected from F, Cl, Br, or I and having a bond directly or indirectly attached to the core molecule where valency allows;
Each R$_{11}$ is independently H, alkyl, cycloalkyl, heterocycloalkyl, halogenated alkyl, halogenated cycloalkyl, or halogenated heterocycloalkyl;
R$_{13}$ is —OR$_{11}$, —SR$_{11}$, —N(R$_{11}$)$_2$, —C(O)R$_{11}$, —C(O)NR$_{11}$R$_{11}$, —CN, —CF$_3$, —NR$_{11}$C(O)R$_{11}$, —S(O)$_2$N(R$_{11}$)$_2$, —NR$_{11}$S(O)$_2$R$_{11}$, or —NO$_2$;
R$_{15}$ is aryl, R$_7$, or R$_9$;
R$_{16}$ is H, alkyl, substituted alkyl, cycloalkyl, halogenated alkyl, substituted phenyl, or substituted naphthyl;
Each R$_{18}$ is independently selected from H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)N(R$_{11}$)$_2$, —CN, —NR$_{11}$C(O)R$_{11}$, —S(O)$_2$N(R$_{11}$)$_2$, F, Cl, Br, or I, —NR$_{11}$S(O)$_2$R$_{11}$, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, $-OR_{11}$, $-SR_{11}$, $NR_{11}R_{11}$, $-C(O)R_{11}$, $-NO_2$, $-C(O)NR_{11}R_{11}$, $-CN$, $-NR_{11}C(O)R_{11}$, $-S(O)_2NR_{11}R_{11}$, or $-NR_{11}S(O)_2R_{11}$, and further provided that the fused-ring moiety has 0–3 substituent(s) selected from F, Cl, Br, or I;

$R_{19}$ is H, alkyl, halogenated alkyl, substituted alkyl, cycloalkyl, halogenated cycloalkyl, substituted cycloalkyl, phenyl, or phenyl having 1 substituent selected from $R_{20}$ and further having 0–3 substituents independently selected from F, Cl, Br, or I;

$R_{20}$ is alkyl, cycloalkyl, heterocycloalkl, halogenated alkyl, halogenated cycloalkyl, halogenated heterocycloalkyl, $-OR_{11}$, $-SR_{11}$, $-NR_{11}R_{11}$, $-C(O)R_{11}$, $-C(O)NR_{11}R_{11}$, $-CN$, $-NR_{11}C(O)R_{11}$, $-S(O)_2NR_{11}R_{11}$, $-NR_{11}S(O)_2R_{11}$, $-NO_2$, alkyl substituted with 1–4 substituent(s) independently selected from F, Cl, Br I, or $R_{13}$, cycloalkyl substituted with 1–4 substituent(s) independently selected from F, Cl, Br, I, or $R_{13}$ or heterocycloalkyl substituted with 1–4 substituent(s) independently selected from F, Cl, Br, I, or $-R_{13}$;

or a pharmaceutically acceptable salt thereof.

23. The compound of claim 22, wherein X is O.

24. The compound of claim 23, wherein $R_1$ is H, alkyl, or cycloalkyl.

25. The compound of claim 24, wherein (a) is 1,3-oxazolo[4,5-c]pyridin-6-yl, 1,3-oxazolo[5,4-c]pyridin-6-yl, 1,3-dioxolo[4,5-c]pyridin-6-yl, 1,3-thiazolo[4,5-c]pyridin-6-yl, or 1,3-thiazolo[5,4-c]pyridin-6-yl, any of which is optionally substituted as defined in claim 22.

26. The compound of claim 25, wherein each $k_2$, $k_5$, and $k_6$ is independently 0 or 1.

27. The compound of claim 26, wherein $R_2$ is alkyl, of $R_2$ is absent provided that Azabicyclo is II, V or VI and further provided that $k_2$, $k_5$, and $k_6$ are 0.

28. The compound of claim 27, wherein $R_1$ is H or lower alkyl, and wherein $R_2$ lower alkyl or is absent provided $k_2$, $k_5$, or $k_6$ is 0.

29. The compound of claim 28, wherein the compound is
N-[(exo-4S)-1-azabicyclo[2.2.1]hept-3-yl]-1,3-dioxolo[4,5-c]pyridine-6-carboxamide; or a pharmaceutically acceptable salt thereof, provided that the compound is the pure, enantiomer or racemic mixture thereof.

30. The compound of claim 28, wherein the compound is
N-(1-(6-methyl)-azabicyclo[2.2.2]oct-3-yl)-1,3-oxazolo[5,4-c]pyridine-6-carboxamide;
N-(1-(6-methyl)-azabicyclo[2.2.2]oct-3-yl)-1,3-dioxolo[4,5-c]pyridine-6-carboxamide;
N-[exo-4(S)-1-azabicyclo[2.2.1]hept-3-yl]-1,3-oxazolo[5,4-c]pyridine-6-carboxamide;
(N-(exo-4(S)-1-(6-methyl)-azabicyclo[2.2.1]hept-3-yl)-1,3-oxazolo[5,4-c]pyridine-6-carboxamide;
N-(exo-4(S)-1-(6-methyl)-azabicyclo[2.2.1]hept-3-yl)-1,3-dioxolo[4,5-c]pyridine-6-carboxamide;
N-[(3R,5R)-1-azabicyclo[3.2.1]oct-3-yl]-1,3-oxazolo[5,4-c]pyridine-6-carboxamide;
N-[(3R,5R)-1-azabicyclo[3.2.1]oct-3-yl]-1,3-dioxolo[4,5-c]pyridine-6-carboxamide; N-[(3R)-1-azabicyclo[3.2.2]nonan-3-yl]-1,3-dioxolo[4,5-c]pyridine-6-carboxamide; or a pharmaceutically acceptable salt thereof, provided that the compound is the pure enantiomer or racemic mixture thereof.

31. The compound of claim 28, wherein the compound is
N-[(3R,5R)-1-azabicyclo[3.2.1]oct-3-yl]-1,3-thiazolo[5,4-c]pyridine-6-carboxamide;
N-[(3R,5R)-1-azabicyclo[3.2.1]oct-3-yl]-1,3-thiazolo[4,5-c]pyridine-6-carboxamide;
N-[(3R,5R)-1-azabicyclo[3.2.1]oct-3-yl]-1,3-dioxolo[4,5-c]pyridine-6-carboxamide;
N-[(3R,5R)-1-azabicyclo[3.2.1]oct-3-yl]-1,3-oxazolo[4,5-c]pyridine-6-carboxamide; or a pharmaceutically acceptable salt thereof, provided that the compound is the pure enantiomer or racemic mixture thereof.

* * * * *